US010945962B2

(12) United States Patent
Vetro et al.

(10) Patent No.: US 10,945,962 B2
(45) Date of Patent: Mar. 16, 2021

(54) CONTROLLED-RELEASE PEPTIDE COMPOSITIONS AND USES THEREOF

(71) Applicant: BOARD OF REGENTS OF THE UNIVERSITY OF NEBRASKA, Lincoln, NE (US)

(72) Inventors: Joseph A. Vetro, Logan, IA (US); Sam D. Sanderson, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

(21) Appl. No.: 16/209,300

(22) Filed: Dec. 4, 2018

(65) Prior Publication Data

US 2019/0083408 A1  Mar. 21, 2019

Related U.S. Application Data

(62) Division of application No. 14/362,040, filed as application No. PCT/US2012/067454 on Nov. 30, 2012, now Pat. No. 10,220,002.

(60) Provisional application No. 61/566,144, filed on Dec. 2, 2011.

(51) Int. Cl.
| | |
|---|---|
| A61K 9/46 | (2006.01) |
| A61K 38/08 | (2019.01) |
| C07K 16/18 | (2006.01) |
| A61K 9/48 | (2006.01) |
| A61K 38/17 | (2006.01) |
| A61K 39/00 | (2006.01) |
| C07K 16/28 | (2006.01) |
| A61K 9/00 | (2006.01) |
| A61K 9/50 | (2006.01) |

(52) U.S. Cl.
CPC .............. A61K 9/48 (2013.01); A61K 38/08 (2013.01); A61K 38/1725 (2013.01); A61K 39/0005 (2013.01); C07K 16/18 (2013.01); C07K 16/28 (2013.01); A61K 9/0019 (2013.01); A61K 9/5031 (2013.01); A61K 2039/505 (2013.01); C07K 2317/34 (2013.01)

(58) Field of Classification Search
None
See application file for complete search history.

(56) References Cited

U.S. PATENT DOCUMENTS

| | | | |
|---|---|---|---|
| 5,422,120 A | 6/1995 | Kim | |
| 5,696,230 A | 12/1997 | Sanderson et al. | |
| 6,465,614 B1 * | 10/2002 | Sanderson | C07K 14/472 424/185.1 |
| 6,821,517 B1 | 11/2004 | Sanderson et al. | |
| 7,358,087 B2 | 4/2008 | Sanderson et al. | |
| 9,895,411 B2 * | 2/2018 | Sanderson | A61K 38/10 |
| 2011/0003756 A1 | 1/2011 | Hummel et al. | |
| 2011/0021416 A1 | 1/2011 | Shapiro | |

OTHER PUBLICATIONS

Akagi et al. (Adv Polym Sci (2012) 247: 31-64, Published online: Oct. 20, 2011) (Year: 2011).*
Nobs et al. (J Pharm Sci. Aug. 2004;93(8):1980-92) (Year: 2004).*
Kirchhoff et al. (Immunology. Jun. 2001; 103(2): 210-217) (Year: 2001).*
Krishnamachari et al. (Pharm Res. Feb. 2011; 28(2): 215-236) (Year: 2011).*
Black et al. (Expert Rev Vaccines. Feb. 2010; 9(2): 157-173) (Year: 2010).*
Phillips et al. (Bioconjugate Chem. 2009, 20, 1950-1957) (Year: 2009).*
Acharya et al., PLGA nanoparticles containing various anticancer agents and tumour delivery by EPR effect, Adv. Drug Deilv. Rev., 63(3):170-83 (2011).
Antosova et al., Therapeutic application of peptides and proteins: parenteral forever?, Trends Biotechnol., 27:628-635 (2009).
Banerjee et al., Activation of brain endothelium by pneumococcal neuraminidase NanA promotes bacterial internalization, Cell Microbiol., 12:1576-88 (2010).
Benny et al., Continuous delivery of endogenous inhibitors from poly(lactic-co-glycolic acid) polymeric microspheres inhibits glioma tumor growth, Clin. Cancer Res., 11:768-76 (2005).
Benny et al., In vivo fate and therapeutic efficacy of PF-4/CTF microspheres in an orthotopic human glioblastoma model, Faseb J., 22:488-99 (2008).
Bradley et al., Measurement of Cutaneous Inflammation: Estimation of Neutrophil Content with an Enzyme Marker, J. Invest. Dermatol., 78:206-9 (1982).
Brown, Commercial challenges of protein drug delivery, Expert Opin. Drug Deilv., 2:29-42 (2005).
Buchner et al., Anti-human kappa opioid receptor antibodies: characterization of site-directed neutralizing antibodies specific for a peptide kappa R(33-52) derived from the predicted amino terminal region of the human kappa receptor, J. Immunol., 158:1670-80 (1996).
Bunce et al., Murine model of cutaneous infection with gram-positive cocci, Infect. Immun., 60:2636-40 (1992).
Bysell et al., Microgels and microcapsules in peptide and protein drug delivery, Adv. Drug Del. Rev., 63(13):1172-85 (2011).
Daley et al., Use of Ly6G-specific monoclonal antibody to deplete neutrophils in mice, J. Leukoc. Biol., 83:64-70 (2008).
Danhier, et al., PGLA-based nanoparticles: an overview of biomedical applications, J. Control Release, 161(2):505-22 (2012).

(Continued)

Primary Examiner — Sergio Coffa
(74) Attorney, Agent, or Firm — Hovey Williams LLP

(57) ABSTRACT

Controlled-release formulations of carboxy-terminal C5a analogs (such as sustained-release formulations of the analogs), and their use in methods for treating and preventing an infection or a disease such as cancer, for directly killing microorganisms, for vaccine preparation, for inducing an immune response and for targeting antigen-presenting cells and other cells bearing a C5a receptor, are provided.

17 Claims, 3 Drawing Sheets

Specification includes a Sequence Listing.

(56) References Cited

OTHER PUBLICATIONS

Degim et al., Controlled delivery of peptides and proteins. Curr Pharmaceut Design, 13:99-117 (2007).
Drapeau et al., Synthetic C5a receptor agonists. Pharmacology, metabolism and in vivo cardiovascular and hematologic effects, Biochem. Pharmacol., 45:1289-99 (1993).
Duryee et al., Immune responses to methamphetamine by active immunization with peptide-based, molecular adjuvant-containing vaccines, Vaccine, 27:2981-8 (2009).
Ember et al., Biologic activity of synthetic analogues of C5a anaphylatoxin, J. Immunol., 148:3165-73 (1992).
Ertl et al., Poly (DL-lactide-co-glycolide) microspheres as carriers for peptide vaccines, Vaccine, 14:879-85 (1996).
Floreani et al., Novel C5a agonist-based dendritic cell vaccine in a murine model of melanoma, Cell Cycle, 6:2835-9 (2007).
Hegde et al., A conformationally-biased, response-selective agonist of C5a acts as a molecular adjuvant by modulating antigen processing and presentation activities of human dendritic cells, Int. Immunopharmacol., 8:819-27 (2008).
Highlander et al., Subtle genetic changes enhance virulence of methicillin resistant and sensitive *Staphylococcus aureus*, BMC Microbiol., 7:99 (2007).
Hoesel et al., Harmful and protective roles of neutrophils in sepsis, Shock, 24:40-47 (2005).
Holtappels et al., Identification of a K(d)-restricted antigenic peptide encoded by murine cytomegalovirus early gene M84, J. Gen. Virol., 81:3037-42 (2000).
Hugli et al., Mechanisms of leukocyte regulation by complement-derived factors, Chapter 4 in Regulation of Leukocyte Function, R. Snyderman, ed., Plenum Publishing Corp., 109-53 (1984).
Hung, et al., An agonist of human complement fragment C5a enhances vaccine immunity against Coccidioides Infection, Vaccine, 30(31):4681-90 (2012).
Jiang et al., Biodegradable poly(lactic-co-glycolic acid) microparticles for injectable delivery of vaccine antigens, J. Adv. Drug. Deilv. Rev., 57:391-410 (2005).
Kawai et al., Structure-function studies in a series of carboxyl-terminal octapeptide analogues of anaphylatoxin C5a, J. Med. Chem., 35:220-3 (1992).
Kohl et al., Evaluation of the C-terminal C5a effector site with short synthetic C5a analog peptides, Eur. J. Immunol., 23:646-52 (1993).
Kollessery, et al., Tumor-specific peptide-based vaccines containing the comformationally biased, response-selective C5a agonists EP54 and EP67 protect against aggressive large B cell lymphoma in a syngeneic murine model, Vaccine, 29(3):5904-5910 (2011).
Kontermann et al., Strategies for extended serum half-life of protein therapeutics, Curr. Opin Biotechnol., 22:868-76 (2011).
Langer et al., Biocompatible controlled release polymers for delivery of polypeptides and growth factors, J. Cell. Biochem., 45:340-5 (1991).
Lehninger, Biochemistry, 2nd Edition; Worth Publishers, Inc., New York, 71-77 (1975).
Li et al., Microencapsulation by solvent evaporation: state of the art for process engineering approaches, Intl. J. Pharm., 363:26-39 (2008).
Luan et al., Key parameters affecting the initial release (burst) and encapsulation efficiency of peptide-containing poly(lactide-co-glycolide) microparticles, Int. J. Pharm., 324:168-75 (2006).
Mollison et al., C5a structural requirements for neutrophil receptor interaction, Agents and Actions, Suppl., 35:17-21 (1991).
Morgan et al., A novel adjuvant for vaccine development in the aged, Vaccine, 28:8275-9 (2010).
Morgan et al., Enhancement of in vivo and in vitro immune functions by a conformationally biased, response-selective agonist of human C5a: implications for a novel adjuvant in vaccine design, Vaccine, 28(2):463-9 (2009).
Morgan et al., Identification and characterization of the effector region within human C5a responsible for stimulation of IL-6 synthesis, J. Immunol., 148:3937-42 (1992).

Moynihan et al., A novel microencapsulated peptide vaccine against hepatitis B, Vaccine, 19:3292-300 (2001).
Nestor, The medicinal chemistry of peptides, Curr. Med. Chem., 16:4399-418 (2009).
Newman et al., Delivery of MUC1 mucin peptide by Poly(d,l-lactic-co-glycolic acid) microspheres induces type 1 T helper immune responses, J. Pharm. Sci., 87:1421-7 (1998).
Nishikawa et al., Development of a novel antimicrobial peptide, AG-30, with angiogenic properties, J. Cell. Molec. Med., 13:535-46 (2009).
Nixon et al., Synthetic peptides entrapped in microparticles can elicit cytotoxic T cell activity, Vaccine, 14:1523-30 (1996).
Or et al., Improvements in the minimum binding sequence of C5a: examination of His-67, J. Med. Chem., 35:402-6 (1992).
Partidos et al., CTL responses induced by a single immunization with peptide encapsulated in biodegradable microparticles, J. Immunol. Meth., 206:143-51 (1997).
Reddehase et al., A pentapeptide as minimal antigenic determinant for MHC class I-restricted T lymphocytes, Nature, 337:651-3 (1989).
Rosas et al., Biodegradable PLGA microspheres as a delivery system for malaria synthetic peptide SPf66, Vaccine, 19:4445 (2001).
Sambrook et al., Molecular Cloning: A Laboratory Manual (Second ed., Cold Spring Harbor Laboratory Press, 9.47-9.51 (1989).
Sanderson et al., Immunization to nicotine with a peptide-based vaccine composed of a conformationally biased agonist of C5a as a molecular adjuvant, Int. Immunopharmacol., 3:137-46 (2003).
Sato et al., Therapeutic peptides: technological advances driving peptides into development, Curr. Opin. Biotechnol., 17:638-42 (2006).
Seder et al., T-cell quality in memory and protection: implications for vaccine design, Nat. Rev.Immunol., 8:247-58 (2008).
Siciliano et al., Two-site binding of C5a by its receptor: an alternative binding paradigm for G protein-coupled receptors, Proc. Natl. Acad. Sci USA., 91:1214-8 (1994).
Singh et al., Biodegradable delivery system for a birth control vaccine: immunogenicity studies in rats and monkeys, Pharm. Res., 12:1796-800 (1995).
Stephens-Romero et al., The pathogenesis of fatal outcome in murine pulmonary aspergillosis depends on the neutrophil depletion strategy, Infect. Immun., 73:114-25 (2005).
Stevenson, Advances in peptide pharmaceuticals. Curr. Pharm. Biotechnol., 10:122-37 (2009).
Taylor et al., Development of response-selective agonists of human C5a anaphylatoxin: conformational, biological, and therapeutic considerations, Curr. Med. Chem., 8:675-84 (2001).
Tempero et al., Molecular adjuvant effects of a conformationally biased agonist of human C5a anaphylatoxin, J. Immunol., 158:1377-82 (1996).
Torchilin, Drug targeting, Eur. J. Pharm. Sci., 11 Suppl 2:S81-91 (2000).
Tvinnereim et al., Neutrophil involvement in cross-priming CD8+ T cell responses to bacterial antigens, J. Immunol., 173:1994-2002 (2004).
Ulrich et al., Induction of an antigen-specific CTL response by a conformationally biased agonist of human C5a anaphylatoxin as a molecular adjuvant, J. Immunol., 164:5492-8 (2000).
Van Sorge et al., Anthrax toxins inhibit neutrophil signaling pathways in brain endothelium and contribute to the pathogenesis of meningitis, PLoS One, 3:e2964 (2008).
Vlieghe et al., Synthetic therapeutic peptides: science and market, Drug discovery today, 15:40-56 (2010).
Wang et al., Local injection of thrombin-related peptide (TP508) in PPF/PLGA microparticles-enhanced bone formation during distraction osteogenesis, J. Ortho. Res., 26:539-46 (2008).
Wei et al., Gelatin microspheres encapsulated with a nonpeptide angiogenic agent, ginsenoside Rgl, for Intramyocardial injection in a rat model with infarcted myocardium, J. Cont. Rel., 120:27-34 (2007).
Ye et al., Issues in long-term protein delivery using biodegradable microparticles, J. Control Release, 146:241-60 (2010).
International search report and written opinion from PCT/US2012/67454 dated Apr. 23, 2013.

(56) References Cited

OTHER PUBLICATIONS

Office Action in co-pending U.S. Appl. No. 14/362,040, dated Jul. 9, 2015.
Office Action in co-pending U.S. Appl. No. 14/362,040, dated Nov. 23, 2015.
Office Action in co-pending U.S. Appl. No. 14/362,040, dated Sep. 22, 2016.
Office Action in co-pending U.S. Appl. No. 14/362,040, dated Dec. 28, 2016.
Office Action in co-pending U.S. Appl. No. 14/362,040, dated Jun. 9, 2017.
Office Action in co-pending U.S. Appl. No. 14/362,040, dated Mar. 16, 2018.

* cited by examiner

SEQUENCE LISTING

```
<160> NUMBER OF SEQ ID NOS: 27

<210> SEQ ID NO 1
<211> LENGTH: 74
<212> TYPE: PRT
<213> ORGANISM: Homo sapiens

<400> SEQUENCE: 1

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70

<210> SEQ ID NO 2
<211> LENGTH: 10
<212> TYPE: PRT
<213> ORGANISM: Homo sapiens

<400> SEQUENCE: 2

Ile Ser His Lys Asp Met Gln Leu Gly Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
```

```
<222> LOCATION: (9)..(9)
<223> OTHER INFORMATION: D-Ala

<400> SEQUENCE: 3

Tyr Ser Phe Lys Pro Met Pro Leu Ala Arg
1               5                   10

<210> SEQ ID NO 4
<211> LENGTH: 10
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: N-methyl Leu
<220> FEATURE:
<221> NAME/KEY: MOD_RES
<222> LOCATION: (9)..(9)
<223> OTHER INFORMATION: D-Ala

<400> SEQUENCE: 4

Tyr Ser Phe Lys Asp Met Pro Leu Ala Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-methyl Leu
<220> FEATURE:
<221> NAME/KEY: MOD_RES
<222> LOCATION: (7)..(7)
<223> OTHER INFORMATION: D-Ala

<400> SEQUENCE: 5

Leu Arg Met Tyr Lys Pro Ala Phe Asp Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Tyr, Trp, or a N-acetyl derivatives of
      Tyr or Trp
<220> FEATURE:
<221> NAME/KEY: MOD_RES
<222> LOCATION: (5)..(5)
<223> OTHER INFORMATION: Xaa is Asp, Gly, Pro or a N-methyl derivatives
      of Asp or Gly
<220> FEATURE:
<221> NAME/KEY: MOD_RES
<222> LOCATION: (6)..(6)
<223> OTHER INFORMATION: Xaa is Ala, Cys, Leu, Met or a N-methyl
      derivatives of Ala, Cys, Leu or Met
<220> FEATURE:
<221> NAME/KEY: MOD_RES
<222> LOCATION: (7)..(7)
<223> OTHER INFORMATION: Xaa is Gln, Leu, Pro or a N-methyl derivatives
      of Gln or Leu
<220> FEATURE:
<221> NAME/KEY: MOD_RES
<222> LOCATION: (8)..(8)
<223> OTHER INFORMATION: Xaa is Pro, Leu, alpha-methyl Leu or N-methyl
```

```
            Leu
<220> FEATURE:
<221> NAME/KEY: MOD_RES
<222> LOCATION: (9)..(9)
<223> OTHER INFORMATION: Xaa is D-Ala, Gly, D-Pro, Aib or a N-methyl
      derivatives of D-Ala or Gly
<220> FEATURE:
<221> NAME/KEY: MOD_RES
<222> LOCATION: (10)..(10)
<223> OTHER INFORMATION: Xaa is Arg or N-methyl Arg

<400> SEQUENCE: 6

Xaa Ser Phe Lys Xaa Xaa Xaa Xaa Xaa Xaa
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Ala

<400> SEQUENCE: 7

Tyr Ser Phe Lys Asp Ala Pro Leu Ala Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Ala

<400> SEQUENCE: 8

Tyr Ser Phe Lys Asp Met Pro Leu Ala Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Tyr Ser Phe Lys Asp Met Pro Leu Gly Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Tyr Ser Phe Lys Asp Ala Pro Leu Gly Arg
1               5                   10

<210> SEQ ID NO 11
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 11

Tyr Ser Phe Lys Asp Cys Pro Leu Gly Arg
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Pro

<400> SEQUENCE: 12

Tyr Ser Phe Lys Asp Met Pro Leu Pro Arg
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Ala

<400> SEQUENCE: 13

Tyr Ser Phe Lys Asp Met Gln Leu Ala Arg
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Tyr Ser Phe Lys Asp Met Gln Leu Gly Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Tyr Ser Phe Lys Asp Met Gln Pro Gly Arg
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (9)..(9)
<223> OTHER INFORMATION: Xaa is Aib

<400> SEQUENCE: 16

Tyr Ser Phe Lys Asp Met Pro Leu Xaa Arg
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide

<400> SEQUENCE: 17

Tyr Ser Phe Lys Gly Met Pro Leu Gly Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Tyr Ser Phe Lys Gly Leu Leu Leu Gly Arg
1               5                   10

<210> SEQ ID NO 19
<211> LENGTH: 9
<212> TYPE: PRT
<213> ORGANISM: Mus musculus

<400> SEQUENCE: 19

Ala Tyr Ala Gly Leu Phe Thr Pro Leu
1               5

<210> SEQ ID NO 20
<211> LENGTH: 9
<212> TYPE: PRT
<213> ORGANISM: Mus musculus

<400> SEQUENCE: 20

Tyr Pro His Phe Met Pro Thr Asn Leu
1               5

<210> SEQ ID NO 21
<211> LENGTH: 9
<212> TYPE: PRT
<213> ORGANISM: Homo sapiens

<400> SEQUENCE: 21

Tyr Lys Gln Gly Gly Phe Leu Gly Leu
1               5

<210> SEQ ID NO 22
<211> LENGTH: 20
<212> TYPE: PRT
<213> ORGANISM: Homo sapiens

<400> SEQUENCE: 22

Gly Val Thr Ser Ala Pro Asp Thr Arg Arg Ala Pro Gly Ser Thr Ala
1               5                   10                  15

Pro Pro Ala His
```

```
                    20

<210> SEQ ID NO 23
<211> LENGTH: 19
<212> TYPE: PRT
<213> ORGANISM: Homo sapiens
<220> FEATURE:
<221> NAME/KEY: MISC_FEATURE
<222> LOCATION: (18)..(18)
<223> OTHER INFORMATION: D-Ala

<400> SEQUENCE: 23

Tyr Lys Gln Gly Gly Phe Leu Gly Leu Tyr Ser Phe Lys Pro Met Pro
1               5                   10                  15

Leu Ala Arg

<210> SEQ ID NO 24
<211> LENGTH: 18
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: D-Ala

<400> SEQUENCE: 24

Tyr Ser Phe Lys Pro Met Pro Leu Ala Arg Lys Gln Gly Gly Phe Leu
1               5                   10                  15

Gly Leu

<210> SEQ ID NO 25
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is aminohexanoic acid (AhX)
<220> FEATURE:
<221> NAME/KEY: MISC_FEATURE
<222> LOCATION: (11)..(11)
<223> OTHER INFORMATION: D-Ala

<400> SEQUENCE: 25

Lys Xaa Tyr Ser Phe Lys Pro Met Pro Leu Ala Arg
1               5                   10

<210> SEQ ID NO 26
<211> LENGTH: 20
<212> TYPE: PRT
<213> ORGANISM: Homo sapiens
<220> FEATURE:
<221> NAME/KEY: MISC_FEATURE
<223> OTHER INFORMATION: Kappa-opioid receptor epitope

<400> SEQUENCE: 26

Phe Pro Gly Trp Ala Glu Pro Asp Ser Asn Gly Ser Ala Gly Ser Glu
1               5                   10                  15

Asp Ala Gln Leu
            20

<210> SEQ ID NO 27
<211> LENGTH: 19
<212> TYPE: PRT
<213> ORGANISM: Homo sapiens
```

```
<220> FEATURE:
<221> NAME/KEY: MISC_FEATURE
<223> OTHER INFORMATION: Mu-opioid receptor epitope

<400> SEQUENCE: 27

Gly Asp Leu Ser Asp Pro Cys Gly Asn Arg Thr Asn Leu Gly Gly Arg
1               5                   10                  15

Asp Ser Leu
```

CONTROLLED-RELEASE PEPTIDE COMPOSITIONS AND USES THEREOF

CROSS-REFERENCE TO RELATED APPLICATIONS

This application is a divisional of U.S. Ser. No. 14/362,040, which is the U.S. National Stage of International Patent Application No. PCT/US2012/067454, filed Nov. 30, 2012, which claims the priority benefit of U.S. Provisional Ser. No. 61/566,144, filed Dec. 2, 2011, each of which is incorporated herein by reference in its entirety.

FEDERALLY SPONSORED RESEARCH OR DEVELOPMENT

This invention was made with government support under grant number P20 RR021937 awarded by the National Institutes of Health. The government has certain rights in the invention.

SEQUENCE LISTING

This application contains, as a separate part of the disclosure, a Sequence Listing in computer-readable form, entitled SequenceListing.txt, created Nov. 16, 2012, as 7,901 bytes as an ASCII text file, which is incorporated by reference in its entirety.

FIELD

The disclosure relates to controlled-release formulations for treating and preventing an infection or disease, for stimulating the innate immune system, for directly killing microorganisms, for use as a vaccine in inducing an immune response and for the targeted delivery of compounds such as therapeutics to C5a receptor-bearing cells, e.g., antigen-presenting cells. More specifically, the disclosure relates to the use of controlled-release formulations of micro- and nano-particles containing carboxy-terminal (C-terminal) C5a analogs for the aforementioned methods and uses.

BACKGROUND

Therapeutic peptides (less than or equal to about 50 amino acids in length[1]) and proteins have been developed for a wide range of indications including diabetes, osteoporosis, Crohn's disease, infections (e.g., viral, bacterial, or lower eukaryote such as a fungus or parasite), cancer, cardiovascular disease, immunotherapy, acromegaly, enuresis, and pain[2]. The majority of these indications are for diseases that require systemic administration of the therapeutic peptide or protein to produce a beneficial effect. Although relatively high absolute bioavailabilities can often be achieved through subcutaneous or intramuscular injection, peptides and proteins commonly have a short plasma half-life (minutes to hours)[1, 3, 4 5] and, consequently, a short duration of action. Thus, systemic administration of peptides or proteins requires frequent injections to maintain therapeutic concentrations within the plasma for an extended period of time[3, 5-7].

The blood complement (C) plays an important role in host defense to foreign substances. Individuals that are deficient in certain C components often suffer recurrent and sometimes fatal infections. Activation of the C system results in the production of the anaphylatoxins, C3a and C5a. These fragments are biologically active cleavage products of the larger C proteins C3 and C5, respectively. C5a is a short (74 residues in human) glycoprotein that is generated by enzymatic cleavage of C5.

C5a is recognized as a principal mediator of local and systemic inflammatory responses because of its ability to activate and recruit neutrophils, induce spasmogenesis, increase vascular permeability and stimulate the release of secondary inflammatory mediators from a variety of cell types (e.g., leukocytes and macrophages). C5a also appears to play a role in the modulation of immune response because of its ability to induce, directly or indirectly, the synthesis and release of the cytokines interleukin-1 (IL-1), interleuken-6 (IL-6), interleukin-8 (IL-8), and tumor necrosis factor-α (TNF-α) from human monocytes. These inflammatory and immunomodulatory activities are believed to be expressed via a transmembrane, G-protein-mediated signal transduction mechanism when the C5a ligand interacts with its receptor(s) expressed on the surface of certain circulating and tissue cell types.

The proinflammatory activities of C5a may be classified into two broad categories. The first category of activity is generally associated with the release of histamines and other secondary mediators (e.g., vasoconstrictor and vasodilator eicosanoids). These activities of C5a affect many systems, and are associated with the phenomena of spasmogenesis and certain cell aggregatory activities (e.g., platelet aggregation). The second category of activity involves recruitment and activation of neutrophils and subsequent effects of such neutrophil accumulation and activation, such as increased vascular permeability, release of cytokines and other pro-inflammatory responses. The in vivo pharmacology of these two broad classes of C5a activities is described briefly by Drapeau et al. (1993), Biochem. Pharmacol., 45: 1289-1299. The regulation of neutrophils and other leukocytes by C5a has been reviewed by Hugh & Morgan (1984), Chapter 4 in Regulation of Leukocyte Function, R. Snyderman, ed., Plenum Publishing Corp., pp. 109-153.

Because of its proinflammatory activity, C5a has been implicated as a pathogenic factor in the expression of certain inflammatory disorders, such as rheumatoid arthritis, adult respiratory distress syndrome, gingivitis, and the tissue damage associated with atherosclerosis and myocardial infarction. Consequently, considerable research efforts have been expended in developing specific C5a antagonists for use as anti-inflammatory agents in the treatment of these diseases.

C-terminal C5a peptide analogs have been produced and studied for the purpose of developing C5a agonists and antagonists. For example, Ember et al. (Ember et al. (1992), J. Immunol., 148: 3165-3173) characterized the biological activities of 22 synthetic C-terminal C5a analogs. The analogs were reported to be full agonists of natural C5a, having in vitro activities characteristic of naturally occurring C5a, including the ability to stimulate ileal contraction (i.e., spasmogenesis) platelet aggregatory activation and neutrophil polarization and chemotaxis. However, the potencies of even the most effective of these analogs was on the order of only 0.01-0.25% that of the natural factor. This level of potency could be obtained with analogs as short as decapeptides, as compared with longer C-terminal peptides that had previously been studied as potential agonists. Morgan et al. (1992), J. Immunol., 148: 3937-3942, reported that certain of the peptide analogs disclosed by Ember et al. stimulated synthesis of interleukin-6 in human peripheral blood mononuclear cells. Again, however, potency of these peptide analogs was on the order of 0.01-0.1% of either natural or recombinant C5a. Drapeau et al. (supra) reported on the pharmacology, metabolism and in vivo cardiovascular and hematologic effects of synthetic C-terminal C5a peptide analogs based on either human or porcine amino acid sequences. These analogs were also found to be agonists of natural C5a, but were disclosed as being at least 1,000-fold less potent than recombinant C5a as measured by competition for C5a binding sites.

C-terminal C5a peptide analogs have also been studied with respect to the ability of such analogs to bind to C5a receptors. Kawai et al. (1992), J. Med. Chem., 35: 220-223, reported on relationships between the hydrophobicity and chirality of residues 70-73 of C-terminal octapeptide analogs and the ability of such analogs to bind to C5a receptors. Biological responses elicited by these octapeptide analogs were not reported, however. In other studies, it has been determined that substitution of phenylalanine or tryptophan in positions between 65 and 69 of the human C5a C-terminus could enhance or decrease potency, depending on whether the substitution was made at position 67 or at position 66 (Or et al. (1992) J. Med. Chem. 35: 402-406; Mollison et al. (1991) Agents Actions Suppl. 35:17-21; Siciliano et al. (1994) Proc. Natl. Acad. Sci USA 91:1214-1218). In other studies, these observations were corroborated with reports that substitution of phenylalanine for histidine at position 67 substantially increased the potency of a number of C-terminal peptide analogs of human C5a (Mollison et al. (1991), Agents and Actions, Suppl. 35: 17-21; Or et al. J. Med. Chem., (1992), 35: 402-406; and Kohl et al. (1993), Eur. J. Immunol., 23: 646-652). These reports did not address any differences among the various peptide analogs with respect to their effectiveness for eliciting specific biological responses associated with C5a.

U.S. Pat. No. 5,696,230, which is incorporated by reference in its entirety, describes a conformational characterization of C-terminal peptide analogs of human C5a. U.S. Pat. No. 6,821,517, also incorporated by reference in its entirety, describes compositions and methods for delivering specific antigens to antigen-presenting cells (APCs). Several research articles have published that similarly describe the use of a C-terminal analog of C5a conjugated to a specific antigen (Tempero et al. (1996) J. Immunol. 158:1377-1382; Buchner et al. (1996) J. Immunol. 158:1670-1680; Ulrich et al. (2000) J. Immunol. 164:5492-5498; Sanderson et al. (2003) Int. Immunopharmacol. 3:137-146; Floreani et al. (2007) Cell Cycle 6:2835-2839; Hegde et al. (2008) Int. Immunopharmacol. 8:819-827; Duryee et al. (2009) Vaccine 27:2981-2988; Morgan et al., Vaccine, 28(2): 463-469 (2009); Morgan et al. (2010) Vaccine 28:8275-8279).

To date, the use of oligopeptide C-terminal analogs of C5a, that are not conjugated to a specific antigen, have not been shown to demonstrate therapeutic properties for treating infections and diseases.

Thus, a need exists to develop controlled-release formulations for prophylactic or therapeutic molecules useful in the treatment of infections and diseases, including infections caused by antibiotic resistant bacteria and bacterial burdens due to biofilms. A need further exists to provide a vaccine that will induce an immune response. Additionally, a need exists to target compounds such as antigens to cells bearing C5a receptor, such as antigen-presenting cells.

SUMMARY

The disclosure fulfills at least one of the aforementioned needs in the art by providing controlled-release (e.g., sustained-release) formulations of C-terminal analogs of C5a for treating and/or preventing infections or diseases, for inducing an immune response to a conjugate of the C5a analog and an antigen, and to target antigen-presenting cells (APCs) by associating a C5a analog as a targeting agent with a compound of interest, such as an antigen. For example, selective activation of host innate immunity, which would not only induce the body's inherent first line of defense to infections but would contribute few mutational pressures because the therapeutic effect is neither directed to, nor imposed upon, the infectious bacteria, is contemplated by the disclosure. In various embodiments, selective activation of host immunity is useful for fighting infections and various diseases, in general.

A wide variety of controlled-release formulations comprising a C5a analog are contemplated. For example, a C5a analog is encapsulated in any biocompatible formulation known in the art to prolong the activity of a prophylactic or therapeutic, for example through the controlled release of the prophylactic or therapeutic from the encapsulating material, which may be a microparticle, a nanoparticle, a microgel or any other form of encapsulating material known in the art. As but one set of examples, an effective, clinically proven approach to compensate for a short plasma half-life is through encapsulation in biodegradable microspheres for subcutaneous or intramuscular injection[8-10]. Biodegradable microspheres preferably release peptide or protein from the administration site at a constant rate, resulting in a constant rate of systemic absorption (zero-order rate of absorption). This absorption rate maintains constant therapeutic concentrations of peptide or protein within the plasma over a longer period of time and, consequently, extends the duration of action. Unlike frequent injections of unencapsulated peptide or protein, this approach additionally limits fluctuations in plasma levels of peptide to provide a more uniform therapeutic effect[9]. Encapsulation in biodegradable microspheres can also increase the efficacy of peptides and proteins used for therapeutic applications that require prolonged, local release from the administration site, including immunization[11-18], therapeutic angiogenesis[19, 20] anti-angiogenesis[21, 22], and therapeutic osteogenesis[23]. It can also be an effective approach to target encapsulated therapies to specific cell types within the body[24].

One aspect of the disclosure provides a controlled-release formulation comprising an encapsulating material and a first biologically active agent in the form of an oligopeptide C-terminal C5a analog, the C5a analog having a C5a receptor binding activity. In another aspect, the disclosure provides a controlled-release formulation comprising an encapsulating material and a first biologically active agent in the form of an oligopeptide C-terminal C5a analog, the C5a analog having a C5a receptor binding activity, wherein the C5a analog is attached to the external surface of the encapsulating material. In some embodiments of either aspect, the C5a analog is less than or equal to 20 amino acids, such as 10 amino acids, in length. In certain embodiments of either aspect, the controlled-release formulation comprises an encapsulating material and a C5a analog, wherein the C5a analog comprises the formula: A1-Ser-Phe-Lys-A2-A3-A4-A5-A6-A7 (SEQ ID NO: 6), wherein: A1 is Tyr, Trp, or N-acetyl derivatives of Tyr or Trp; A2 is Asp, Gly, Pro or N-methyl derivatives of Asp or Gly; A3 is Ala, Cys, Leu, Met or N-methyl derivatives of Ala, Cys, Leu or Met; A4 is Gln, Leu, Pro or N-methyl derivatives of Gln or Leu; A5 is Pro, Leu, α-methyl Leu or N-methyl Leu; A6 is D-Ala, Gly, D-Pro, Aib [aminoisobutyric acid (Aib)] or N-methyl derivatives of D-Ala or Gly; and A7 is Arg or N-methyl Arg.

In some embodiments according to either aspect of the disclosure, the controlled-release formulation comprises a C5a analog selected from the group consisting of: (a) Tyr-Ser-Phe-Lys-Asp-Met-Pro-MeL-(D-Ala)-Arg (SEQ ID NO: 4); (b) Tyr-Ser-Phe-Lys-Pro-Met-Pro-Leu-(D-Ala)-Arg (SEQ ID NO: 3); (c) Tyr-Ser-Phe-Lys-Asp-Ala-Pro-Leu-(D-Ala)-Arg (SEQ ID NO: 7); (d) Tyr-Ser-Phe-Lys-Asp-Met-Pro-Leu-(D-Ala)-Arg (SEQ ID NO: 8); (e) Tyr-Ser-Phe-Lys-Asp-Met-Pro-Leu-Gly-Arg (SEQ ID NO: 9); (f) Tyr-Ser-Phe-Lys-Asp-Ala-Pro-Leu-Gly-Arg (SEQ ID NO: 10); (g) Tyr-Ser-Phe-Lys-Asp-Cys-Pro-Leu-Gly-Arg (SEQ ID NO: 11); (h) Tyr-Ser-Phe-Lys-Asp-Met-Pro-Leu-(D-Pro)-Arg (SEQ ID NO: 12); (i) Tyr-Ser-Phe-Lys-Asp-Met-Gln-Leu-(D-Ala)-Arg (SEQ ID NO: 13); (j) Tyr-Ser-Phe-Lys-Asp-Met-Gln-Leu-Gly-Arg (SEQ ID NO: 14); (k) Tyr-Ser-Phe-Lys-Asp-Met-Gln-Pro-Gly-Arg (SEQ ID NO: 15); (l) Tyr-Ser-Phe-Lys-Asp-Met-Pro-Leu-Aib-Arg (SEQ ID NO: 16); (m) Tyr-Ser-Phe-Lys-Gly-Met-Pro-Leu-Gly-Arg (SEQ ID NO: 17); and (n) Tyr-Ser-Phe-Lys-Gly-Leu-Leu-Leu-Gly-Arg (SEQ ID NO: 18). In specific embodiments of the controlled-release formulations, the C5a analog is EP67 bearing the sequence Tyr-Ser-Phe-Lys-Asp-Met-Pro-MeL-(D-Ala)-Arg (SEQ ID NO: 4). Also in some specific embodiments of the controlled-release formulations, the C5a analog is EP54 bearing the sequence Tyr-Ser-Phe-Lys-Pro-Met-Pro-Leu-(D-Ala)-Arg (SEQ ID NO: 3).

Some embodiments according to either of the above aspects of the disclosure further comprise an immunogen. Some of these embodiments provide a controlled-release formulation comprising a C5a analog that is conjugated to an immunogen, such as a peptide. Exemplary peptides contemplated by the disclosure include a peptide immunogen characteristic of a biological entity selected from the group consisting of a diseased cell, an infectious bacterium, an infectious parasite, an infectious fungus, an infectious protozoan, an infectious prion, an infectious virus and a biofilm. An exemplary diseased cell is a cancer cell or tumor cell.

Some embodiments of either controlled-release formulation aspect of the disclosure comprise an encapsulating material that is selected from the group consisting of a polymer-based nanoparticle, a nanogel, a microparticle, a microgel, a microcapsule, a nanocapsule, a polyelectrolyte capsule, a biodegradable lattice, a polysaccharide capsule, a block co-polymer micelle, a polyelectrolyte complex, an injectable implant, a diffusion-controlled hydrogel and a micro-emulsion. For example, in some embodiments, the encapsulating material is selected from the group consisting of a poly (lactic-co-glycolic acid) (PLGA), an ethyl cellulose, a polymethyl methacrylate, a polyethylene glycol, a poly-3-hydroxy butyrate, a starch, an alginate, a collagen, a gelatin, a chitin, a chitosan, a zein, a cross-linked albumin, an azo-cross-linked copolymer of styrene and HEMA-coated particle, a hydrogel, a maleic anhydride and poly (N-isopropylacrylamide) hybrid hydrogel, a hydroxyapatite, a hyaluronic acid, a polysebacic anhydride, a polyester, a polylactide, polyorthoester, a polycarbonate, a polycaprolactone, a polyethylene oxide, a lipid and amino acids. In particular embodiments, the encapsulating material is poly (lactic-co-glycolic acid) (PLGA).

The controlled-release formulations according to the disclosure may control any one or more aspects of the release of a C5a analog or a conjugate comprising a C5a analog. The controlled-release formulation may control the initial burst dosage, may sustain the release for a time period exceeding the period during which C5a administered alone would be detectably functional in binding a C5a receptor, or may control the release such that release is dependent upon a trigger, e.g., a change in pH, temperature or another in vivo mammalian property known to be capable of functioning as a release trigger for at least one encapsulating material as herein defined. In an exemplary embodiment, the controlled-release formulation is capable of providing a sustained release of the C5a analog upon in vivo administration to a mammal as measured by a longer period of detectable C5a binding activity when the formulation is administered than when the C5a analog alone is administered.

In some embodiments of the controlled-release formulations, the C5a analog is attached to the external surface of the encapsulating material. In some embodiments, the controlled release formulations further comprise a second biologically active agent (in addition to the C5a analog as first biologically active agent), such as a therapeutic known in the art.

Another aspect of the disclosure provides a method of treating a mammalian disease comprising administering a therapeutically effective amount of at least one of the above-described controlled-release formulations to a mammal in need of treatment. In some embodiments of the method, the disease is selected from the group consisting of a cancer and an infectious disease, wherein the infectious disease is caused by a bacterium, a parasite, a virus, a fungus, a prion, or a microbial biofilm.

In some embodiments of the method wherein the infectious disease is caused by a bacterium, the bacterium is selected from the group consisting of methicillin-resistant *S. aureus* (MRSA), e.g., MRSA strain USA300-FPR3757, vancomycin-resistant *S. aureus* (VRSA), macrolide-resistant *S. pyogenes*, penicillin-resistant *Streptococcus pneumoniae*, Extensively Drug-Resistant *Mycobacterium tuberculosis* (XDR TB), multidrug-resistant *Enterococcus faecalis*, multidrug-resistant *Enterococcus faecium*, *Pseudomonas aeruginosa*, clindamycin-resistant *Clostridium difficile*, fluoroquinolone-resistant *Clostridium difficile*, *Acinetobacter baumannii*, *Bacillus anthraces*, *Bordetella pertussis*, *Borrelia burgdorferi*, *Brucella abortus*, *Brucella canis*, *Brucella melitensis*, *Brucella suis*, *Campylobacter jejuni*, *Chlamydia pneumonia*, *Chlamydia trachomatis*, *Chlamydophila psittaci*, *Clostridium botulinum*, *Clostridium difficile*, *Clostridium perfringens*, *Clostridium tetani*, *Corynebacterium diphtheriae*, *Enterococcus faecalis*, *Enterococcus faecium*, *Escherichia coli*, *Francisella tularensis*, *Haemophilus influenzae*, *Helicobacter pylori*, *Legionella pneumophila*, *Leptospira interrogans*, *Listeria monocytogenes*, *Mycobacterium leprae*, *Mycobacterium tuberculosis*, *Mycobacterium ulcerans*, *Mycoplasma pneumoniae*, *Neisseria gonorrhoeae*, *Neisseria meningitidis*, *Pseudomonas aeruginosa*, *Rickettsia rickettsia*, *Salmonella typhi*, *Salmonella typhimurium*, *Shigella sonnei*, *Staphylococcus aureus*, *Staphylococcus epidermidis*, *Staphylococcus saprophyticus*, *Streptococcus agalactiae*, *Streptococcus mutans*, *Streptococcus pneumoniae*, *Streptococcus pyogenes*, *Treponema pallidum*, *Vibrio cholerae*, and *Yersinia pestis*.

In some embodiments of the method in which an infection is caused by a virus, the virus is selected from the group consisting of Poxviridae, Chordopoxvirinae, Orthopoxvirus, Cowpoxvirus, Monkeypox virus, Vaccinia virus, Variola virus, Parapoxvirus, Bovine papular stomatitis virus, Orf virus, Pseudocowpox virus, Molluscipoxvirus, Molluscum contagiosum virus, Yatapoxvirus, Tanapox virus, Yaba monkey tumor virus, Herpesviridae, Alphaherpesvirinae, Simplexvirus, Human herpesvirus 1, Herpes simplex virus 1, Human herpesvirus 2, Herpes simplex virus 2, Varicellovirus, Human herpesvirus 3, Varicella-zoster virus, Betaherpesvirinae, Cytomegalovirus, Human herpesvirus 5, Human cytomegalovirus, Roseolovirus, Human herpesvirus 6, Human herpesvirus 7, Gammaherpesvirinae, Lymphocryptovirus, Human herpesvirus 4, Epstein-Barr virus, Rhadinovirus, Human herpesvirus 8, Kaposi's sarcoma-associated herpesvirus, Adenoviridae, Mastadenovirus, Human adenovirus A, Human adenovirus B, Human adenovirus C, Human adenovirus D, Human adenovirus E, Human adenovirus F, Polyomaoviridae, Polyomavirus, BK polyomavirus, Human polyomavirus, JC polyomavirus, Papillomaviridae, Alphapapillomavirus, Human papillomavirus 2, Human papillomavirus 10, Human papillomavirus 6, Human papillomavirus 7, Human papillomavirus 16, Human papillomavirus 18, Human papillomavirus 26, Human papillomavirus 32, Human papillomavirus 34, Human papillomavirus 53, Human papillomavirus 54, Human papillomavirus 61, Human papillomavirus 71, Human papillomavirus cand90, Betapapillomavirus, Human papillomavirus 5, Human papillomavirus 9, Human papillomavirus 49, Human papillomavirus cand92, Human papillomavirus cand96, Gammapapillomavirus, Human papillomavirus 4, Human papillomavirus 48, Human papillomavirus 50, Human papillomavirus 60, Human papillomavirus 88, Mupapillomavirus, Human papillomavirus 1, Human papillomavirus 63, Parvoviridae, Parvovirinae, Erythrovirus, B19 virus, Hepadnaviridae, Orthohepadnavirus, Hepatitis B virus, Retroviridae, Orthoretrovirinae, Deltaretrovirus, Primate T-lymphotropic virus 1, Primate T-lymphotropic virus 2, Lentivirus, Human immunodeficiency virus 1, Human immunodeficiency virus 2, Reoviridae, Orthoreovirus, Mammalian orthoreovirus, Orbivirus, African horse sickness virus, Changuinola virus, Corriparta virus, Orungo virus, Rotavirus, Rotavirus A, Rotavirus B, Mononegavirales, Filoviridae, Marburgvirus, Lake Victoria marburgvirus, Ebolvirus, Ivory Coast ebolavirus, Reston ebolavirus, Sudan ebolavirus, Zaire ebolavirus, Paramyxoviridae, Paramyxovirinae, Respirovirus, Human parainfluenza virus 1, Human parainfluenza virus 3, Morbillivirus, Measles virus, Edmonston virus, Rubulavirus, Human parainfluenza virus 2, Human parainfluenza virus 4, Mumps virus, Henipavirus, Hendravirus, Nipahvirus, Pneumovirinae, Pneumovirus, Human respiratory syncytial virus, Metapneumovirus, Human metapneumovirus, Rhabdoviridae, Vesiculovirus, Chandipura virus, Cocal virus, Isfahan virus, Piry virus, Vesicular stomatitis Alagoas virus, Vesicular stomatitis Indiana virus, Vesicular stomatitis New Jersey virus, Lyssavirus, Australian bat lyssavirus, Rabies virus, Orthomyxoviridae, Influenzavirus A, Influenza A virus, Influenzavirus B, Influenza B virus, Influenzavirus C, Influenza C virus, Bunyaviridae, Bunyavirus, Bunyamwera virus, Bwamba virus, California encephalitis virus, Guama virus, Oriboca virus, Oropouche virus, Hantavirus, Andes virus, Hantaan virus, Puumala virus, Seoul virus, Dobrava-Belgrade virus, Bayou virus, Black Creek Canal virus, New York virus, Sin Nombre virus, Nairovirus, Crimean-Congo hemorrhagic fever virus, Nairobi sheep disease virus, Phlebovirus, Rift Valley fever virus, Sandfly fever Naples virus, Arenaviridae, Arenavirus, Lassa virus, Lymphocytic choriomeningitis virus, Guanarito virus, Junin virus, Machupo virus, Sabiá virus, Deltavirus, Hepatitis delta virus, Nidovirales, Coronaviridae, Coronavirus, Human coronavirus 229E, Human coronavirus OC43, Human enteric coronavirus, Severe acute respiratory syndrome coronavirus, Torovirus, Picornaviridae, Enterovirus, Human enterovirus A, Human enterovirus B, Human enterovirus C, Human enterovirus D, Poliovirus, Rhinovirus, Human rhinovirus A, Human rhinovirus B, Hepatovirus, Hepatitis A virus, Parechovirus, Human parechovirus, Caliciviridae, Norovirus, Norwalk virus, Sapovirus, Sapporo virus, Hepevirus, Hepatitis E virus, Astroviridae, Mamastrovirus, Human astrovirus, Togaviridae, Alphavirus, Chikungunya virus, O'nyong-nyong virus, Mayaro virus, Ross River virus, Barmah Forest virus, Sindbis virus, Ockelbo virus, Venezuelan equine encephalitis virus, Western equine encephalitis virus, Eastern equine encephalitis virus, Rubivirus, Rubella virus, Flaviviridae, Flavivirus, Kyasanur Forest disease virus, Omsk hemorrhagic fever virus, Powassan virus, Louping ill virus, Tick-borne encephalitis virus, Dengue virus, Japanese encephalitis virus, Murray Valley encephalitis virus, St. Louis encephalitis virus, West Nile virus, Ilheus virus, Yellow fever virus, Apoi virus, Hepacivirus, Hepatitis C virus, GB virus B, and GB virus A.

In some embodiments of the method in which an infection is caused by a fungus, the fungus is selected from the group consisting of *C. albicans, A. fumigates, A. flavus, A. clavatus, C. neoformans, C. laurentii, C. albidus, C. gatti, H. capsulatum, P. jirovecii, S. chartarum, C. immitis* and *C. posadasii*. In some embodiments of the method in which an infection is caused by a parasite, the parasite is selected from the group consisting of protozoans, helminthes, parasitic worms, Halzoun syndrome, myiasis, Chogoe fly, human botfly, candiru, bedbug, head louse, body louse, crab louse, demodex, scabies, and screwworm. In some embodiments, the parasite may be a protozoan selected from the group consisting of *Entamoeba histolytica, Giardia lambda, Trichomonas vaginalis, Trypanosoma brucei, T. cruzi, Leishmania donovani, Balantidium coli, Toxoplasma gondii, Plasmodium* Spp. and *Babesia microti*.

In various embodiments of the method according to the disclosure, the disease is selected from the group consisting of scrapie, bovine spongiform encephalopathy, transmissible mink encephalopathy, chronic wasting disease, feline spongiform encephalopathy, exotic ungulate encephalopathy, Creutzfeldt-Jakob disease, iatrogenic Creutzfeldt-Jakob disease, variant Creutzfeldt-Jakob disease, familial Creutzfeldt-Jakob disease, sporadic Creutzfeldt-Jakob disease, Gerstmann-Straussler-Scheinker syndrome, fatal familial insomnia, and Kuru.

In some embodiments of the method according to the disclosure, the formulation being administered further comprises a therapeutic. As used in this context, a therapeutic is any therapeutically active compound or composition known in the art, including any biologically active agent except for any biologically active agent (e.g., a first or a second biologically active agent) expressly described for use in a given embodiment of the method. Thus, when used as a noun, therapeutic is recited to distinguish a compound or composition from a distinct compound or composition identified in that embodiment as a biologically active agent. Also, the disclosure contemplates that, in some embodiments of the method, the C5a analog is administered at a dose of 25 μg to 500 μg.

Another aspect of the disclosure is drawn to a method of targeting a C5a receptor-bearing cell comprising administering a formulation according to claim 1 to a mammal having the cell. In some embodiments of this method, the C5a receptor-bearing cell is an antigen-presenting cell. Also in some embodiments of this method, the C5a receptor-borne by the cell is CD88.

Yet another aspect of the disclosure is directed to use of a controlled-release formulation as described herein to treat a disease selected from the group consisting of a cancer, scrapie, bovine spongiform encephalopathy, transmissible mink encephalopathy, chronic wasting disease, feline spongiform encephalopathy, exotic ungulate encephalopathy, Creutzfeldt-Jakob disease, iatrogenic Creutzfeldt-Jakob disease, variant Creutzfeldt-Jakob disease, familial Creutzfeldt-Jakob disease, sporadic Creutzfeldt-Jakob disease, Gerstmann-Straussler-Scheinker syndrome, fatal familial insomnia, Kuru and an inflammation, wherein the inflammation is caused by a bacterium, a parasite, a virus, a fungus, a prion, or a microbial biofilm.

In another embodiment, a method of activating an immune cell at a site of infection or disease is provided comprising administering an effective amount of a controlled-release formulation comprising an oligopeptide C-terminal analog of C5a to a mammal, the analog having C5a receptor binding activity. An exemplary embodiment is a method of activating an immune cell at a site of infection or disease comprising administering a therapeutically effective amount of a controlled-release formulation as described herein to a mammal in need of treatment.

In various embodiments of the methods according to the disclosure, the controlled-release formulation comprising the C5a analog is administered by a route selected from the group consisting of oral, topical, inhalation spray, intranasal instillation, intradermal, subcutaneous injection, and intravenous injection.

In some embodiments of the methods, the controlled-release formulation comprising the C5a analog is formulated in a powder, aerosol, cream, gel, liquid, bandage, and surgical suture.

In various embodiments of the disclosure, the controlled-release formulation comprising the C5a analog is administered concurrently, prior, or following administration of a therapeutic. The therapeutic, in various embodiments, is selected from the group consisting of vaccine, antibiotic, antifungal, and antiparasitic. In other embodiments, however, these therapeutics are the only therapeutically active compounds or compositions being administered. The controlled-release formulations of the disclosure may separately comprise at least one of these therapeutics and at least one C5a analog. Alternatively, the controlled-release formulations may comprise at least one conjugate of a therapeutic attached to a C5a analog. Accordingly, an exemplary embodiment provides a method of vaccinating a subject comprising administering a prophylactically effective amount of a controlled-release formulation comprising a C5a analog and an immunogen.

In various embodiments of the method involving a vaccine, the vaccine is a C-terminal analog of C5a attached to an immunogen. It is contemplated that a controlled release formulation comprising a vaccine will comprise at least one copy of a C5a analog and at least one copy of an immunogen. In embodiments in which the formulation contains multiple copies of the analog and/or immunogen, the analog and immunogen copies may be arranged in any order, including tandem repeats and interspersion using a repeat unit of one to as many units of the analog, or immunogen, as are found in the molecule.

In various embodiments of the disclosure, the mammal is a human selected from the group consisting of: fetus, newborn, infant, child, young adult, adult, elder, and immunocompromised.

The disclosure further provides a method of treating an influenza infection comprising administering an effective amount of a controlled-release formulation comprising C5a analog EP67 to a mammal.

Another aspect of the disclosure provides a method of treating a dermal S. aureus infection comprising administering an effective amount of a controlled-release formulation comprising C5a analog EP67 to a mammal.

The disclosure also provides a method of treating a Group B Streptococcus (GBS) infection comprising administering an effective amount of a controlled-release formulation comprising C5a analog EP67 to a mammal.

Another aspect of the disclosure provides a method of killing a microbial cell comprising administering an effective amount of a controlled-release formulation comprising C5a analog EP67 to a microbial cell.

Also provided by the disclosure is a method of treating a biofilm comprising administering an effective amount of a controlled-release formulation comprising C5a analog EP67 to a microbial cell.

Another aspect of the disclosure is drawn to controlled-release (e.g., sustained-release) formulations of C-terminal analogs of C5a for vaccine compositions comprising a C-terminal C5a analog conjugated to, i.e., associated with such as by covalent bonding, an immunogen. The controlled-release formulations and C5a analogs are described herein, and the immunogen may be any immunogenic compound or substance that elicits an immune response when conjugated to at least one C5a analog.

Controlled-release formulations comprising APC-targeted immunogens (e.g., activating antigens), which elicit an immune response mediated by an antigen-presenting cell, comprise at least one immunogen functionally linked to at least one targeting moiety that binds specifically to a characteristic determinant on the antigen-presenting cell. The term "functionally linked" is defined generally as a linking of the moieties in such a way that the targeting moiety, e.g., a C5a analog, retains its capacity to bind to a C5a receptor on an antigen-presenting cell and the immunogen retains its ability to elicit a specific immune response under at least one set of conditions standard in the art.

The immunogen can comprise essentially any immunogenic substance, including but not limited to, peptides and proteins, glycopeptides and glycoproteins, phosphopeptides and phosphoproteins, lipopeptides and lipoproteins, carbohydrates, nucleic acids, small molecules and lipids. An APC-targeted immunogen can comprise more than one immunogenic moiety, and/or can comprise more than one targeting moiety. These moieties can be linked in any order (e.g., I-T, T-I, I-T-I-T, T-I-T-I, I-I-T-T, T-T-I-I, and the like, where I is an immunogen and T is a targeting moiety).

Antigen-presenting cells contemplated for targeting according to the present invention include, but are not limited to, monocytes, dendritic cells, macrophages, B cells and some T cells. In embodiments according to the disclosure, the characteristic determinant on the selected APC is a cell surface receptor and the targeting moiety of the APC-targeted antigen is a ligand that binds to the receptor. A suitable cell surface receptor is an immunomodulatory receptor. Suitable cell surface receptors include, but are not limited to, C5a receptors.

A related aspect of the disclosure is a method for delivering an effective amount of at least one specific immunogen to an antigen-presenting cell, and simultaneously delivering signals to that cell that produces a desired immune response. Methods according to this aspect of the disclosure include methods of activating an antigen-presenting cell with a targeting moiety and methods of eliciting an antigen presenting cell-mediated immune response in a subject in which such a response is desired. General methods of immunizing or vaccinating a patient requiring such treatment, methods of treating a disease, such as a tumor disease, and methods for producing antibodies specific for a pre-determined immunogen for use as a research tool or for diagnostic purposes are also contemplated to be within the scope of the present disclosure.

Particular aspects and embodiments of the disclosure are described in the following enumerated paragraphs.

1. A controlled-release formulation comprising an encapsulating material and a first biologically active agent in the form of an oligopeptide C-terminal C5a analog, said C5a analog having a C5a receptor binding activity.

2. A controlled-release formulation comprising an encapsulating material and a first biologically active agent in the form of an oligopeptide C-terminal C5a analog, the C5a analog having a C5a receptor binding activity, wherein the C5a analog is attached to the external surface of the encapsulating material.

3. The formulation according to paragraph 1 or 2 wherein the C5a analog is 10 amino acids in length.

4. The formulation according to paragraph 1 or 2, wherein the C5a analog comprises the formula:

```
                                        (SEQ ID NO: 6)
        A1-Ser-Phe-Lys-A2-A3-A4-A5-A6-A7,
``` wherein:

A1 is Tyr, Trp, or N-acetyl derivatives of Tyr or Trp;

A2 is Asp, Gly, Pro or N-methyl derivatives of Asp or Gly;

A3 is Ala, Cys, Leu, Met or N-methyl derivatives of Ala, Cys, Leu or Met;

A4 is Gln, Leu, Pro or N-methyl derivatives of Gln or Leu;

A5 is Pro, Leu, α-methyl Leu or N-methyl Leu;

A6 is D-Ala, Gly, D-Pro, Aib [aminoisobutyric acid (Aib)] or N-methyl derivatives of D-Ala or Gly; and A7 is Arg or N-methyl Arg.

5. The formulation according to paragraph 4, wherein the C5a analog is selected from the group consisting of:

```
                                        (SEQ ID NO: 4)
        Tyr-Ser-Phe-Lys-Asp-Met-Pro-MeL-(D-Ala)-Arg;

(SEQ ID NO: 3)
        Tyr-Ser-Phe-Lys-Pro-Met-Pro-Leu-(D-Ala)-Arg;

(SEQ ID NO: 7)
        Tyr-Ser-Phe-Lys-Asp-Ala-Pro-Leu-(D-Ala)-Arg;

(SEQ ID NO: 8)
        Tyr-Ser-Phe-Lys-Asp-Met-Pro-Leu-(D-Ala)-Arg;

(SEQ ID NO: 9)
        Tyr-Ser-Phe-Lys-Asp-Met-Pro-Leu-Gly-Arg;

(SEQ ID NO: 10)
        Tyr-Ser-Phe-Lys-Asp-Ala-Pro-Leu-Gly-Arg;

(SEQ ID NO: 11)
        Tyr-Ser-Phe-Lys-Asp-Cys-Pro-Leu-Gly-Arg;

(SEQ ID NO: 12)
        Tyr-Ser-Phe-Lys-Asp-Met-Pro-Leu-(D-Pro)-Arg;

(SEQ ID NO: 13)
        Tyr-Ser-Phe-Lys-Asp-Met-Gln-Leu-(D-Ala)-Arg;

(SEQ ID NO: 14)
        Tyr-Ser-Phe-Lys-Asp-Met-Gln-Leu-Gly-Arg;

(SEQ ID NO: 15)
        Tyr-Ser-Phe-Lys-Asp-Met-Gln-Pro-Gly-Arg;

(SEQ ID NO: 16)
        Tyr-Ser-Phe-Lys-Asp-Met-Pro-Leu-Aib-Arg;

(SEQ ID NO: 17)
        Tyr-Ser-Phe-Lys-Gly-Met-Pro-Leu-Gly-Arg;
        and (SEQ ID NO: 18)
        Tyr-Ser-Phe-Lys-Gly-Leu-Leu-Leu-Gly-Arg.
```

6. The formulation according to paragraph 5, wherein the C5a analog is EP67 bearing the sequence Tyr-Ser-Phe-Lys-Asp-Met-Pro-MeL-(D-Ala)-Arg (SEQ ID NO: 4).

7. The formulation according to paragraph 5, wherein the C5a analog is EP54 bearing the sequence Tyr-Ser-Phe-Lys-Pro-Met-Pro-Leu-(D-Ala)-Arg (SEQ ID NO: 3).

8. The formulation according to paragraph 1 or 2, further comprising an immunogen.

9. The formulation according to paragraph 8, wherein the immunogen is conjugated to the C5a analog.

10. The formulation according to paragraph 8, wherein the immunogen is a peptide.

11. The formulation according to paragraph 8, wherein the peptide immunogen is characteristic of a biological entity selected from the group consisting of a diseased cell, an infectious bacterium, an infectious parasite, an infectious fungus, an infectious protozoan, an infectious prion, an infectious virus and a biofilm.

12. The formulation according to paragraph 11, wherein the diseased cell is a tumor cell.

13. The formulation according to paragraph 1 or 2 wherein the encapsulating material is selected from the group consisting of a polymer-based nanoparticle, a nanogel, a microparticle, a microgel, a microcapsule, a nanocapsule, a polyelectrolyte capsule, a biodegradable lattice, a polysaccharide capsule, a block co-polymer micelle, a polyelectrolyte complex, an injectable implant, a diffusion-controlled hydrogel and a micro-emulsion.

14. The formulation according to paragraph 13 wherein the encapsulating material is selected from the group consisting of a poly (lactic-co-glycolic acid) (PLGA), an ethyl cellulose, a polymethyl methacrylate, a polyethylene glycol, a poly-3-hydroxy butyrate, a starch, an alginate, a collagen, a gelatin, a chitin, a chitosan, a zein, a cross-linked albumin, an azo-cross-linked copolymer of styrene and HEMA-coated particle, a hydrogel, a maleic anhydride and poly (N-isopropylacrylamide) hybrid hydrogel, a hydroxyapatite, a hyaluronic acid, a polysebacic anhydride, a polyester, a polylactide, polyorthoester, a polycarbonate, a polycaprolactone, a polyethylene oxide, a lipid and amino acids.

15. The formulation according to paragraph 14 wherein the encapsulating material is poly (lactic-co-glycolic acid) (PLGA).

16. The formulation according to paragraph 1 or 2, wherein the controlled-release formulation is capable of providing a sustained release of the C5a analog upon in vivo administration to a mammal as measured by a longer period of detectable C5a binding activity when the formulation is administered than when the C5a analog alone is administered.

17. The formulation according to paragraph 1 or 2 further comprising a second biologically active agent.

18. A method of treating a mammalian disease comprising administering a therapeutically effective amount of the controlled-release formulation according to paragraph 1 or 2 to a mammal in need of treatment.

19. The method according to paragraph 18 wherein the disease is selected from the group consisting of a cancer and an infectious disease, wherein the infectious disease is caused by a bacterium, a parasite, a virus, a fungus, a prion, or a microbial biofilm.

20. The method according to paragraph 19 wherein the bacterium is selected from the group consisting of methicillin-resistant *S. aureus* (MRSA), vancomycin-resistant *S. aureus* (VRSA), macrolide-resistant *S. pyogenes*, penicillin-resistant *Streptococcus pneumoniae*, Extensively Drug-Resistant *Mycobacterium tuberculosis* (XDR TB), multidrug-resistant *Enterococcus faecalis*, multidrug-resistant *Enterococcus faecium*, *Pseudomonas aeruginosa*, clindamycin-resistant *Clostridium difficile*, fluoroquinolone-resistant *Clostridium difficile*, *Acinetobacter baumannii*, *Bacillus anthraces*, *Bordetella pertussis*, *Borrelia burgdorferi*, *Brucella abortus*, *Brucella canis*, *Brucella melitensis*, *Brucella suis*, *Campylobacter jejuni*, *Chlamydia pneumonia*, *Chlamydia trachomatis*, *Chlamydophila psittaci*, *Clostridium botulinum*, *Clostridium difficile*, *Clostridium perfringens*, *Clostridium tetani*, *Corynebacterium diphtheriae*, *Enterococcus faecalis*, *Enterococcus faecium*, *Escherichia coli*, *Francisella tularensis*, *Haemophilus influenzae*, *Helicobacter pylori*, *Legionella pneumophila*, *Leptospira interrogans*, *Listeria monocytogenes*, *Mycobacterium leprae*, *Mycobacterium tuberculosis*, *Mycobacterium ulcerans*, *Mycoplasma pneumoniae*, *Neisseria gonorrhoeae*, *Neisseria meningitidis*, *Pseudomonas aeruginosa*, *Rickettsia rickettsii*, *Salmonella typhi*, *Salmonella typhimurium*, *Shigella sonnei*, *Staphylococcus aureus*, *Staphylococcus epidermidis*, *Staphylococcus saprophyticus*, *Streptococcus agalactiae*, *Streptococcus mutans*, *Streptococcus pneumoniae*, *Streptococcus pyogenes*, *Treponema pallidum*, *Vibrio cholerae*, and *Yersinia pestis*.

21. The method according to paragraph 19 wherein the virus is selected from the group consisting of Poxviridae, Chordopoxvirinae, Orthopoxvirus, Cowpoxvirus, Monkeypox virus, Vaccinia virus, Variola virus, Parapoxvirus, Bovine papular stomatitis virus, Orf virus, Pseudocowpox virus, Molluscipoxvirus, Molluscum contagiosum virus, Yatapoxvirus, Tanapox virus, Yaba monkey tumor virus, Herpesviridae, Alphaherpesvirinae, Simplexvirus, Human herpesvirus 1, Herpes simplex virus 1, Human herpesvirus 2, Herpes simplex virus 2, Varicellovirus, Human herpesvirus 3, Varicella-zoster virus, Betaherpesvirinae, Cytomegalovirus, Human herpesvirus 5, Human cytomegalovirus, Roseolovirus, Human herpesvirus 6, Human herpesvirus 7, Gammaherpesvirinae, Lymphocryptovirus, Human herpesvirus 4, Epstein-Barr virus, Rhadinovirus, Human herpesvirus 8, Kaposi's sarcoma-associated herpesvirus, Adenoviridae, Mastadenovirus, Human adenovirus A, Human adenovirus B, Human adenovirus C, Human adenovirus D, Human adenovirus E, Human adenovirus F, Polyomaoma-viridae, Polyomavirus, BK polyomavirus, Human polyomavirus, JC polyomavirus, Papillomaviridae, Alphapapillomavirus, Human papillomavirus 2, Human papillomavirus 10, Human papillomavirus 6, Human papillomavirus 7, Human papillomavirus 16, Human papillomavirus 18, Human papillomavirus 26, Human papillomavirus 32, Human papillomavirus 34, Human papillomavirus 53, Human papillomavirus 54, Human papillomavirus 61, Human papillomavirus 71, Human papillomavirus cand90, Betapapillomavirus, Human papillomavirus 5, Human papillomavirus 9, Human papillomavirus 49, Human papillomavirus cand92, Human papillomavirus cand96, Gammapapillomavirus, Human papillomavirus 4, Human papillomavirus 48, Human papillomavirus 50, Human papillomavirus 60, Human papillomavirus 88, Mupapillomavirus, Human papillomavirus 1, Human papillomavirus 63, Parvoviridae, Parvovirinae, Erythrovirus, B19 virus, Hepadnaviridae, Orthohepadnavirus, Hepatitis B virus, Retroviridae, Orthoretrovirinae, Deltaretrovirus, Primate T-lymphotropic virus 1, Primate T-lymphotropic virus 2, Lentivirus, Human immunodeficiency virus 1, Human immunodeficiency virus 2, Reoviridae, Orthoreovirus, Mammalian orthoreovirus, Orbivirus, African horse sickness virus, Changuinola virus, Corriparta virus, Orungo virus, Rotavirus, Rotavirus A, Rotavirus B, Mononegavirales, Filoviridae, Marburgvirus, Lake Victoria marburgvirus, Ebolvirus, Ivory Coast ebolavirus, Reston ebolavirus, Sudan ebolavirus, Zaire ebolavirus, Paramyxoviridae, Paramyxovirinae, Respirovirus, Human parainfluenza virus 1, Human parainfluenza virus 3, Morbillivirus, Measles virus, Edmonston virus, Rubulavirus, Human parainfluenza virus 2, Human parainfluenza virus 4, Mumps virus, Henipavirus, Hendravirus, Nipahvirus, Pneumovirinae, Pneumovirus, Human respiratory syncytial virus, Metapneumovirus, Human metapneumovirus, Rhabdoviridae, Vesiculovirus, Chandipura virus, Cocal virus, Isfahan virus, Piry virus, Vesicular stomatitis Alagoas virus, Vesicular stomatitis Indiana virus, Vesicular stomatitis New Jersey virus, Lyssavirus, Australian bat lyssavirus, Rabies virus, Orthomyxoviridae, Influenzavirus A, Influenza A virus, Influenzavirus B, Influenza B virus, Influenzavirus C, Influenza C virus, Bunyaviridae, Bunyavirus, Bunyamwera virus, Bwamba virus, California encephalitis virus, Guama virus, Oriboca virus, Oropouche virus, Hantavirus, Andes virus, Hantaan virus, Puumala virus, Seoul virus, Dobrava-Belgrade virus, Bayou virus, Black Creek Canal virus, New York virus, Sin Nombre virus, Nairovirus, Crimean-Congo hemorrhagic fever virus, Nairobi sheep disease virus, Phlebovirus, Rift Valley fever virus, Sandfly fever Naples virus, Arenaviridae, Arenavirus, Lassa virus, Lymphocytic choriomeningitis virus, Guanarito virus, Junin virus, Machupo virus, Sabiá virus, Deltavirus, Hepatitis delta virus, Nidovirales, Coronaviridae, Coronavirus, Human coronavirus 229E, Human coronavirus OC43, Human enteric coronavirus, Severe acute respiratory syndrome coronavirus, Torovirus, Picornaviridae, Enterovirus, Human enterovirus A, Human enterovirus B, Human enterovirus C, Human enterovirus D, Poliovirus, Rhinovirus, Human rhinovirus A, Human rhinovirus B, Hepatovirus, Hepatitis A virus, Parechovirus, Human parechovirus, Caliciviridae, Norovirus, Norwalk virus, Sapovirus, Sapporo virus, Hepevirus, Hepatitis E virus, Astroviridae, Mamastrovirus, Human astrovirus, Togaviridae, Alphavirus, Chikungunya virus, O'nyong-nyong virus, Mayaro virus, Ross River virus, Barmah Forest virus, Sindbis virus, Ockelbo virus, Venezuelan equine encephalitis virus, Western equine encephalitis virus, Eastern equine encephalitis virus, Rubivirus, Rubella virus, Flaviviridae, Flavivirus, Kyasanur Forest disease virus, Omsk hemorrhagic fever virus, Powassan virus, Louping ill virus, Tick-borne encephalitis virus, Dengue virus, Japanese encephalitis virus, Murray Valley encephalitis virus, St. Louis encephalitis virus, West Nile virus, Ilheus virus, Yellow fever virus, Apoi virus, Hepacivirus, Hepatitis C virus, GB virus B, and GB virus A.

22. The method according to paragraph 19 wherein the fungus is selected from the group consisting of *C. albicans*, *A. fumigates*, *A. flavus*, *A. clavatus*, *C. neoformans*, *C. laurentii*, *C. albidus*, *C. gatti*, *H. capsulatum*, *P. jirovecii*, *S. chartarum*, *C. immitis* and *C. posadasii*.

23. The method according to paragraph 19 wherein the parasite is selected from the group consisting of protozoans, helminthes, parasitic worms, Halzoun syndrome, myiasis, Chogoe fly, human botfly, candiru, bedbug, head louse, body louse, crab louse, demodex, scabies, and screwworm.

24. The method according to paragraph 19 wherein the parasite is a protozoan selected from the group consisting of *Entamoeba histolytica, Giardia lambila, Trichomonas vaginalis, Trypanosoma brucei, T. cruzi, Leishmania donovani, Balantidium coli, Toxoplasma gondii, Plasmodium* Spp. and *Babesia microti*.

25. The method according to paragraph 18 wherein the disease is selected from the group consisting of scrapie, bovine spongiform encephalopathy, transmissible mink encephalopathy, chronic wasting disease, feline spongiform encephalopathy, exotic ungulate encephalopathy, Creutzfeldt-Jakob disease, iatrogenic Creutzfeldt-Jakob disease, variant Creutzfeldt-Jakob disease, familial Creutzfeldt-Jakob disease, sporadic Creutzfeldt-Jakob disease, Gerstmann-Straussler-Scheinker syndrome, fatal familial insomnia, and Kuru.

26. The method according to paragraph 18 wherein the formulation being administered further comprises a therapeutic.

27. The method according to any one of paragraphs 18-26 wherein the C5a analog is administered at a dose of 25 µg to 500 µg.

28. A method of targeting a C5a receptor-bearing cell comprising administering a formulation according to paragraph 1 or 2 to a mammal having the cell.

29. The method according to paragraph 28, wherein the C5a receptor-bearing cell is an antigen-presenting cell.

30. Use of a formulation according to paragraph 1 or 2 to treat a disease selected from the group consisting of a cancer, scrapie, bovine spongiform encephalopathy, transmissible mink encephalopathy, chronic wasting disease, feline spongiform encephalopathy, exotic ungulate encephalopathy, Creutzfeldt-Jakob disease, iatrogenic Creutzfeldt-Jakob disease, variant Creutzfeldt-Jakob disease, familial Creutzfeldt-Jakob disease, sporadic Creutzfeldt-Jakob disease, Gerstmann-Straussler-Scheinker syndrome, fatal familial insomnia, Kuru and an inflammation, wherein the inflammation is caused by a bacterium, a parasite, a virus, a fungus, a prion, or a microbial biofilm.

31. A method of activating an immune cell at a site of infection or disease comprising administering a therapeutically effective amount of a controlled-release formulation according to paragraph 1 or 2 to a mammal in need of treatment.

32. A method of vaccinating a subject comprising administering a prophylactically effective amount of a controlled-release formulation comprising a C5a analog and an immunogen.

Other features and advantages of the disclosure will be better understood by reference to the following detailed description, including the drawing and the examples.

DETAILED DESCRIPTION

Figure 1:
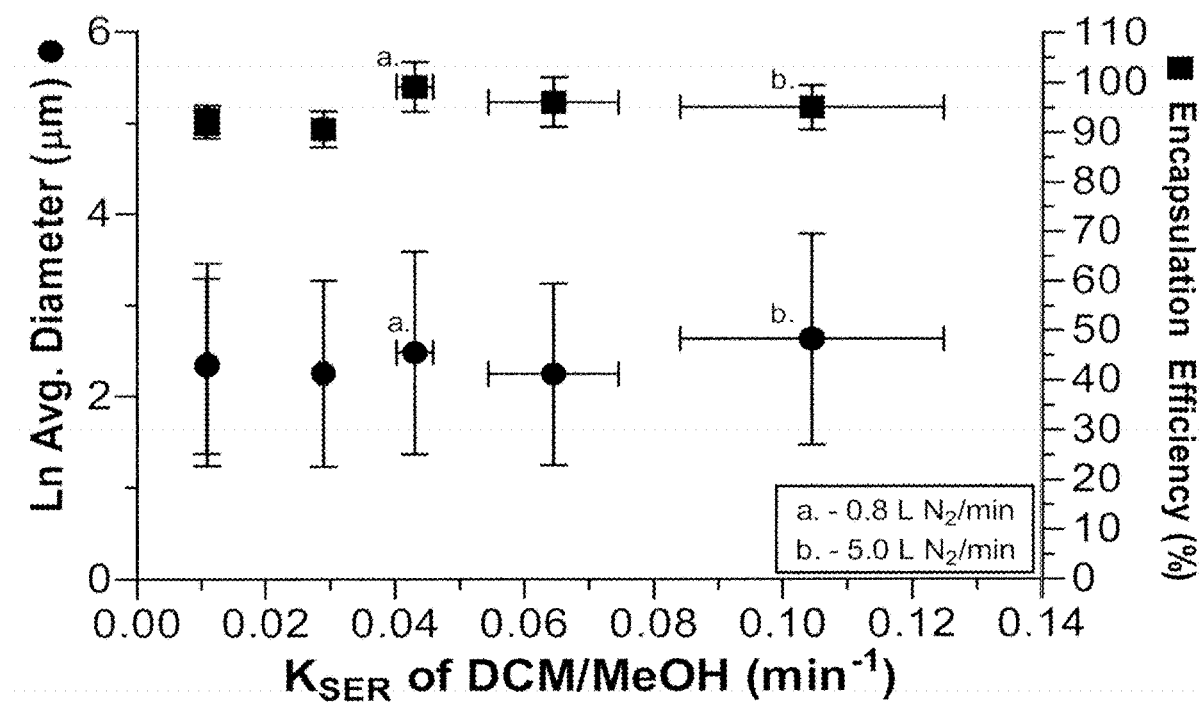
FIG. 1. Relationship between solvent evaporation rate during microsphere hardening and subsequent microsphere diameter and peptide encapsulation efficiency. The solvent evaporation rate of DCM/MeOH from the final O/W emulsion was controlled by stirring rate or flow rate of N2 over the emulsion surface at the lowest stirring rate (150 RMP) and calculated by a direct first-order fit as described in FIG. 2. The distribution of microsphere diameters was determined by an Auto T4 cell counter optimized to count spherical particles and converted to a normal distribution by natural logarithm transform and compared by one way ANOVA with Tukey's post-test.

A variety of diseases and/or infections can be treated and/or prevented by administering controlled-release formulations of C-terminal analogs of C5a. In an embodiment of one aspect of the disclosure, diseases caused by airborne pathogens are treated and/or prevented by administering C-terminal analogs of C5a. Currently, no effective method exists for enhancing airway immune responsiveness to airborne pathogens. In another aspect, the controlled-release formulation comprises a C5a analog of the disclosure joined, typically by covalent fusion, to an immunogen to form a vaccine useful in inducing an immune response to prevent or treat disease. In yet another aspect of the disclosure, a controlled-release formulation comprises a C5a analog that is associated with a prophylactic or a therapeutic compound, with the C5a analog acting as a targeting agent to deliver the compound to cells bearing C5a receptors, such as antigen-presenting cells (APCs). In this aspect, the C5a analog association with the compound may be direct, such as by covalent or non-covalent linkage of analog and compound, or the association may be indirect, such as by independently associating a controlled-release material with each of an analog and a compound. For example, a C5a analog of the disclosure may be covalently or non-covalently associated with poly (lactic-co-glycolic acid) (PLGA) as a controlled-release material, with the PLGA forming a micro- or nano-particle and the C5a analog disposed on the surface of the particle. The prophylactic or therapeutic compound may be encapsulated within the particle, providing indirect association of the compound and analog.

In one embodiment, the disclosure provides effective protection against airborne pathogens by the intranasal administration of a C-terminal analog of C5a (such as EP67 described herein). Unlike conventional vaccines, C-terminal analog of C5a can be generated economically and rapidly in huge quantities by standard solid-phase peptide synthesis, purified to 100% purity, and stored as a dry lyophilized powder which has a shelf life of years at room temperature. Moreover, in another embodiment, administration of C-terminal analogs of C5a has the advantage of inducing airway immune protection to any type of airborne pathogen, thus providing a level of protection allowing a window of time for the administration of pathogen-specific vaccines. As disclosed herein, C-terminal analogs of C5a not only heighten airway immunity prior to pathogen exposure, but can activate airway immunity and, consequently, decrease recovery time after pathogen exposure. In other words, C-terminal analogs of C5a induce both prophylactic and therapeutic mucosal (airway) immune responses.

In another embodiment of the disclosure, the ability to complement C-terminal analogs of C5a-mediated therapy, for example, with existing antivirals (e.g., Tamiflu™), existing vaccines, and also C-terminal analogs of C5a-containing vaccines to influenza (e.g., EP67 conjugated to an influenza-derived antigen/epitope) is provided. Such C-terminal analogs of C5a-containing vaccines are generated by the covalent attachment of C-terminal analogs of C5a to the intact influenza virus, proteins from the interior and/or the surface of the virus, or epitopes derived from these proteins.

Given the ability of C-terminal analogs of C5a to induce general immune responsiveness, the administration of C-terminal analogs of C5a also heightens immunologic surveillance to other diseases such as cancer and, in similar fashion, provides a window of time to allow the administration of patient-specific vaccines, including C-terminal analogs of C5a-containing cancer vaccines.

In yet another embodiment of the disclosure, bacterial infections are treated and/or prevented by administering C-terminal analogs of C5a. The prevalence of bacterial infections along with the emergence of antibiotic-resistant bacteria, such as methicillin-resistant *S. aureus* (MRSA) have complicated the treatment and control of these infections in the United States and Third World countries. The pace by which these bacteria can mutate and evade standard antibiotic treatment exceeds the pace of development of new antibiotics to fight them. The disclosure provides materials and methods for the use of a C-terminal analog of C5a as a way of activating the innate arm of immunity to fight these bacterial infections. This is achieved by a simple subcutaneous injection or topical application (or, in various embodiments, administration by one or more means described below) of a C-terminal analog of C5a. As discussed herein, C-terminal analogs of C5a invoke localized and/or systemic innate immune responses that recruit/activate the necessary immune cells to the infection site such that it is eliminated/reduced. Considering the aforementioned ability to produce large, highly pure and stable quantities of C-terminal analogs of C5a, distribution to remote field clinics/hospitals and combat areas and its subsequence storage and stability once delivered to these areas is simple and requires no expensive storage facilities/equipment such as refrigerators.

In still another embodiment of the disclosure, a C-terminal analog of C5a is used to treat, e.g., antibiotic-resistant bacteria or difficult-to-treat fungal and viral infections by directly interacting with the pathogen as described herein. Of course, in addition to this direct effect, C-terminal analogs of C5a invoke innate immunity against the bacteria as described herein and, consequently, afford a dual mechanism of action not realized by standard antibiotics or other antibacterial peptides.

In yet another embodiment, a C-terminal analog of C5a is used to therapeutically and/or prophylactically reduce bacterial burdens in biofilms associated with catheters and other artificial implants. Bacteria within a biofilm are not responsive to conventional antibiotic treatment since they are physically protected from access to the antibiotics by the biofilm matrix. More importantly, the bacteria within a biofilm have assumed a sessile state and are refractory to antibiotics, which typically target the cell wall and ribosomal components of active/growing bacteria. Likewise, bacteria are protected from the cellular and molecular components of host immunity making immunotherapy/vaccines problematic. Indeed, the various components of the biofilm matrix appear to have an immunosuppressive effect on the cellular components of immunity (particularly macrophages) in the vicinity of the biofilm. As a result, the only option for dealing with biofilms developing around an artificial device is a cycle of removal and replacement—an inconvenient, ineffective and undesirable process. These difficulties of biofilm treatment/control are underscored even further when it is associated with more permanent artificial implants such as hips, knees and heart valves. In addition, this issue becomes even more pronounced against the backdrop of the rapidly increasing population of the elderly who will be the primary recipients of such artificial implants and who grow increasingly less immunosuppressive with age.

Thus, in one embodiment, the use of a C-terminal analog of C5a overcomes the aforementioned issues of biofilm treatment and control. As described herein, C-terminal analogs of C5a provide the activation signals to C5a receptor-bearing macrophages (and other APCs) to mount a robust innate immune response to the bacteria in a biofilm and surrounding tissues. Treatment with a C-terminal analog of C5a is among the first such approaches to have shown a therapeutically viable method for controlling bacterial burden in a biofilm.

Another aspect of the disclosure takes advantage of the fact that APCs, including dendritic cells, monocytes, macrophages and B cells, possess functional receptors for numerous molecules that modulate the immune response. Compounds (e.g., ligands) that bind to these receptors can be conjugated to weakly immunogenic antigens, for example, as a way of delivering antigens to the antigen-presenting pathway of the APC and simultaneously activating the antigen-presenting capacity of the APC. These conjugates bind to a receptor on the APC surface, transduce a biological signal, and are internalized by the APC. The antigenic moiety of the conjugate is thereby delivered to the antigen-presenting pathway of the APC along with simultaneous activation of the APC. See U.S. Pat. No. 7,358,087, incorporated herein by reference in its entirety. In accordance with the disclosure, a controlled-release formulation comprising such a conjugate is contemplated as particularly well-suited for eliciting immune responses to relatively weak unconjugated antigenic compounds.

These antigenic moiety-targeting moiety conjugates are sometimes referred to herein as "molecular adjuvants" or "APC-targeted activating antigens." The controlled-release formulations of APC-targeted activating antigens are designed to elicit immune responses mediated by one or more types of antigen presenting cells. Accordingly, in some embodiments of the disclosure, an APC-targeted activating antigen (i.e., conjugate) contained within a controlled-release formulation comprises at least one antigenic moiety linked to a targeting and activating moiety that binds specifically to at least one characteristic determinant on the selected antigen presenting cell type. Without wishing to be bound by theory, this binding is expected to be followed by internalization of the APC-targeted antigen and to result in presentation of the antigen moiety on the surface of the APC. An "antigenic moiety" of the disclosure is any substance that is capable of eliciting a specific immune response under at least one set of conditions. The selected antigenic moiety may or may not be capable of eliciting an immune response by conventional means.

Exemplary compositions have been synthesized, and have been shown to elicit APC-mediated immune responses that are consistent with the above-described mechanism. For example, antigenic epitopes have been conjugated to the amino-terminal end of a C5a decapeptide agonist capable of binding to C5a receptors present on the surface of many APCs. Mice that were inoculated with an epitope of human MUC1 (a cell surface-associated mucin) conjugated to such a C5a agonist exhibited pronounced antibody titers against the MUC1 epitope, including high titers of specific antibodies with isotypes IgG2a and IgG2b. Mice failing to exhibit a significant specific immune response were inoculated with (1) MUC1 epitope alone, (2) C5a agonist alone, (3) unconjugated MUC1 epitope and C5a agonist together, or (4) C5a agonist conjugated to MUC1 epitope in a manner in which the biological activity of the C5a moiety was blocked. These results are described in greater detail in Example 8. Similar results were observed with conjugates of C5a agonist to a 12 kDa polypeptide, i.e., serum amyloid A (SAA), as described in greater detail in Example 9. These data demonstrate the feasibility of using these conjugates to deliver antigens to APCs, with the simultaneous activation of APCs by the targeting (e.g., ligand) moiety.

General Definitions

Unless otherwise defined herein, scientific and technical terminologies employed in the disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Thus, for example, the reference to a particular C-terminal analog of C5a is a reference to one such analog or a plurality of such analogs, including equivalents thereof. Also, the terms "at least one" and "one or more" have the same meaning and include one, two, three or more. The following terms, unless otherwise indicated, shall be understood to have the following meanings when used in the context of the disclosure.

Examples provided herein, including those following "such as" and "e.g.," are considered as illustrative only of various aspects of the disclosure and embodiments thereof, without being specifically limited thereto. Any suitable equivalents, alternatives, and modifications thereof (including materials, substances, constructions, compositions, formulations, means, methods, conditions, etc.) known and/or available to one skilled in the art may be used or carried out in place of or in combination with those disclosed herein, and are considered to fall within the scope of the disclosure.

As used in the disclosure, the term "treating" or "treatment" refers to an intervention performed with the intention of preventing the further development or altering the pathology of a disease or infection. "Treatment" or "treating" typically refers to therapeutic intervention in an existing disease process, but these terms may also refer to both therapeutic and prophylactic or preventative intervention, as would be clear from context. "Preventing" refers to a preventative measure taken with a subject not previously exposed or infected with a particular pathogen. A therapeutic agent may directly decrease the pathology of a disease or infection, or render the disease or infection more susceptible to treatment by other therapeutic agents or, for example, the host's immune system. Treatment of patients suffering from clinical, biochemical, radiological or subjective symptoms of a disease or infection may include alleviating some or all of such symptoms or reducing the predisposition to the disease. Improvement after treatment may be manifested as a decrease or elimination of such symptoms.

"Infections" as used herein refers to any microbial invasion of a living tissue that is deleterious to the organism (host). Microbial infections may be caused by microorganisms, or "infectious agents," including, but not limited to, a bacteria, virus, fungus, parasite, protozoan, and prion. Similarly, the term "disease" refers to any pathological condition and includes the overt presentation of symptoms (i.e., illness) or the manifestation of abnormal clinical indicators (e.g., biochemical indicators). Alternatively, the term "disease" refers to a genetic or environmental risk of or propensity for developing such symptoms or abnormal clinical indicators. An infection or disease is any condition that would benefit from treatment with a material or product according to the disclosure. This includes chronic and acute disorders or diseases including those pathological conditions which predispose the mammal to the disorder in question. In various embodiments of the invention, cancer cells (e.g., a cell that grows and/or divides at an unregulated, quickened pace) or other transformed cells (e.g., a cell that has been genetically changed by a virus to a tumor cell) are contemplated.

As used herein, the phrase "effective amount" or "therapeutically effective amount" is meant to refer to an amount of therapeutic or prophylactic C-terminal analog of C5a that would be appropriate for an embodiment of the disclosure, that will elicit the desired therapeutic or prophylactic effect or response, including alleviating some or all of such symptoms of disease or infection or reducing the predisposition to the disease or infection, when administered in accordance with the desired treatment regimen.

The term "oligopeptide" refers to a peptide that is at least about 5 amino acids in length; for example at least 10 amino acids in length; for example at least about 20 amino acids in length; or at least about 50 amino acids in length. In one embodiment of the disclosure, the oligopeptide is a decapeptide (i.e., 10 amino acids in length).

As used herein, the term "carboxy-terminal" or "C-terminal" refers to the carboxy-terminus of C5a.

As used herein "biologically active derivative," "biologically active fragment," "biologically active analog" or "biologically active variant" includes any derivative or fragment or analog or variant of a molecule having substantially the same functional and/or biological properties of the molecule, such as binding properties, and/or the same structural basis, such as a peptidic backbone or a basic polymeric unit.

An "analog," such as a "variant" or a "derivative," is a compound substantially similar in structure and having the same biological activity, albeit in certain instances to a differing degree, to a naturally occurring molecule.

A "derivative," for example, is a type of analog and refers to a peptide or oligopeptide sharing the same or substantially similar structure as a reference polypeptide that has been modified, e.g., chemically.

The phrase "not attached to an antigen" refers to a C-terminal analog of C5a that is not associated or attached (linked or conjugated; e.g., via a peptide bond) to an antigen for the purpose of stimulating a specific immune response against that antigen. Of course, the phrase "attached to an antigen" refers to a C-terminal analog of C5a that is associated or attached (linked or conjugated; e.g., via a peptide bond) to an antigen for the purpose of stimulating a specific immune response against that antigen.

The phrase "having C5a receptor binding activity" refers to the ability of a C-terminal C5a analog to bind to CD88. According to the disclosure, the binding of a C-terminal C5a analog to CD88 causes one or more biological activities or responses, including but not limited to, activation of antigen presenting cells (APCs).

"Concurrent" administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks. "Prior" administration refers to administering a C-terminal analog of C5a at some time before administering a second therapeutic agent, irrespective of whether the two therapeutic agents are exerting a therapeutic effect together. Moreover, "following" administration refers to administering a C-terminal analog of C5a at some time after administering a second therapeutic agent, irrespective of whether the two therapeutic agents are exerting a therapeutic effect together.

"Mammal" for purposes of treatment and prevention refers to any animal classified as a mammal, including humans, domestic and farm animals, and zoo, sports, or pet animals, such as dogs, horses, cats, cows, and the like. In one embodiment, the mammal is a human.

The following terms refer to a mammal according to the following age ranges: fetus (about 9 weeks after fertilization to birth), newborn (birth to about 28 days, including premature, post-mature and full-term newborns), infant (about 1 month to about 12 months), child (about 1 year to about 13 years, including, e.g., toddlers, pre-teenagers and early teenagers), young adult (from about 13 years to 18 years), adult (from about 18 years to about 65 years), and elder (from about 65 years until death).

As used herein, the term "immunocompromised" refers to a subject, e.g., a human, who is in a state in which the immune system's ability to fight an infection or disease is compromised or entirely absent. In one embodiment of the disclosure, an aged or elderly subject, although not immunodeficient, may be immunocompromised in having a reduced capacity to generate an immune response to, for example, a pathogen.

A "biofilm" as used herein refers to an aggregate of microorganisms in which cells adhere to each other on a surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces, e.g., on catheters or other artificial implants. An "implant" or artificial implant" is a medical device manufactured to replace a missing biological structure, support a damaged biological structure, or enhance an existing biological structure. Exemplary artificial implants include catheters, artificial hips, knees heart valves, and dental implants, which may comprise pins, rods, screw and plates.

C5a Analogs

C5a is a protein fragment released from complement component C5. In humans, the polypeptide contains 74 amino acids (SEQ ID NO: 1). In one embodiment of the disclosure, the C-terminus of C5a comprises amino acids 65-74 of C5a (i.e., ISHKDMQLGR ("$C5_{\alpha 65\text{-}74}$") (SEQ ID NO: 2). The disclosure further provides a C5a analog comprising 1, 2, 3, 4, or 5 amino acid substitutions in the amino acid set out in SEQ ID NO: 2 wherein the peptide having the substituted amino acid sequence retains binding activity of the peptide set out in SEQ ID NO: 2.

The C-terminal analog of C5a EP54 (YSFKPMPLaR; SEQ ID NO: 3) (uppercase letters designate the L stereoisomeric form and lower case the D stereoisomeric form of the amino acids) has been described previously (Duryee et al. (2009) Vaccine 27:2981-2988; Hegde et al. (2008) Int. Immunopharmacol. 8:819-827; and Ulrich et al. (2000) J. Immunol. 164:5492-5498). However, these studies described an EP54 construct wherein EP54 was conjugated to a specific antigen or hapten. The disclosure further provides a C5a analog comprising 1, 2, 3, 4, or 5 amino acid substitutions in the amino acid sequence set out in SEQ ID NO: 3 wherein the peptide having the substituted amino acid sequence retains binding activity of the peptide set out in SEQ ID NO: 3.

EP67 was derived from the C-terminal region of human complement component, C5a (Taylor S M, et al., Curr Med Chem 2001; 8:675-684.). EP67, YSFKDMP(MeL)aR (SEQ ID NO: 4; "(MeL)" is N-methyl leucine), possesses potent immune-enhancing properties (Morgan et al., Vaccine, 28(2): 463-469 (2009). The disclosure further provides a C5a analog comprising 1, 2, 3, 4, or 5 amino acid substitutions in the amino acid sequence set out in SEQ ID NO: 4 wherein the peptide having the substituted amino acid sequence retains binding activity of the peptide set out in SEQ ID NO: 4.

Additional analogs are described, for example, in U.S. Pat. Nos. 5,696,230 and 6,821,517. U.S. Pat. No. 5,696,230 describes C-terminal peptide analogs of C5a whose naturally flexible structure has been modified to constrain the peptides to specific conformations. These analogs are not only many-fold more potent than previously described peptide analogs, they also exhibit the ability to selectively stimulate different classes of biological responses associated with C5a.

The disclosure further relates to screening assays to identify C-terminal analogs of C5a, and the use of the analogs to treat or prevent infections or diseases as described herein. Binding activity of C-terminal analogs of C5a to CD88 is measured using standard techniques known in the art (see, e.g., U.S. Pat. No. 5,696,230). In various embodiments, C-terminal analogs of C5a of the disclosure compete with naturally occurring C5a or the C-terminus thereof for binding CD88 by more than 15%, more than 20%, more than 30%, more than 40%, more than 50%, more than 60%, more than 70%, more than 80%, or more than 90%.

In one aspect, the starting material of the disclosure is a protein, oligopeptide or peptide. Contemplated oligopeptide molecules include biologically active fragments of a full-length protein (e.g., a C-terminal fragment of C5a) as well as biologically active analogs, derivatives, and variants of such oligopeptides. Thus, oligopeptides of the disclosure include those that (1) have an amino acid sequence that has greater than about 60%, about 65%, about 70%, about 75%, about 80%, about 85%, about 90%, about 91%, about 92%, about 93%, about 94%, about 95%, about 96%, about 97%, about 98% or about 99% or greater amino acid sequence identity, over a region of at least about 5, about 6, about 7, about 8, about 9, about 10, about 11, about 12, about 13, about 14, about 15, or about 20 or more amino acids, to an oligopeptide encoded by a referenced nucleic acid or an amino acid sequence described herein (e.g., $C5a_{65-74}$ or an oligopeptide C-terminal analog of C5a as provided herein), an immunogenic fragment thereof, and/or a conservatively modified analog, derivative, or variant thereof.

An oligopeptide or peptide variant, for example, is a type of analog and refers to an oligopeptide or peptide sharing substantially similar structure and having the same biological activity as a reference oligopeptide or peptide or protein (i.e., "native oligopeptide or peptide" or "native therapeutic protein"). Variants differ in the composition of their amino acid sequences compared to the naturally occurring or reference oligopeptide or peptide from which the variant is derived, based on one or more mutations involving (i) deletion of one or more amino acid residues at one or more termini of the oligopeptide or peptide and/or one or more internal regions of the naturally occurring or reference oligopeptide or peptide sequence (e.g., fragments), (ii) insertion or addition of one or more amino acids at one or more termini (typically an "addition" or "fusion") of the oligopeptide or peptide and/or one or more internal regions (typically an "insertion") of the naturally occurring or reference oligopeptide or peptide sequence or (iii) substitution of one or more amino acids for other amino acids in the naturally occurring or reference oligopeptide or peptide.

Variant oligopeptides or peptides include insertion variants, wherein one or more amino acid residues are added to a reference amino acid sequence of the disclosure. Insertions may be located at either or both termini of the oligopeptide or peptide, and/or may be positioned within internal regions of the reference amino acid sequence. Insertion variants, with additional residues at either or both termini, include for example, fusion oligopeptides or peptides and oligopeptides or peptides including amino acid tags or other amino acid labels. In some embodiments, the oligopeptide or peptide molecule optionally contains an N-terminal Met, especially when the molecule is expressed recombinantly in a bacterial cell such as *E. coli*.

In deletion variants, one or more amino acid residues in a reference amino acid sequence as described herein are removed. Deletions can be effected at one or both termini of the oligopeptide or peptide, and/or with removal of one or more residues within the reference amino acid sequence. Deletion variants, therefore, include fragments of a reference amino acid sequence.

In substitution variants, one or more amino acid residues of a reference amino acid sequence are removed and replaced with alternative residues. In some embodiments, the substitutions are conservative in nature and conservative substitutions of this type are well known in the art. The disclosure also embraces substitutions that are non-conservative. Exemplary conservative substitutions are described in Lehninger, [Biochemistry, 2nd Edition; Worth Publishers, Inc., New York (1975), pp. 71-77] and are set out immediately below.

| CONSERVATIVE SUBSTITUTIONS | |
|---|---|
| SIDE CHAIN CHARACTERISTIC | AMINO ACID |
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

| CONSERVATIVE SUBSTITUTIONS II | |
|---|---|
| ORIGINAL RESIDUE | EXEMPLARY SUBSTITUTION |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

As described herein, in various embodiments, the oligopeptide is modified to introduce amino acid homologs or amino acid derivatives. By way of example, in various embodiments of the disclosure, conformationally biased, response-selective oligopeptide C-terminal analogs of C5a are produced by the inclusion of amino acid homologs (e.g., to restrict backbone flexibility in order to bias features of peptide topography). Such amino acid homologs include, but are not limited to, D stereoisomeric forms of amino acids, Pro, N-methyl amino acids, phospho amino acids, and intramolecular cyclizations, including, for example and without limitation, side-chain-to-side chain, side-chain-to-backbone, and head-to-tail cyclizations.

Oligopeptide modifications may be accomplished using standard molecular biological techniques known in the art and can be accomplished recombinantly (e.g., engineering an amino acid sequence) such that the purified, modified oligopeptides comprise the desired sequence. Alternatively, such modification may be accomplished in vitro following or during the production and purification of the oligopeptide. For example, oligopeptide C-terminal analogs of C5a of the disclosure may be prepared by various synthetic methods of peptide synthesis via condensation of one or more amino acid residues, in accordance with conventional peptide synthesis methods. Oligopeptide are synthesized according to standard solid-phase methodologies, such as may be performed on an Applied Biosystems Model 430A peptide synthesizer (Applied Biosystems, Foster City, Calif.) or AAPPTEC Apex Model 396 synthesizer, according to manufacturer's instructions. Other methods of synthesizing peptides, oligopeptides or peptidomimetics, either by solid-phase methodologies or in liquid phase, are well known to those skilled in the art and are contemplated herein. When solid-phase synthesis is utilized, the C-terminal amino acid is linked to an insoluble carrier that can produce a detachable bond by reacting with a carboxyl group of a C-terminal amino acid. One preferred insoluble carrier is p-hydroxymethylphenoxymethyl polystyrene (HMP) resin. Other useful resins include, but are not limited to, phenylacetamidomethyl (PAM) resins for synthesis of some N-methyl-containing peptides (this resin is used with the Boc method of solid-phase synthesis; and MBHA (p-methylbenzhydrylamine) resins for producing peptides having C-terminal amide groups, and Wang resins for utilization in Fmoc-based chemistries.

During the course of oligopeptide synthesis, branched chain amino and carboxyl groups may be protected/deprotected as needed, using commonly known protecting groups. In one embodiment, N$^\alpha$-amino groups are protected with the base-labile 9-fluorenylmethyloxycarbonyl (Fmoc) group or t-butyloxycarbonyl (Boc) groups. Side-chain functional groups consistent with Fmoc synthesis are protected, for example, as follows: arginine (2,2,5,7,8-pentamethylchroman-6-sulfonyl); asparagine (O-t-butyl ester); cysteine glutamine and histidine (trityl); lysine (t-butyloxycarbonyl); and serine and tyrosine (t-butyl). An example of a preferred peptide synthetic method is set forth in Example 1 of U.S. Pat. No. 5,696,230, which is incorporated by reference herein. Modification utilizing alternative protecting groups for peptides and peptide derivatives will be apparent to those of skill in the art.

In various embodiments of the invention, the C-terminal analogs of C5a described herein are cyclic (e.g., a ring system containing multiple amino acids and/or amino acid homologs and derivatives and/or intramolecular cyclizations) or acyclic (e.g., linear insofar as the N- and C-termini are not linked by, for example, a peptide bond, nor the presence of intermolecular cyclizations).

Nucleic acids encoding a C-terminal analog of C5a of the disclosure include, for example and without limitation, gene fragments and associated pre-mRNAs, mRNAs, cDNAs, polymorphic variants, alleles, synthetic and naturally occurring mutants.

Polynucleotides encoding a C-terminal analogs of C5a of the disclosure also include, without limitation, those that (1) specifically hybridize under stringent hybridization conditions to a nucleic acid encoding a referenced amino acid sequence as described herein, or hybridize under stringent conditions to conservatively modified variants thereof; (2) have a nucleic acid sequence that has greater than about 60%, about 70%, about 75%, about 80%, about 85%, about 90%, about 95%, about 96%, about 97%, about 98%, about 99%, or higher nucleotide sequence identity, over a region of at least about 5, about 10, about 15, about 20, about 25, about 30, about 40, about 50, about 60, about 70, about 80, about 90, about 100, about 150, about 200, about 250, about 500, about 1000, or more nucleotides, to a reference nucleic acid sequence as described herein. Exemplary "stringent hybridization" conditions include hybridization at 42° C. in 50% formamide, 5×SSC, 20 mM Na.PO$_4$, pH 6.8; and washing in 1×SSC at 55° C. for 30 minutes. It is understood that variation in these exemplary conditions can be made based on the length and GC nucleotide content of the sequences to be hybridized. Formulas standard in the art are appropriate for determining appropriate hybridization conditions. See Sambrook et al., Molecular Cloning: A Laboratory Manual (Second ed., Cold Spring Harbor Laboratory Press, 1989) §§ 9.47-9.51, incorporated herein by reference.

Controlled-Release Materials

The C5a analogs and fusion proteins comprising C5a analogs are useful in preventing and/or treating disease, such as microbial infection, in forming vaccines to induce and/or amplify an immune response, and to target C5a receptor-bearing cells such as APCs. These in vivo uses are enhanced by associating the prophylactic/therapeutic product with a delivery vehicle capable of controlling the release of the therapeutic, prophylactic, vaccine or targeted compound. Use of such delivery systems provides a number of advantages, including but not limited to, stabilization of protein/peptide structure (e.g., conformation) and the concomitant preservation of biological activity, avoidance of enzymatic or chemical degradation or destruction, control of the release of the bioactive compound (e.g., sustained release, burst release with prolonged residual release), and reduction in side effects, such as toxicity.

A variety of structures, of varying composition, have been developed to facilitate the delivery of the prophylactics, therapeutics, vaccines and targeted compounds of the disclosure, and in particular to facilitate the in vivo delivery of proteins and peptides. The disclosure comprehends all such delivery systems. Exemplary types of encapsulating delivery systems, or encapsulating materials, include polymer-based nanoparticles (e.g., nanospheres), nano-gels, microparticles (e.g., microspheres), micro-gels, micro- or nano-capsules as well as polyelectrolyte capsules, biodegradable lattices, polysaccharide capsules, block co-polymer micelles, polyelectrolyte complexes, injectable implants, diffusion-controlled hydrogels, micro-emulsions, and multiple emulsions. Bysell et al., Adv. Drug Del. Rev. (2011), Degim et al., Curr. Pharm. Des. 13:99-117 (2007), each incorporated herein by reference. An exemplary polymer used in preparing delivery vehicles include poly (lactic-co-glycolic acid) (PLGA), which is a versatile biodegradable block co-polymer capable of encapsulating hydrophilic and hydrophobic compounds as well as providing opportunity for covalent attachment to the surface of a PLGA delivery vehicle and non-covalent adsorption to such a vehicle. Other suitable polymers include biocompatible but non-biodegradable polymers such as ethyl cellulose, polymethyl methacrylate, polyethylene glycol, poly-3-hydroxy butyrate (optionally mixed with hydroxyvalerate), starch, alginate, collagen, gelatin, chitin, chitosan, zein or corn protein, cross-linked albumin, azo-cross-linked copolymers of styrene and HEMA-coated particles, hydrogels, maleic anhydride and poly (N-isopropylacrylamide) hybrid hydrogels, hydroxyapatite, hyaluronic acid, polysebacic anhydrides, polyesters, polylactides, polyorthoesters, polycarbonates, polycaprolactones, polyethylene oxide, and amino acids.

Controlled-release formulations also may be prepared using lipids to encapsulate C5a analogs. For example, lipids arranged in bilayer membranes surrounding multiple aqueous compartments to form particles may be used to encapsulate water-soluble c5a analogs and conjugates or fusions thereof for subsequent delivery, as described in U.S. Pat. No. 5,422,120. These particles are generally greater than 10 microns in size and are designed for intra-articular, intrathecal, subcutaneous and epidural administration. Alternatively, liposomes have been used for intravenous delivery of small molecules.

These delivery systems can exhibit several properties useful in the in vivo delivery of bioactive agents. For example, controlled-release gel forms can be constructed in a manner that triggers release of the encapsulated agent, such as by change in pH. Additionally, the delivery systems can be tailored to any one of four distinct release profiles known in the art, which affects the degree of burst release, the duration of agent release and the extent of release. Selection of delivery system material(s) and manipulation of known manufacturing variables allows one of skill in the art to adjust particle size, extent of agent loading, encapsulation efficiency and agent bioactivity. Ye, et al., J. Controlled Release 146:241-260 (2010), incorporated herein by reference.

Any method for manufacturing the controlled-release formulations of C5a analogs and C5a analog fusions that is known in the art is contemplated for use in preparing the formulations according to the disclosure. For example, the controlled-release formulations can be manufactured using a water/oil/water or water/oil/oil double emulsion method, or using a solid/oil/water or solid/oil/oil system. Additionally contemplated are spray drying and spray freeze-drying, electrospray, ultrasonic atomization, microfluidics, as well as use of pore-closing methodology, thermoreversible gels and microfabrication. Ye et al. (supra), incorporated herein by reference. An exemplary method of manufacture is microencapsulation of a C5a analog or C5a analog fusion suing a water insoluble polymer, e.g., PLGA, as an encapsulating matrix. For increasingly hydrophilic prophylactics, therapeutics, vaccines and targeted compounds, the more complex schemes outlined above, e.g., w/o/w, typically produce better results. Li et al., Intl. J. Pharm. 363:26-39 (2008), incorporated herein by reference.

Nanoparticle-encapsulated EP67 and/or EP67-containing vaccines are designed to achieve the slow, sustained release of EP67 or the EP67-containing vaccine such that the immunologic effects of EP67 are achieved over a longer period of time and, consequently, result in a more efficacious immune outcome. The EP67-containing nanoparticles can be used to induce host innate immune responses to bacterial, viral, and fungal infections. Encapsulation of EP67-containing vaccines are also designed to achieve a slow and sustained release of the vaccine as well as a means to depot the vaccine in a tissue area where it can most effectively activate and be taken up by antigen presenting cells (APC).

Another embodiment of the disclosure is EP67 covalently attached to the surface of a nanoparticle such that the contents of the nanoparticle are specifically targeted to C5a receptor (C5aR)-bearing cells such as APCs and other C5aR-bearing cells of non-myeloid origin.

Preparing APC-Targeted Activating Antigens

Selection of Components

Antigen presenting cells have various receptors on their surfaces for known ligands. Binding of ligands to these receptors results in signal transduction events that stimulate immune or tolerance responses. Many of these receptors are known to internalize and recycle in the cell. As such, these receptors are ideal targets for delivering antigens and activation signals simultaneously to APCs.

APCs include several cell types including macrophages, monocytes, dendritic cells, B cells, some T cells and other poorly characterized cell types. It is expected that these different classes of APCs can produce different types of immune responses. Accordingly, by targeting a receptor prevalent on a specific population of APCs, a particular desired immune response will be favored. An APC receptor is particularly appropriate for use as the binding partner of a targeting moiety according to the disclosure based on the following criteria. These receptors are expressed on cells involved in an immune response, i.e., APCs; the receptors are internalized upon binding of binding partner (e.g., ligand); the receptors transmit signals within the APCs that influence antigen processing and presentation by these cells; and some of the receptors are understood to be involved in signaling Th1 type cellular responses, whereas others are expected to generate Th2 type humoral responses.

The C5a receptor is present on PMNs, macrophages, dendritic cells, smooth muscle cells and some mast cells. A number of biological activities have been ascribed to C5a, mostly associated with inflammatory and immune responses. In the aspect of the disclosure drawn to controlled-release vaccine formulations and their use in inducing specific immune responses, a C5a receptor is targeted by the C-terminal C5a analogs of its binding partner C5a. Without wishing to be bound by theory, it is believed that the binding of a conjugate comprising a C5a analog to its cognate receptor activates antigen-presenting cells, including macrophages, monocytes and dendritic cells, through a G protein-mediated signal transduction pathway. Subsequent to signal transduction, the receptor/ligand complex is internalized. In the case of dendritic cells, C5a has been shown to induce a Th1 type response. In this context, the controlled-release formulations comprising a C5a analog conjugated to an antigen are expected to provide improved induction of immune responses in terms of the magnitude or duration of the responses.

The APC-targeted antigens of the disclosure comprise at least one antigenic moiety and at least one targeting moiety in a controlled-release formulation. It is contemplated, for example, that the C5a receptor on an APC is a suitable target for the controlled-release vaccine formulations of the disclosure. The conjugates may comprise naturally occurring C5a, or fragments thereof, as the targeting moiety. Native C5a induces pro-inflammatory responses which may have undesirable side effects, however. Alternatively, the controlled-release formulations may contain a conjugate comprising a C-terminal C5a agonist analog capable of C5a receptor binding and signal transduction in a response selective manner. Such analogs are described in detail in commonly owned U.S. patent application Ser. No. 08/299,285, the entire disclosure of which is incorporated by reference herein.

An exemplary C5a C-terminal decapeptide agonist preferred for use in the present invention is EP67. This decapeptide is a potent agonist of naturally occurring C5a, and is preferred to naturally occurring C5a because its small size contributes to ease of synthesis and solubility. Moreover, these conformationally biased peptides are stable toward serum carboxypeptidase digestion, express a level of biological selectivity, and have been shown to be non-toxic in high concentrations in athymic mice.

Antigens suitable for use as the antigenic moiety of a conjugate in the controlled-release formulations according to the disclosure include any peptide, polypeptide or derivative thereof capable of eliciting an immune response or antibody production under at least one set of conditions known in the art. These antigens include, but are not limited to, peptides, polypeptides (i.e., proteins) and derivatives thereof, such as glycopeptides, phosphopeptides and the like. Synthetic peptide and polypeptide derivatives or analogs, or any other organic or inorganic compound that can be conjugated to a receptor-targeting moiety and that is capable of eliciting an immune response under at least one set of conditions known in the art is suitable for inclusion in the formulations according to the disclosure and for use in the methods according to the disclosure. Moreover, these peptides, proteins and derivatives may comprise single epitopes or multiple epitopes for generating different types of immune responses. Indeed, if an entire protein is conjugated to a targeting moiety, this protein is likely to comprise numerous epitopes, which may vary depending upon the solvent conditions and their effect on secondary and tertiary structure-of the protein. Carbohydrates, nucleic acids and other non-protein substances also may be used as the antigenic moiety. Methods are available in the art for conjugating these substances, and more generally a wide range of organic and inorganic compounds, to the peptide or protein targeting moiety.

In some embodiments of the disclosure, the antigenic moiety comprises an agent that is weakly antigenic or non-antigenic under currently available immunization conditions. Many tumor-associated antigens fall into this category, because the antigens also are expressed by normal cells. Therefore, immunological tolerance to such molecules makes it difficult to stimulate responses against such antigens. Other proteins that fall into this category include naturally occurring proteins from one species (e.g., human) for which it would be desirable to produce antibodies in another species but which are refractory to antibody generation in the other species.

One well-characterized tumor antigen is a cell-surface-associated mucin that is highly overexpressed and differentially glycosylated by different adenocarcinomas, including breast, pancreas, lung and prostate carcinomas. Aberrant glycosylation of MUC1 by adenocarcinomas results in the addition of some blood group carbohydrate antigens to the core protein and the exposure of epitopes which have been detected by monoclonal antibodies on the core protein that are not exposed on forms of this protein produced by normal epithelial cells. A full-length cDNA sequence of human mucin-1 (MUC1) revealed an encoded protein with an average length of approximately 1200 amino acids (depending on the length of the tandem repeat) with several obvious domains: an amino terminal signal peptide; a large domain made up of multiple identical 20-amino-acid tandem repeats flanked by several repeats that contain degenerate sequences; a hydrophobic-spanning domain of 31 amino acids; and a cytoplasmic domain of 69 amino acids at the carboxyl terminus. The most well-characterized tumor-associated epitopes described to date for MUC1 are found in the tandem repeat domain. These epitopes include carbohydrate structures and protein structures. MUC1 tumor-associated epitopes are well-characterized, and thus have been proposed to be used for the production of tumor vaccines using conventional methods. Exemplary compositions of the present invention comprise MUC1 epitopes as the antigenic moiety of the APC-targeted conjugates contained in controlled-release formulations according to the disclosure.

MUC1 epitope predicted to bind to class I molecules of the H-2k$^b$ type has sequence homology to the juxtamembrane region of MUC1; YKQGGFLGL (SEQ ID NO: 21); MUC1 tandem repeat has the sequence: GVTSAPDTRRA-PGSTAPPAH (SEQ ID NO: 22). The components comprising the APC-targeted conjugates contained in the controlled-release formulations of the disclosure can be made separately, then conjugated. For example, a small peptide analog, such as one of the above-described C5a agonists, may be produced by peptide synthesis methods, and conjugated to a protein that has been purified from naturally occurring biological sources. Alternatively, proteins engineered for expression via recombinant methods may be used. Additionally, targeted antigens comprising peptide components (e.g., a peptide antigenic epitope conjugated to a peptide receptor ligand) can be synthesized in tandem by peptide synthesis chemistry according to known methods. Finally, targeted antigens of the invention comprising two larger polypeptide moieties (e.g., a large polypeptide antigen linked to a large ligand) can be made by recombinant techniques. For example, DNA molecules encoding both components can be ligated in-frame by recombinant means, then expressed as the conjugated fusion protein.

Uses of APC-targeted Activating Antigens

The APC-targeted activating antigens of conjugates contained in controlled-release formulations according to the disclosure have broad potential for clinical applications in humans and other animals. A significant impediment to the development of vaccines and other immunotherapeutic agents is the apparent inability of particular antigens to readily be taken up and processed by antigen presenting cells. The compositions of the invention facilitate the specific delivery of an antigen to a population of antigen presenting cells, whereupon the delivery mechanism (e.g., using as the targeting moiety a receptor ligand capable of transducing a biological signal) simultaneously activates the antigen presenting pathway of the APC. Thus, the present disclosure enables development of vaccines and other immunotherapeutics that can specifically target any peptide antigen or other antigenic structure covalently attached to a binding partner for a receptor present on an antigen presenting cell. Without wishing to be bound by theory, it is believed that antigens linked to ligands that selectivity bind to, and activate, a particular population of APCs can not only generate an immune response, but can influence the nature of the immune response that is generated. Thus, immune responses that favor antibody, cellular, Th1 or Th2 responses, respectively, may be selectively generated. Vaccines may also be developed with an array of such targeting moieties, thereby serving to target a selected antigen or antigens to several populations of APCs and to simultaneously activate these and other cells involved in various immune modulatory pathways.

The ability to generate either antibody- or cell-mediated immune responses against different specific antigens has broad general applicability, and it is expected that the controlled-release formulations of conjugates comprising APC-targeted antigens will be useful for these purposes. For example, antibody responses have been shown to be capable of protecting against different viral or bacterial infection, and antibodies are known to inactivate different toxins or toxic compounds that may affect the well being of humans or other animals. Different cell-mediated immune responses can provide protection against viral or other intracellular pathogens, and can play a role in some anti-tumor responses.

The targeted antigens are expected to find particular utility in the development of active specific immunotherapeutic agents (i.e., vaccines, such as cancer vaccines) based on cancer-associated antigens. For example, it has been hypothesized that induction of strong cell-mediated immune responses (involving Th1 cells and/or cytotoxic T lymphocytes) would provide the most effective protection against various forms of cancer. A vaccination strategy utilizing APC-targeted antigens can be designed to induce this type of response. In this regard, it is known that stimulation with some cytokines (IL-12, IFNγ) can induce predominantly Th1 type responses over Th2 type responses for certain antigens.

The targeted antigens of the disclosure will find broad utility in the production of antibodies for use as immunodiagnostic and immunotherapeutic agents. For immunodiagnostic purposes, antibodies are widely used in various quantitative and qualitative assays for the detection and measurement of biological molecules associated with diseases or other pathological conditions. For reasons that often are not well understood, it is sometimes difficult to generate antibodies against certain biological molecules using conventional means. The controlled-release formulations of the disclosure provide an alternative means for inducing an animal to produce antibodies against a weakly antigenic substance. The utility of the compositions of the invention in this regard is shown clearly in Example 9, below, in connection with serum amyloid A (SAA). The appearance and abundance of this protein in the body is strongly correlated with systemic inflammatory stress, which is a condition that is very difficult to quantitate. It is believed that quantitative assays for SAA levels would be an excellent indicator of general, systemic inflammation; therefore it would be of benefit to generate antibodies against the protein in a non-human species. This protein has proved particularly refractory to the generation of antibodies using conventional measures. As described in Example 9, a targeted antigen comprising SAA conjugated to a C5a peptide ligand produced a significant antibody response in mice injected with the conjugated molecule. In a similar fashion, targeted antigens comprising any weakly antigenic component of interest could be made and used to produce specific antibodies in laboratory animals, for use as immunodiagnostic reagents.

Antibodies for use as immunotherapeutic agents can also be generated using the compositions of the disclosure. As one example, there has been a great deal of recent interest in developing reagents capable of down-regulating or inhibiting the complement cascade to modulate local and systemic inflammatory responses. To this end, the C3a convertase, which is active early in the cascade, could provide an ideal target for complement inhibition. C3a convertase cleaves the peptide C3 into two components, C3a and C3b, and therefore must be able to access the cleavage site on C3 in order to accomplish the result. Antibodies directed toward the C3a-C3b cleavage site are expected to be effective in blocking access of C3a convertase to the cleavage site, thereby inhibiting this early step in the complement cascade. Such antibodies may be generated using a controlled-release formulation of a targeted antigen of the disclosure comprising, as the antigenic moiety, the short peptide sequence comprising the C3a/C3b cleavage site. The sequence could then be conjugated to an appropriate targeting moiety, such as the C5a C-terminal decapeptide agonists exemplified herein. Thus, the compositions would be useful to generate an immunotherapeutic agent (e.g., an antibody that blocks the activity of C3a convertase) for treating an adverse inflammatory condition.

Microorganisms, Infections and Diseases

The selective activation of host innate immunity with a safe, well-designed immune stimulatory molecule such as one of the conformationally-biased, response-selective analogs of C5a 65-74 described herein would reduce the mutational pressures imposed by antimicrobial therapy currently being employed and would be important for treating bacterial, fungal, and viral infections by stimulating host innate immunity. Such an approach induces host innate immune activation via the immunostimulatory portion of the complement pathway, rather than through pathogen-associated molecular pattern (PAMP) or Toll-like receptors. Thus, such analogs will be effective against pathogens that may develop defenses to skirt immune activation via PAMPs. As an immunotherapeutic, such analogues can be used with other conventional therapies to complement their activity and enhance the overall outcome.

In one embodiment, these C-terminal analogs of C5a are synthetic products. As such, C-terminal analogs of C5a overcome many manufacturing issues required to accommodate rapid distribution to a world-wide population. These analogs are simple to synthesize and purify in large quantities; it is characterized at the molecular level; it is generated as a dry powder and purified via standard HPLC methods without risk of associated DNA, RNA, or bacterial contamination. This powder is stable for years at room temperature. This allows for convenient distribution to the clinic where it can be dissolved immediately prior to use. At no point in manufacture, distribution, or storage is refrigeration or the use of preservatives required.

Host innate immunity is the first line of defense in controlling infections. It occurs rapidly and is not necessarily antigen specific. It provides a broad spectrum defense mechanism for acute infections. Acquired immunity is a result of exposing the host to the pathogen or a component of the pathogen in the form of a vaccine that then allows the host to develop a long lasting immune response (both humoral and/or cell mediated) to the specific pathogen. In various embodiments, the C-terminal analogs of C5a described herein induce host innate immunity and/or acquired immunity. The ability to induce innate immunity in a non-antigen-specific method has advantages in that it affords induction of immune responses to a wide range of pathogens irrespective of the nature of the antigens these pathogens express. Thus, the ability to induce a protective immune response is not dependent upon reaction to a specific antigen expressed by a pathogen, but rather to the pathogen itself.

As described herein, the ability to induce innate immunity in a non-antigen-specific method has advantages in that it affords induction of immune responses to a wide range of pathogens irrespective of the nature of the antigens these pathogens express. Thus, the ability to induce a protective immune response is not dependent upon reaction to a specific antigen expressed by a pathogen, but rather to the pathogen itself.

The overuse of antibiotics for treating infections has created mutational pressures that have facilitated an alarming rise in resistant bacteria, which has outpaced the development of new antibiotics to treat them. The ability to treat these infections is not only a major public health concern, but also presents an urgently needed capability that provides security against bioterrorism and the potential of an intended release of "superbugs" that may be manufactured to evade traditional anti-bacterial therapies.

The analogs of the disclosure represent, in various embodiments, a therapeutic molecule to treat or prevent infections or diseases associated with, a variety of microorganisms or infectious particles, including but not limited to bacteria, virus, fungus, parasite, protozoan, prion, cancer cells, or other transformed cells. In one embodiment, the infection is caused by an antibiotic-resistant microorganism, such as bacteria. In still another embodiment, the therapeutic molecule is used to control bacterial burden associated with a biofilm.

The analogs of the disclosure represent, in various embodiments, a therapeutic molecule to treat or prevent, either by direct killing or by activating a host immune response, a variety of diseases and infections, including but not limited to those that relate to the respiratory system, such as obstructive lung diseases (e.g., emphysema, bronchitis, asthma, chronic obstructive pulmonary disease, bronchiectasis, byssinosis, bronchiolitis, asbestosis, restrictive lung diseases such as fibrosis, cystic fibrosis, sarcoidosis, alveolar damage, pleural effusion, hypersensitivity pneumonitis, pleurisy, lung cancer, infectious lung diseases such as influenza, upper respiratory tract infections, lower respiratory tract infections or pneumonias, tuberculosis, vascular lung diseases such as pulmonary edema, pulmonary embolism, pulmonary hypertension, and respiratory tumors), those that are inflammatory-related such as rheumatoid arthritis, restenosis, asthma, Crohn's disease, incontinentia pigmenti, diabetes, obesity, autoimmune disease, lupus, multiple sclerosis, transplant/graft rejection, gene therapy applications, ischemia/reperfusion injury (CNS and myocardial), glomerulonephritis, sepsis, allergic airway inflammation, inflammatory bowel disease, and infection.

The analogs of the disclosure represent, in various embodiments, a therapeutic molecule to treat or prevent, either by direct killing or by activating a host immune response, an infectious disease including, but not limited to, *Acinetobacter* infections, Actinomycosis, African sleeping sickness (African trypanosomiasis), AIDS (Acquired immune deficiency syndrome), Amebiasis, Anaplasmosis, Anthrax, Arcanobacterium haemolyticum infection, Argentine hemorrhagic fever, Ascariasis, Aspergillosis, Astrovirus infection, Babesiosis, *Bacillus cereus* infection, Bacterial pneumonia, Bacterial vaginosis (BV), Bacteroides infection, Balantidiasis, Baylisascaris infection, BK virus infection, Black piedra, Blastocystis hominis infection, Blastomycosis, Bolivian hemorrhagic fever, *Borrelia* infection, Botulism (and Infant botulism), Brazilian hemorrhagic fever, Brucellosis, Burkholderia infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, chickenpox, *Chlamydia, Chlamydophila pneumoniae* infection, Cholera, Chromoblastomycosis, Clonorchiasis, *Clostridium difficile* infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum, Fasciolopsiasis, Fasciolosis, Fatal familial insomnia (FFI), Filariasis, Food poisoning by *Clostridium perfringens*, Free-living amebic infection, Fusobacterium infection, Gas gangrene (Clostridial myonecrosis), Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome (HPS), *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Mastitis, Marburg hemorrhagic fever (MHF), Measles, Melioidosis (Whitmore's disease), Meningitis, Meningococcal disease, Metagonimiasis, Microsporidiosis, Molluscum contagiosum (MC), Mumps, Murine typhus (Endemic typhus), *Mycoplasma pneumonia*, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis pneumonia* (PCP), *Pneumonia*, Poliomyelitis, *Prevotella* infection, Primary amoebic meningoencephalitis (PAM), Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsialpox, Rift Valley fever (RVF), Rocky mountain spotted fever (RMSF), Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans (OLM)), Toxocariasis (Visceral Larva Migrans (VLM)), Toxoplasmosis, Trichinellosis, Trichomoniasis, Trichuriasis (Whipworm infection), Tuberculosis, Tularemia, Ureaplasma urealyticum infection, Venezuelan equine encephalitis, Venezuelan hemorrhagic fever, Viral *pneumonia*, West Nile Fever, White piedra (Tinea blanca), *Yersinia* pseudotuberculosis infection, Yersiniosis, Yellow fever, and Zygomycosis.

The analogs of the disclosure represent, in various embodiments, a therapeutic molecule to treat or prevent, either by direct killing or by activating a host immune response, a subject infected with a pathogen (and their associated diseases) including, but not limited to, cytomegalovirus (autism, autoimmune diseases, brain tumor, dementia, diabetes mellitus type 2, Guillain-Barré syndrome, lupus, metabolic syndrome, myocardial infarction), enteroviruses (amyotrophic lateral sclerosis, ADHD, autoimmune diseases, carcinoid tumors, chronic fatigue syndrome, diabetes mellitus type 1, diabetes mellitus type 2, Guillain-Barré syndrome, myocardial infarction, schizophrenia), Epstein-Barr virus (autoimmune diseases, breast cancer, esophageal cancer, Hodgkin's lymphoma, nasopharyngeal carcinoma, chronic obstructive pulmonary disease, seasonal affective disorder, lupus, multiple sclerosis), Hepatitis B virus (hepatocellular carcinoma, pancreatic cancer, vasculitis), Hepatitis C virus (Hodgkin's lymphoma, hepatocellular carcinoma, diabetes mellitus type 2, vasculitis), Herpes simplex virus (Alzheimer's disease, coronary heart disease, metabolic syndrome), HIV (ADHD, autoimmune diseases, Hodgkin's lymphoma, Kaposi's Sarcoma, non-Hodgkin lymphoma, dementia, vasculitis), Human herpesvirus 6 (ADHD, chronic fatigue syndrome, epilepsy, multiple sclerosis), Influenza A (ADHD, Parkinson's disease), Parvovirus B19 (autoimmune diseases, chronic fatigue syndrome, lupus, rheumatoid arthritis, vasculitis), Bartonella (major depressive disorder, panic disorder), *Borrelia* (anorexia nervosa, ADHD, bipolar disorder, dementia, depression, obsessive-compulsive disorder, rheumatoid arthritis, sarcoidosis, schizophrenia), *Chlamydia pneumonia* (Alzheimer's disease, asthma, atherosclerosis, lung cancer, chronic fatigue syndrome, chronic obstructive pulmonary disease, coronary heart disease, metabolic syndrome, multiple sclerosis, myocardial infarction, stroke, Tourette's syndrome), *Helicobacter pylori* (Alzheimer's disease, autoimmune diseases, pancreatic cancer, stomach cancer, metabolic syndrome, obesity, psoriasis, sarcoidosis, stroke), *Mycobacterium tuberculosis* (autoimmune diseases, depression, stroke), *Streptococcus* (anorexia nervosa, ADHD, colorectal cancer, obsessive-compulsive disorder, Tourette's syndrome), and *Toxoplasma gondii* (Alzheimer's disease, depression, Parkinson's disease, Tourette's syndrome).

The analogs of the disclosure represent, in various embodiments, a therapeutic molecule to treat or prevent, either by direct killing or by activating a host immune response, infections or diseases associated with a variety of infections caused by bacteria including, but not limited to, antibiotic-resistant bacteria such as methicillin-resistant *S. aureus* (MRSA), including health care-associated MRSA (HA-MRSA) and community associated MRSA (CA-MRSA), and MRSA strain USA300-FPR3757, vancomycin-resistant *S. aureus* (VRSA), *S. pyogenes*, e.g., resistant to macrolide, penicillin-resistant pneumonia caused by *Streptococcus pneumoniae* (commonly known as pneumococcus), *Mycobacterium tuberculosis* (commonly resistant to isoniazid and rifampin) and Extensively Drug-Resistant Tuberculosis (XDR TB), multidrug-resistant *Enterococcus faecalis* and *Enterococcus faecium*, *Pseudomonas aeruginosa*, *Clostridium difficile* (e.g., clindamycin-resistant and fluoroquinolone antibiotics), *Acinetobacter baumannii*, and any antibiotic-resistant strain of bacteria described herein.

The analogs of the disclosure represent, in various embodiments, a therapeutic molecule to treat or prevent, either by direct killing or by activating a host immune response, infections or diseases associated with, and/or directly kill, a variety of infections caused by bacteria including, but not limited to, *Acinetobacter baumannii, Bacillus anthraces, Bordetella pertussis, Borrelia burgdorferi, Brucella abortus, Brucella canis, Brucella melitensis, Brucella suis, Campylobacter jejuni, Chlamydia pneumonia, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus mutans, Streptococcus pneumoniae, Streptococcus pyogenes, Treponema pallidum, Vibrio cholerae,* and *Yersinia pestis.*

The analogs of the disclosure also represent, in various embodiments, a therapeutic molecule to control, prevent or treat, either by direct killing or by activating a host immune response, biofilms associated, for example, with catheters or other artificial implants. Such biofilms are caused, in various embodiments, by bacteria including, but not limited to, *Pseudomonas aeruginosa, Streptococcus mutans, Streptococcus sanguinis, Legionella, Neisseria gonorrhoeae,* and *Staphylococcus aureus.*

The analogs of the disclosure represent, in various embodiments, a therapeutic molecule to treat or prevent, either by direct killing or by activating a host immune response, infections or diseases associated with a variety of infections or diseases caused by viruses including, but not limited to, Poxviridae, Chordopoxvirinae, Orthopoxvirus, Cowpoxvirus, Monkeypox virus, Vaccinia virus, Variola virus, Parapoxvirus, Bovine papular stomatitis virus, Orf virus, Pseudocowpox virus, Molluscipoxvirus, Molluscum contagiosum virus, Yatapoxvirus, Tanapox virus, Yaba monkey tumor virus, Herpesviridae, Alphaherpesvirinae, Simplexvirus, Human herpesvirus 1, Herpes simplex virus 1, Human herpesvirus 2, Herpes simplex virus 2, Varicellovirus, Human herpesvirus 3, Varicella-zoster virus, Betaherpesvirinae, Cytomegalovirus, Human herpesvirus 5, Human cytomegalovirus, Roseolovirus, Human herpesvirus 6, Human herpesvirus 7, Gammaherpesvirinae, Lymphocryptovirus, Human herpesvirus 4, Epstein-Barr virus, Rhadinovirus, Human herpesvirus 8, Kaposi's sarcoma-associated herpesvirus, Adenoviridae, Mastadenovirus, Human adenovirus A, Human adenovirus B, Human adenovirus C, Human adenovirus D, Human adenovirus E, Human adenovirus F, Polyomaomaviridae, Polyomavirus, BK polyomavirus, Human polyomavirus, JC polyomavirus, Papillomaviridae, Alphapapillomavirus, Human papillomavirus 2, Human papillomavirus 10, Human papillomavirus 6, Human papillomavirus 7, Human papillomavirus 16, Human papillomavirus 18, Human papillomavirus 26, Human papillomavirus 32, Human papillomavirus 34, Human papillomavirus 53, Human papillomavirus 54, Human papillomavirus 61, Human papillomavirus 71, Human papillomavirus cand90, Betapapillomavirus, Human papillomavirus 5, Human papillomavirus 9, Human papillomavirus 49, Human papillomavirus cand92, Human papillomavirus cand96, Gammapapillomavirus, Human papillomavirus 4, Human papillomavirus 48, Human papillomavirus 50, Human papillomavirus 60, Human papillomavirus 88, Mupapillomavirus, Human papillomavirus 1, Human papillomavirus 63, Parvoviridae, Parvovirinae, Erythrovirus, B19 virus, Hepadnaviridae, Orthohepadnavirus, Hepatitis B virus, Retroviridae, Orthoretrovirinae, Deltaretrovirus, Primate T-lymphotropic virus 1, Primate T-lymphotropic virus 2, Lentivirus, Human immunodeficiency virus 1, Human immunodeficiency virus 2, Reoviridae, Orthoreovirus, Mammalian orthoreovirus, Orbivirus, African horse sickness virus, Changuinola virus, Corriparta virus, Orungo virus, Rotavirus, Rotavirus A, Rotavirus B, Mononegavirales, Filoviridae, Marburgvirus, Lake Victoria marburgvirus, Ebolvirus, Ivory Coast ebolavirus, Reston ebolavirus, Sudan ebolavirus, Zaire ebolavirus, Paramyxoviridae, Paramyxovirinae, Respirovirus, Human parainfluenza virus 1, Human parainfluenza virus 3, Morbillivirus, Measles virus, Edmonston virus, Rubulavirus, Human parainfluenza virus 2, Human parainfluenza virus 4, Mumps virus, Henipavirus, Hendravirus, Nipahvirus, Pneumovirinae, Pneumovirus, Human respiratory syncytial virus, Metapneumovirus, Human metapneumovirus, Rhabdoviridae, Vesiculovirus, Chandipura virus, Cocal virus, Isfahan virus, Piry virus, Vesicular stomatitis Alagoas virus, Vesicular stomatitis Indiana virus, Vesicular stomatitis New Jersey virus, Lyssavirus, Australian bat lyssavirus, Rabies virus, Orthomyxoviridae, Influenzavirus A, Influenza A virus, Influenzavirus B, Influenza B virus, Influenzavirus C, Influenza C virus, Bunyaviridae, Bunyavirus, Bunyamwera virus, Bwamba virus, California encephalitis virus, Guama virus, Oriboca virus, Oropouche virus, Hantavirus, Andes virus, Hantaan virus, Puumala virus, Seoul virus, Dobrava-Belgrade virus, Bayou virus, Black Creek Canal virus, New York virus, Sin Nombre virus, Nairovirus, Crimean-Congo hemorrhagic fever virus, Nairobi sheep disease virus, Phlebovirus, Rift Valley fever virus, Sandfly fever Naples virus, Arenaviridae, Arenavirus, Lassa virus, Lymphocytic choriomeningitis virus, Guanarito virus, Junin virus, Machupo virus, Sabiá virus, Deltavirus, Hepatitis delta virus, Nidovirales, Coronaviridae, Coronavirus, Human coronavirus 229E, Human coronavirus OC43, Human enteric coronavirus, Severe acute respiratory syndrome coronavirus, Torovirus, Picornaviridae, Enterovirus, Human enterovirus A, Human enterovirus B, Human enterovirus C, Human enterovirus D, Poliovirus, Rhinovirus, Human rhinovirus A, Human rhinovirus B, Hepatovirus, Hepatitis A virus, Parechovirus, Human parechovirus, Caliciviridae, Norovirus, Norwalk virus, Sapovirus, Sapporo virus, Hepevirus, Hepatitis E virus, Astroviridae, Mamastrovirus, Human astrovirus, Togaviridae, Alphavirus, Chikungunya virus, O'nyong-nyong virus, Mayaro virus, Ross River virus, Barmah Forest virus, Sindbis virus, Ockelbo virus, Venezuelan equine encephalitis virus, Western equine encephalitis virus, Eastern equine encephalitis virus, Rubivirus, Rubella virus, Flaviviridae, Flavivirus, Kyasanur Forest disease virus, Omsk hemorrhagic fever virus, Powassan virus, Louping ill virus, Tickborne encephalitis virus, Dengue virus, Japanese encephalitis virus, Murray Valley encephalitis virus, St. Louis encephalitis virus, West Nile virus, Ilheus virus, Yellow fever virus, Apoi virus, Hepacivirus, Hepatitis C virus, GB virus B, and GB virus A.). In various embodiments, the infection or disease is caused by influenza A or human immunodeficiency virus (HIV).

The analogs of the disclosure represent, in various embodiments, a therapeutic molecule to treat or prevent, either by direct killing or by activating a host immune response, infections or diseases associated with a variety of fungal infections including, but not limited to, *Candida* (e.g., *C. albicans*), *Aspergillus* (e.g., *A. fumigates, A. flavus*, and *A. clavatus*), *Cryptococcus* (e.g., *C. neoformans, C. laurentii, C. albidus*, and *C. gatti*), *Histoplasma* (e.g., *H. capsulatum*), *Pneumocystis* (e.g., *P. jirovecii*), *Stachybotrys* (e.g., *S. chartarum*), and *Coccidioides* (e.g., *C. immitis* and *C. posadasii*).

The analogs of the disclosure represent, in various embodiments, a therapeutic molecule to treat or prevent, either by direct killing or by activating a host immune response, infections or diseases associated with a variety of parasitic organisms and/or infections including, but not limited to, protozoans, helminthes, parasitic worms, Halzoun syndrome, myiasis, Chogoe fly, human botfly, candiru, bedbug, head louse, body louse, crab louse, demodex, scabies, and screwworm. Further, the analogs of the disclosure represent, in various embodiments, a therapeutic approach to treat or prevent infections or diseases associated with, a variety of protozoans and or protozoan infections including, but not limited to, *Entamoeba histolytica, Giardia lambda, Trichomonas vaginalis, Trypanosoma brucei, T cruzi, Leishmania donovani, Balantidium coli, Toxoplasma gondii, Plasmodium* Spp., *Babesia microti*, acanthamoeba, babesiosis, balantidiasis, blastocystosis, coccidia, dientamoebiasis, amoebiasis, *giardia*, isosporiasis, leishmaniasis, primary amoebic meningoencephalitis (PAM), malaria, rhinosporidiosis, toxoplasmosis (parasitic *pneumonia*), trichomoniasis, sleeping sickness, and Chagas disease.

The analogs of the disclosure represent, in various embodiments, a therapeutic molecule to treat or prevent, either by direct killing or by activating a host immune response, diseases associated with infectious particles such as prions including, but not limited to, scrapie, bovine spongiform encephalopathy (BSE, mad cow disease), transmissible mink encephalopathy, chronic wasting disease, feline spongiform encephalopathy, exotic ungulate encephalopathy, Creutzfeldt-Jakob disease, iatrogenic Creutzfeldt-Jakob disease, variant Creutzfeldt-Jakob disease, familial Creutzfeldt-Jakob disease, sporadic Creutzfeldt-Jakob disease, Gerstmann-Straussler-Scheinker syndrome, fatal familial insomnia, and Kuru.

The analogs of the disclosure also represent, in various embodiments, a therapeutic approach to treat a subject (e.g., human) that has multiple diseases or infections or, in various embodiments, treating one or more than one infection or disease while also preventing additional infections or diseases, either by direct killing or by activating a host immune response.

Compositions and Methods of Administering

In various embodiments of the disclosure, a composition comprising one or more "therapeutic agents" or "active agent," e.g., a C-terminal analog of C5a, is provided. Moreover, such compositions may be associated with a delivery system providing for the controlled-release of the composition, as described above.

In various embodiments, the composition comprises a pharmaceutically acceptable carrier, e.g., one or more solvents, dispersion media, coatings, antibacterial and antifungal agents, isotonic and absorption delaying agents, and the like, compatible with administration to a mammal, such as a human. Any carrier compatible with the excipient(s) and therapeutic agent(s) (e.g., C-terminal analog of C5a) is suitable for use. Supplementary active compounds may also be incorporated into the compositions. A composition of the disclosure is formulated to be compatible with its intended route of administration. Examples of routes of administration include oral administration (ingestion) and parenteral administration, e.g., intravenous, intradermal, subcutaneous, inhalation, nasal, transdermal (topical), transmucosal, buccal, sublingual, pulmonary and rectal administration. Solutions or suspensions used for parenteral application may include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH may be adjusted with acids or bases, such as hydrochloric acid or sodium hydroxide.

Oral compositions generally include an inert diluent or an edible carrier. Oral formulations generally take the form of a pill, tablet, capsule (e.g., softgel capsule, solid-filled capsule, or liquid-filled capsule), solid lozenge, liquid-filled lozenge, mouth and/or throat drops or spray, effervescent tablets, orally disintegrating tablet, suspension, emulsion, syrup, elixir, or tincture. The composition may be contained in enteric forms to survive the stomach or further coated or mixed to be released in a particular region of the gastrointestinal tract by known methods. Solid oral dosage forms are typically swallowed immediately, or slowly dissolved in the mouth. Oral compositions may also be prepared using a fluid carrier for use as a mouthwash, wherein the compound in the fluid carrier is applied orally and swished and expectorated or swallowed. Oral formulations optionally contain any of the following ingredients, or compounds of a similar nature: a binder such as microcrystalline cellulose, gum tragacanth or gelatin; starch or lactose; a disintegrating agent such as alginic acid, Primogel™, or corn starch; a lubricant such as magnesium stearate; a glidant such as colloidal silicon dioxide; and/or a sweetening agent such as sucrose or saccharin.

For administration by inhalation, the composition is optionally delivered in the form of a spray. The spray may be an aerosol spray from a pressured container or dispenser, which contains a suitable propellant, e.g., a gas such as carbon dioxide, or a nebulizer. The composition is optionally formulated for delivery via a dry powder inhaler (DPI), a metered dose inhaler (pMDI), nasal spray, or a vaporizer. For routes of administration involving absorption of an agent and/or excipient through mucosal membrane, the composition further optionally comprises a penetrant.

Optionally, the composition is formulated as a "liquid respiratory composition," i.e., a composition in a form that is deliverable to a mammal via the oral cavity, mouth, throat, nasal passage or combinations thereof. These compositions can be delivered by a delivery device selected from droppers, pump, sprayers, liquid dropper, spoon, cup, squeezable sachets, power shots, and other packaging and equipment, and combinations thereof. In one embodiment, the liquid respiratory composition comprises the therapeutic agent, and excipient, a thickening polymer (e.g., xanthan gum, cellulosic polymers such as carboxymethycellulose (CMC), hydroxethylcellulose, hydroxymethylcellulose, and hydroxypropylmethylcellulose, carrageenan, polyacrylic acid, cross-linked polyacrylic acid such as Carbopol®, polycarbophil, alginate, clay, and combinations thereof), and optionally a mucoadhesive polymer (e.g., polyvinylpyrrolidone (Povidone), methyl vinyl ether copolymer of maleic anhydride (Gantrez®), guar gum, gum tragacanth, polydextrose, cationic polymers, poly(ethylene oxide), poly(ethylene glycol), poly(vinyl alcohol), poly(acrylic acid), cross-linked polyacrylic acid such as Carbopol®, polycarbophil, poly(hydroxyl ethyl methacrylate), chitosan, cellulosic polymers such as carboxymethycellulose (CMC), hydroxethylcellulose, hydroxymethylcellulose, and hydroxypropylmethylcellulose, and combinations thereof). The composition is preferably a non-Newtonian liquid that exhibits zero shear viscosity from about 100 centiPoise (cP) to about 1,000,000 cP, from about 100 cP to about 500,000 cP, from about 100 cP to about 100,000 cP, from about 100 cP to about 50,000 cP, from about 200 cP to about 20,000 cP, from about 1,000 to about 10,000 cP at a temperature of about 37° C., as measured according to the Shear Viscosity Method. The pH range of the formulation is generally from about 1 to about 7, from about 2 to about 6.5, and from about 4 to about 6.

In various embodiments, in addition to the excipient(s) and therapeutic agent(s) described herein, a nasal spray formulation comprises benzalkonium chloride, camphor, chlorhexidine gluconate, citric acid, disodium EDTA, eucalyptol, menthol, purified water, and/or tyloxapol. An exemplary oral composition comprises FD&C Blue No. 1, gelatin, glycerin, polyethylene glycol, povidone, propylene glycol, purified water, sorbitol special, and/or titanium dioxide in addition to an excipient and acetaminophen, doxylamine succinate, and phenylephrine HCl (or dextromethorphan).

Pharmaceutical compositions suitable for injectable use include sterile aqueous solutions (where water-soluble), or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition is sterile and fluid to allow syringability. The carrier may be a solvent or dispersion medium containing, for example, water, ethanol, polyol (for example, glycerol, propylene glycol, and liquid polyethylene glycol, and the like), and suitable mixtures thereof. Fluidity is maintained, for example, by the use of a coating such as lecithin, by the maintenance of the required particle size in the case of dispersion, and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions may be brought about by including in the composition an agent that delays absorption, for example, aluminum monostearate and gelatin. The injectable preparations may be enclosed in ampules, disposable syringes or multiple dose vials made of glass or plastic.

In various embodiments of the disclosure, powders, creams and gels are contemplated for topical administration of a pharmaceutical composition. In one embodiment, the topical administration refers to the application of a therapeutic composition to a localized area of the body or to the surface of a body part where action or symptom relief is desired. In one embodiment, a transdermal patch is used according the disclosure. In still other embodiments, a pharmaceutical composition according to the disclosure is embedded, e.g., in wound dressings, bandages (e.g., hydrocolloids, hydrogels, alginates, foams, gauze), and/or surgical sutures to prevent and/or treat infections and improve wound (e.g., scrapes, cuts, and surgical incisions) healing.

In one embodiment, the components of the composition are prepared with carriers that will protect the components against rapid elimination from the body, such as a controlled release formulation. Biodegradable, biocompatible polymers may be used, such as ethylene vinyl acetate, polyanhydrides, polyglycolic acid, collagen, polyorthoesters, and polylactic acid.

The formulation is provided, in various aspects, in dosage unit form for ease of administration and uniformity of dosage. "Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms are dictated by and are directly dependent on the unique characteristics of the excipient(s) and therapeutic agent(s) and the particular biological effect to be achieved.

Safety and efficacy of compositions described herein are determined by standard procedures using in vitro or in vivo technologies, such as the materials and methods described herein. Administration may be on an as-needed or as-desired basis, for example, once-monthly, once-weekly, or daily, including multiple times daily, for example, at least once daily, from one to about ten times daily, from about two to about four times daily, or about three times daily. A dose of composition optionally comprises about from about 0.001 mg to about 1000 mg active agent, alternatively from about 2.5 mg to about 750 mg active agent, and alternatively from about 5 mg to about 650 mg of the active agent. In one embodiment, a dose of composition according to the disclosure comprises about from 0.1 mg to about 0.25 mg. In various embodiments, a dose of composition according to the disclosure comprises 25 µg, 50 µg, 60 µg, 70 µg, 80 µg, 90 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg or 500 µg. In various embodiments, a dose of composition according to the disclosure comprises between 25 µg to 500 µg, 50 µg to 400 µg, 100 µg to 300 µg, or 200 µg to 250 µg.

In various embodiments, a therapeutic agent, or a pharmaceutical composition comprising a therapeutic agent, is used in combination with one or more other active agents useful for treating or preventing infections or diseases. The other active agent(s) can enhance the effects of the therapeutic agent and/or exert other pharmacological effects in addition to those of the therapeutic agent. Non-limiting examples of active agents that can be used in combination with a therapeutic agent are immunosuppressants (e.g., cyclosporine, azathioprine), corticosteroids, anti-inflammatory agents, chemotherapeutic agents, antibiotics, antifungals, antivirals and antiparasitics. As described herein, other exemplary active agents that are contemplated include vaccines (e.g., existing vaccines directed to a specific pathogen or disease) and vaccines comprising C-terminal analogs of C5a conjugated to a specific antigen.

To achieve a desired therapeutic outcome in a combination therapy, a therapeutic agent such as a C-terminal analog of C5a and other active agent(s) are generally administered to a subject in a combined amount effective to produce the desired therapeutic outcome (e.g., reduction or elimination of one or more symptoms). The combination therapy can involve administering the C-terminal analog of C5a and the other active agent(s) at about the same time. Simultaneous administration can be achieved by administering a single composition that contains both the C-terminal analog of C5a and the other active agent(s). Alternatively, the other active agent(s) can be taken separately at about the same time as a pharmaceutical formulation comprising the C-terminal analog of C5a.

In other alternatives, administration of the therapeutic agent such as a C-terminal analog of C5a can precede or follow administration of the other active agent(s) by an interval ranging from minutes to hours. In embodiments where the C-terminal analog of C5a and the other active agent(s) are administered at different times, the C-terminal analog of C5a and the other active agent(s) are administered within an appropriate time of one another so that both the C-terminal analog of C5a and the other active agent(s) can exert a beneficial effect (e.g., synergistically or additively) on the recipient. In some embodiments, the C-terminal analog of C5a is administered to the subject within about 0.5-12 hours (before or after), or within about 0.5-6 hours (before or after), of the other active agent(s). In certain embodiments, the C-terminal analog of C5a is administered to the subject within about 0.5 hour or 1 hour (before or after) of the other active agent(s).

A "booster" dose of a C-terminal analog of C5a or a pharmaceutical composition comprising a C-terminal analog of C5a, separately or in combination with another active agent as described above, is also contemplated by the disclosure. A booster dose may be administered about 1 week, about 1 month, about 2 months, about 3 months, about 4 months, about 5 months, about 6 months, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years, about 15 years, and about 20 years after an initial administration.

The invention is further described in the following examples, wherein Example 1 shows intranasal instillation of a C5a analog; Example 2 discloses the effect of a C5a analog on MRSA, or methicillin-resistant *S. aureus*; Examples 3-5 provide data establishing the capacity of C5a analogs to directly kill infectious microbes in the form of bacteria, whether organized in a biofilm or not; Example 6 describes the preparation of a controlled-release formulation of C5a analogs; and Example 7 shows the effect of an encapsulated C5a analog on multi-functional memory cytotoxic T-cells. The examples serve only to illustrate the invention and are not intended to limit the scope of the invention in any way.

Example 1

Intranasal Administration of a C-Terminal Analog of C5a Induces Innate Immunity in the Lungs and Enhances Airway Immune Responsiveness The lung possesses a robust ability to induce innate immune responses to inhaled pathogens. Induction is controlled by both the alveolar macrophage (AM) and the bronchial epithelium (BE). Thus, experiments were designed to examine induction of pulmonary innate immunity with EP67.

In short, EP67 (3 mg/kg) was delivered directly to the lungs of mice through insufflation (IN). Animals were sacrificed one day later. Lungs were lavaged with PBS to isolate the bronchoalveolar lavage (BAL) cells for staining and FACS analysis.

Results showed that greater than 90% of the BAL cells isolated from an animal treated with saline alone were AM. This population, defined as large, highly autofluorescent, $CD11b^- CD11^+$, makes up most of the BAL cells in a normal lung. Insufflation of EP67 resulted in the appearance of cells bearing the $CD11b^+CD11c^+$ phenotype of exudate macrophages (exMac). Furthermore, a large population of $CD11b^+$ CD11c⁻ cells appeared in the alveolar space. Further staining indicated that these cells were GR-1⁺ neutrophils (not shown). Analysis of MHCII expression on all cell populations indicated that the CD11c$^{mid}$CD11b$^{hi}$ cells (in the green rectangle) are the myeloid dendritic cells.

The time course of the EP67 response in the BAL cells showed that by seven days post EP67 administration, the neutrophils were largely lost and the AM are again the dominant BAL cell population. The EP67-induced changes in the BAL populations displayed a strict dose-response.

The innate immune response to influenza is initiated with the release of proinflammatory chemokines and the recruitment of neutrophils, lymphocytes, and particularly mononuclear phagocytes into the alveolar air space to limit viral spread. The EP67-induced appearance of neutrophils and exMacs into the alveolar spaces thus mirrored the innate immune response to influenza. However, the innate immune response to influenza is normally delayed for up to 48 hours after infection influenza A, due to the viral nonstructural (NS)1 protein antagonism of host innate immunity.

To test the robustness of the EP67 response, mice were treated at the time of influenza infection. Animals were sacrificed one day later for analysis of BAL cells as above.

BAL cells from the mouse infected with influenza A/PR/8 24 hours earlier showed no induction of innate immunity at the cellular level. The majority of the cells were AM, with no obvious influx of either exMACs or neutrophils. The EP67 treated animals displayed this influx of innate effectors. The animals that were infected with EP67 and simultaneously treated with EP67 showed a similar increase in BAL exMACs and neutrophils to the uninfected animals treated with EP67. These results showed that the EP67 response is not negatively regulated by the viral NS1 protein.

Based on the robust response to EP67 even in the presence of concurrent influenza infection, the ability of EP67 to mitigate influenza pathogenesis was examined. Mice were infected with a non-lethal dose of influenza A/A/PR/8 and treated one time with EP67. Treatment was given either the day before infection, at the time of infection, or on day 1, 2, or 3 after infection. Animals were weighed daily for two weeks to follow disease progression and resolution.

The standard measure for non-lethal influenza morbidity is weight loss of ~20%, with a maximum at about day 8 post-infection, followed by a rapid recovery. This pattern was displayed by the animals that did not receive EP67. Animals that were treated with EP67 either the day before infection or the day of infection lost significantly less weight than the non-treated animals. More surprisingly, the animals treated one day after infection also displayed significant protection from influenza-induced weight loss. Treatment with EP67 on days 2 or 3 after infection, (by which time the host innate immune response has been initiated and viral replication is near its maximum), was not associated with any protection from influenza-induced morbidity. These results indicated that EP67 is able to block influenza-induced illness either prior to infection (i.e., prophylaxis), and following exposure to a productive infection (emergency therapy).

All groups did show some evidence of weight loss at day 8 post-infection. This implied that the viral infection had been reduced but not completely eliminated.

To confirm that productive infection had taken place, an ELISA was performed for anti-influenza antibodies on the serum from these animals. If EP67 had completely blocked infection, there should not have been a strong anti-influenza antibody response. Instead, a high concentration of anti-influenza Abs was found in each group. The results show that EP67 treatment converted a pathogenic infection into a subclinical, immunizing infection. This development of acquired immunity can thus prevent illness following any subsequent exposure to the same organism.

The elderly, who suffer the vast majority of influenza-related morbidity and mortality, have an urgent and currently unmet need for better influenza therapeutics. More than 90% of influenza related deaths are found in the elderly population, making protection of this vulnerable population a critical goal. EP67-mediated protection of the elderly would therefore fill a major unmet health need. Since the aged mouse is considered a strong model for age-related changes in human immunity, the response of aged mice to EP67 insufflation was examined.

EP67 induces a large population of exMACs and neutrophils into the alveolar space in aged lung as in lung. This indicates that EP67 can protect the vulnerable aged population.

Example 2

Control of Methicillin-Resistant *S. aureus* Infection Using a C-Terminal Analog of C5a

*Staphylococcus aureus* is a formidable human pathogen responsible for a variety of disease pathologies ranging from minor skin irritations to more severe infections such as septicemia, necrotizing *pneumonia* and necrotizing fasciitis. The emergence of multi-drug resistant strains of *S. aureus*, including community-acquired methicillin-resistant *S. aureus* (CA-MRSA), has increased the interest in the development of new vaccines and effective treatment strategies.

Using a murine necrotic skin lesion model, the present example demonstrates that administration of EP67 effectively limits CA-MRSA lesion formation and reduces the bacterial load at the site of infection. EP67 treatment resulted in increased cytokine production and neutrophil influx, which was required for controlling disease progression.

Bacterial strains and culture conditions. Methicillin-sensitive *Staphylococcus aureus* (MSSA) laboratory strain ISP479C (Pattee P A., et al., J Bacteriol 1981; 145:479-488) and CA-MRSA USA300 isolate (TCH1516-HOU-MR, ATCC accession number BAA-1717) (Highlander S K, et al., BMC Microbiol 2007; 7:99) were used in this study. Strains were grown aerobically in tryptone soy (TS) broth (Oxoid) at 37° C.

Peptide synthesis. EP67 [YSFKDMP(MeL)aR (SEQ ID NO: 4)] and the inactive control peptide scrambled EP67 (sEP67) [(MeL)RMYKPaFDS (SEQ ID NO: 5)] were synthesized by solid-phase methods as described previously (Taylor S M, Curr Med Chem 2001; 8:675-684). Peptides were purified by analytical and preparative reverse-phase HPLC on C18-bonded silica columns with 0.1% TFA as the running buffer and 60% acetonitrile in 0.1% TFA as the eluant. Peptides were characterized by molecular mass (MH+) with MALDI mass spectrometry.

Mouse model of MRSA demonecrotic infection. All animal work was carried out under the approval of the Office of Laboratory Animal Care (OLAC) at San Diego State University and adhered to accepted veterinary standards. Outbred female CD1 mice 8-12 weeks of age were obtained from Charles River Laboratories. CD88−/− mice were purchased from Jackson Labs. Originally on a heterozygous background, these animals were back-crossed at least 5 times onto the C57Bl/6 background. Prior to infection, hair was removed from the lower backs of mice (n=6-10) using a razor and depilatory cream. Sub-cutaneous *S. aureus* infection was carried out as described previously (Bunce C, et al., Infect Immun 1992; 60:2636-2640). Briefly, 0.1 mL volumes of mid-logarithmic phase MRSA~4×10$^7$ CFU diluted in cytodex bead-DPBS solution were injected sub-cutaneously into the right flank of prepared animals. Where indicated, 250 µg EP67, sEP67 or an equivalent volume of DPBS (50 µL) were injected sub-cutaneously into the right flank 24 h and 4 h prior to and 24 h following bacterial infection. Lesion size was measured on subsequent days using digital calipers. Ulcerative lesions were measured over time, harvested and homogenized using sterile 1 mm ceramic beads. Dilutions of the homogenate were placed on TS agar to enumerate bacterial colony forming units (cfu) per g tissue. Mice (CD1) were rendered neutropenic as described previously (Hoesel L M, et al., Shock 2005; 24:40-47). Briefly, mice were injected intra-peritoneally with rat monoclonal anti-mouse Ly-6G antibody (RB6-8C5, eBioscience) or control rat immunoglobulin (IgG, eBioscience) 24 h prior to EP67 injection and subsequent bacterial infection as described above.

Measurement of cytokines. IL-6, TNF-α, INF-γ and KC inflammatory cytokines were measured in tissue homogenates as previously described using ELISA for IL-6, TNF-α, INF-γ (Morgan E L, et al., Vaccine; 28:8275-8279), or according to manufacturer's protocols (BD and R&D Systems) for KC. Samples were run in triplicate.

Neutrophil chemotaxis and myeloperoxidase assay. Neutrophil recruitment at the site of injection by EP67 or sEP67 was examined using an in vivo chemotaxis assay as described previously (van Sorge N M, et al., PLoS One 2008; 3:e2964). Briefly, 250 µg EP67 or sEP67 were injected subcutaneously into the right flank of CD1 mice. The injection was repeated after 24 h. Mice were euthanized 4 h after the second injection and the site of injection excised for histopathologic analysis or determination of myeloperoxidase (MPO) activity as described previously (van Sorge N M, et al., supra). The assay was carried out two times and the samples analyzed in duplicate.

Statistical analyses. Statistical analysis of results was analyzed by Student's t test using GraphPad Prism version 5. Significance was accepted at P<0.05.

EP67 treatment reduces *S. aureus* cutaneous lesion formation in mice. In order to examine the effects of immunomodulatory peptide EP67 on CA-MRSA disease progression, a mouse model of ulcerative dermal infection was used (Bunce C, Infect Immun 1992; 60:2636-2640). Infection with CA-MRSA strain USA300 resulted in the formation of pus-filled lesions following sub-cutaneous injection with lesions reaching maximum diameter approximately 48-72 h post-infection. Prior to and post-MRSA infection, mice were injected with 250 µg EP67 or the scrambled peptide control, sEP67, as described in above. Disease progression was assessed via measurement of cutaneous lesion development. Lesion size was significantly reduced in animals treated with EP67 48 h post-bacterial inoculation, compared to the sEP67 Animals were sacrificed 5 days post-inoculation and lesion tissue excised and homogenized to determine bacterial CFU present within the lesions. A significant reduction in bacterial load was observed in MRSA-infected animals treated with EP67 compared to those treated with the sEP67 or PBS (data not shown) controls.

Proinflammatory cytokines are enhanced by EP67 treatment. The decrease in lesion size observed in EP67-treated animals indicated an enhanced immune activation in these animals. In order to determine the nature of the immune response activated by EP67 treatment, skin lesions were harvested 48 h post-infection and EP67 or sEP67 treatment, and subjected to ELISA to measure proinflammatory cytokines in tissue homogenates. Significantly higher levels of murine KC (homologue of human chemokine CXCL1) and IL-6 were observed in mice treated with EP67 compared to sEP67. EP67 treatment similarly resulted in an increase of TNF-α and INF-γ production during MRSA infection.

Neutrophil influx is essential for the protective action of EP67. Histopathologic analysis of skin tissue from representative mice revealed normal pathology following injection of PBS or sEP67, but massive influx of inflammatory cells, including neutrophils, following EP67 injection. Neutrophil recruitment to the site of EP67 injection was further analyzed using an in vivo neutrophil recruitment assay as described previously (van Sorge N M, et al., supra; and Banerjee A, et al., Cell Microbiol; 12:1576-1588). Neutrophil migration was assessed in skin homogenates following injection of EP67 or sEP67 by determining the level of neutrophil enzyme myeloperoxidase (MPO), which serves as an effective indication of neutrophil infiltration (Banerjee A, et al., supra; and Bradley P P, et al., J Invest Dermatol 1982; 78:206-209). This method compares well with other in vivo assays of neutrophil chemotaxis (van Sorge N M, et al., supra). MPO levels and therefore the number of accumulating neutrophils were significantly higher after injection with EP67 compared to the sEP67 control.

To further investigate the role of neutrophils in EP67-mediated MRSA lesion reduction, rat monoclonal antibody (MAb) RB6-8C5 was used to induce neutrophil depletion in CD-1 mice 24 h prior to MRSA infection and EP67 treatment. The dose of RB6-8C5 used in this study (25 µg) induced sustained level of neutropenia up to 72 h after injection of the antibody without affecting the population of Ly6G+ dendritic cells or other cell types (Daley J M, et al., J Leukoc Biol 2008; 83:64-70; Stephens-Romero S D, et al., Infect Immun 2005; 73:114-125; and Tvinnereim A R, et al., J Immunol 2004; 173:1994-2002). Consistent with the previous results, there was a significant reduction in lesion size in EP67-treated animals compared to sEP67-treated animals in the groups treated with the isotype IgG control antibody. However, there was no quantifiable difference in lesion size between animals treated with EP67 and sEP67 and with the RB6-8C5 monoclonal antibody. In addition, both groups of neutropenic mice developed significantly larger lesions (P<0.001) than their respective IgG-treated paired control animals. These results indicate that neutrophil infiltration to the site of MRSA infection is essential for the reduction in lesion size mediated by EP67 treatment.

EP67 acts via the C5a receptor CD88. EP67 is a conformationally biased analogue of the C-terminal region of human C5a (Morgan E L, et al., Vaccine 2009; 28:463-469). To examine whether EP67 reduces MRSA infection through a direct interaction with the C5a receptor, CD88, to induce a protective innate immune response, a CD88−/− homozygous C57Bl/6 line, CD88−/− and C57Bl/6 CD88+/+ controls were infected with MRSA sub-cutaneously and treated with EP67 or sEP67 as described in Materials and Methods. As seen previously in CD1 mice, wild-type CD88+/+ animals treated with EP67 had significantly smaller lesions compared to those treated with sEP67. There was no difference in lesion size between the two treatment groups in CD88−/− animals, however, indicating that EP67-mediated protection occurs via binding to CD88. EP67 and sEP67 treated groups in the CD88−/− background developed lesions that were significantly larger than those treated with EP67 in the CD88+/+ background.

Sub-cutaneous injection of EP67 resulted in increased production of pro-inflammatory cytokines TNF-α, INF-γ, IL-6, as well as the neutrophil chemoattractant KC, in skin homogenates during active bacterial infection. Also, EP67 alone, even in the absence of bacteria, promoted the influx of inflammatory infiltrate that included neutrophils, as evidenced by increased levels of MPO and the visual presence of polymorphonuclear cells (PMNs) in skin tissue. The results also clearly show that neutrophil influx contributes to the EP67-mediated defense as depletion of this cell population abrogates the therapeutic effect of EP67.

Example 3

Direct Killing of Bacteria by a C-Terminal Analog of C5a

The following example demonstrates that a C-terminal analogue of C5a known as EP67 (YSFKDMP(MeL)aR (SEQ ID NO: 4)) induces killing of bacteria directly via a bacterostatic/bacteriocidal mechanism.

E. coli strain DH5α was grown overnight in Lennox Broth (LB). This culture was diluted to an optical density at 60 nm ($OD_{600}$) of 0.06. The diluted E. coli was dispensed in 1.5 ml aliquots into separate tubes and 1.5 ml of EP67 (YSFKDMP(MeL)aR (SEQ ID NO: 4)), EP54 (YSFKPMPLaR (SEQ ID NO: 3)), scrambled-EP67 (s-EP67) or scrambled-EP54 in LB was added to obtain a final concentration of 500 μg/ml with the E. coli at an $OD_{600}$ of 0.03. A culture in LB was also prepared. The cultures were incubated at 37° C. with shaking and the $OD_{600}$ readings recorded hourly. In order to determine whether the growth media altered the effectiveness of EP67, LB was replaced with an alternative growth media, Tryptic Soy Broth (TSB).

Results demonstrated that EP67 induces direct bacteriostatic/bacteriocidal effects in the absence of any antigen presenting cells or immune effector cells and that this direct effect is independent of the varying composition of the media the bacteria are grown in.

To test the efficacy of EP67 on bacteria growing in log phase, overnight cultures of DH5α were grown in either LB or TSB. The cultures were diluted to an $OD_{600}$ of 0.03 and incubated at 37° C. with shaking until they reached an $OD_{600}$ of 0.2 at which time either EP67 or s-EP67, in the appropriate media, were added to a final concentration of 500 μg/m. DH5α control cultures (absence of additives) were also prepared. The tubes were further shaken at 37° C. and $OD_{600}$ readings were taken hourly.

The results were consistent with the discussed above; EP67 was shown to significantly reduce and/or stop log phase growth, while s-EP67 demonstrated little or no effect on growth.

S. aureus In Vitro EP67 Killing Curves

150 μl of LB growth medium plus 50 μl of EP67 or s-EP67 were added to individual culture wells resulting in a dilution series of 6 wells per EP67 or s-EP67. A "no EP67" well (control) was included at the end of each series. S. aureus (Newman strain) was allowed to grow to an $OD_{600}$ of 0.4 and each well of the dilution series was inoculated with 5 μl of the culture. Two wells with no bacterial inoculums were included to serve as controls. Plates were incubated at 37° C. with agitation and the $OD_{600}$ of each well was measured hourly using a plate reader.

The results showed a dose dependent inhibitory effect of EP67 on bacterial growth at higher concentrations used in the experiment.

Example 4

Effect of a C-Terminal Analog of C5a on Group B Streptococcus (GBS) Meningitis

In this study, EP67 was used to demonstrate the ability to induce host innate immune responses that are protective to a bacterial infection common in the central nervous system (CNS) via administration at a site distal to the CNS.

8-week-old female CD1 mice were treated with 250 μg of EP67 or s-EP67 at day −1, 0, 1 and 2 via i.p. injection. GBS was injected i.p. at $1 \times 10^9$ cfu/mouse. Brains and blood were harvested from each mouse 96 hours post-injection. The tissue was homogenized, diluted and plated to determine the cfu/g bacteria.

The results demonstrated that EP67 induces a robust host innate immune response that protects against GBS infections in the central nervous system. These results indicate that EP67 (and related analogues) can be used to invoke protective innate immunity in immune-privileged sites and further support its use as an immunotherapeutic for systemic pathogenic infections.

Example 5

Effect of a C-Terminal Analog of C5a on Bacterial Burden of a Biofilm

In this study, EP67 was used to demonstrate the ability to induce host innate immune responses capable of eliminating/reducing bacterial burden of a biofilm associated with a catheter.

A S. aureus (USA300 LAC strain) biofilm was established on a hollow catheter (1 cm in length) inserted subcutaneously into C57BL/6 mice by introducing 1000 CFUs of S. aureus into the catheter lumen. At the time of infection, one dose of EP67 (200 μg/ml dissolved in PBS) was introduced. At both 24 and 48 h following infection, a series of four injections of EP67 were made; two into each open end of the catheter (20 μl each) and two along the top and bottom at points perpendicular to the middle of the catheter (50 μl each). Samples of the biofilm and surrounding tissue were obtained at Day 3 and assessed for the presence of viable bacteria by standard culture methods. Mice treated with EP67 exhibited a significant decrease in bacterial burdens within the biofilm and surrounding tissue relative to mice treated with the inactive, scrambled EP67 (sEP67) and PBS vehicle.

Example 6

Preparation of Controlled-Release Formulations of C5a Analogs

Poly (lactic acid-co-glycolic acid)-EP67 (PLGA-EP67) microspheres were produced by a co-solvent emulsification/solvent evaporation (ESE) method optimized for peptides.[1] PLGA, 50:50, 0.38 dL/g i.v. (Lactel), was dissolved by adding DCM (dichloromethane, 0.90 mL, Sigma) to an 8 mL glass vial containing PLGA (350 mg). The peptide (EP67) was dissolved by adding methanol (MeOH, 0.315 mL, Sigma) to a 2 mL glass vial containing peptide (17.5 mg). Vials were capped during dissolution. After PLGA and EP67 were completely dissolved in their respective solvents, the MeOH solution of EP67 was pipetted into the DCM solution of PLGA and the capped vial was swirled until the co-solvent oil (0) phase was homogeneous by visual inspection.

The microsphere hardening bath was a 600 mL beaker containing 200 mL of water phase consisting of 1% polyvinyl alcohol (PVA, MW: 31,500, Sigma) and 0.1 M NaCl. The bath was stirred (Thermo Scientific Cimerac stirring plate) at the indicated RPM using an octagonal stirring bar (5×1 cm, 9.5 g). When supplemental $N_2$ flow was used, the flow was directed at the center of the emulsion surface at a height that did not distort the emulsion surface (12 cm). The flow rate of $N_2$ was regulated by an in-line gas flow meter (0-1.0 L/min or 0-40 L/min, Gilmont Industries).

Water phase (W, 1 mL) was withdrawn from the hardening bath and pipetted into the oil phase. The recapped vial was vortexed at setting 10 (Vortex Genie) for 30 seconds to form the initial O/W emulsion. The microsphere hardening step was fully initiated by pouring the initial O/W emulsion into the hardening bath. After 5 seconds of stirring, the final O/W emulsion was weighed (Adam centigram balance) then stirred continuously at the indicated RPM (with specified $N_2$ flow rate) and subsequently weighed at periodic intervals for gravimetric analysis of the solvent evaporation rate.

The hardened microspheres were allowed to settle and the water phase was decanted. Remaining visible water phase was removed from the slurry. The slurry was dried by brief vacuum filtration (0.2 μm Nylaflo filter), then resuspended in $dH_2O$ (1 mL) and dried again by vacuum filtration (3×). Rinsed, dried slurry was resuspended in $dH_2O$ (2 mL), transferred to a pre-weighed 100 mL beaker, flash-frozen by submerging the beaker in liquid nitrogen, and lyophilized directly in the 100 mL beaker for 24 hours.

Lyophilized samples were stored in capped, Parafilm-sealed 20 mL glass scintillation vials at −20° C. Microsphere diameters and encapsulation efficiencies at 5% theoretical EP67 loading (wt EP67/total wt) were the same under each formulation condition (diameter [P=0.9986], encapsulation efficiency [P=0.1786], n=2 independent preparations) and, as a consequence, did not vary with the solvent evaporation rate (SER) (microsphere diameter P=0.1509; EP67 encapsulation efficiencies P=0.3224) (FIG. 1). Thus, the range of stirring rates had no effect on subsequent microsphere diameters or peptide loading under the current co-solvent O/W formulation.

Figure 2:
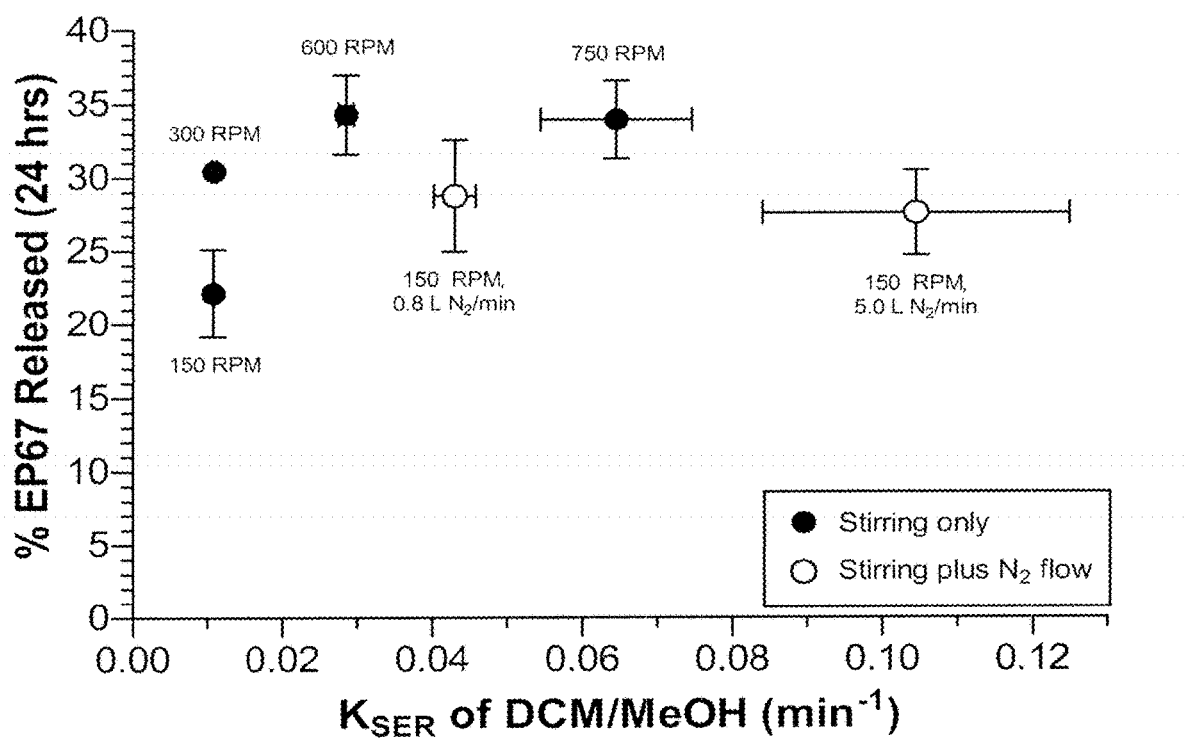
FIG. 2. Relationship between the solvent evaporation rate during microsphere hardening and EP67 burst release. Average cumulative percentages of EP67 released from the microspheres after 24 hours (burst release)±SD (n=2 preparation per formulation condition) are shown. First-order rate constants, $K_{SER}$ (min$^{-1}$)±propagated error (95% CI, n=2 independent preparations) for DCM/MeOH evaporation during microsphere hardening were calculated by fitting a one-phase exponential decay rate equation directly to the first 0.6 g of mass loss from the final O/W emulsion with constraints to start at the origin and converge at 1.3 g of mass loss (the average combined mass of DCM/MeOH transferred to the final O/W emulsion).

Increasing the SER about 6-fold over the range of stirring rates increased EP67 burst release a maximum of 12% (22±3% (SD) at 150 RPM vs. 34±3% at 750 RPM, P<0.001, n=2 independent preparations) (FIG. 2) with the majority of burst release occurring after resuspension. Although the SER was the same at 150 RPM and 300 RPM, EP67 burst release from microspheres prepared at 300 RPM was 8% greater than from microspheres prepared at 150 RPM (30.4±0.7% (SD) vs. 22±3% EP67 released after 24 hrs, P<0.001, n=2 independent preparations) (FIG. 2, 150 and 300 RPM, closed circles). These results indicate that the stirring rate of the final emulsion can increase peptide burst release from subsequent microspheres independently of the SER under the current co-solvent O/W formulation.

Given that both the SER and peptide burst release increased at higher stirring rates (FIG. 2, closed circles), it remained possible that the SER contributes to an increase in peptide burst release at higher stirring rates. To determine whether the SER increases peptide burst release independently of the stirring rate, microspheres were prepared at the lowest stirring rate/SER (150 RPM) and the SER was increased by flow rate of $N_2$ gas over the surface of the final emulsion. Gas flow was directed from a height that did not affect the surface of the final O/W emulsion at the highest flow rate (5.0 L $N_2$/min). Furthermore, the ability to gravimetrically determine the SER with $N_2$ purge by a direct first-order fit was confirmed at the highest flow rate (5.0 L $N_2$/min) in the same manner as the stirring rate.

Increasing the SER of DCM/MeOH 10-fold by $N_2$ flow rate had no effect on subsequent microsphere diameters (FIG. 1, indicated circles) or EP67 loading (FIG. 1, indicated squares) and increased EP67 burst release from subsequent microspheres a maximum of only 6% (22±3% (SD) at 0 L $N_2$/min vs. 28±3% EP67 burst release at 5.0 L $N_2$/min at 150 RPM, P<0.001, n=2 independent preparations) (FIG. 2, open circles) compared to a maximum of 12% by stirring rate (FIG. 2, closed circles). These results indicate that increasing the SER by flow rate of $N_2$ gas increases peptide burst release from subsequent microspheres independently of, but to a lesser extent than, the stirring rate of the final emulsion under the current co-solvent O/W formulation.

Example 7

Figure 3:
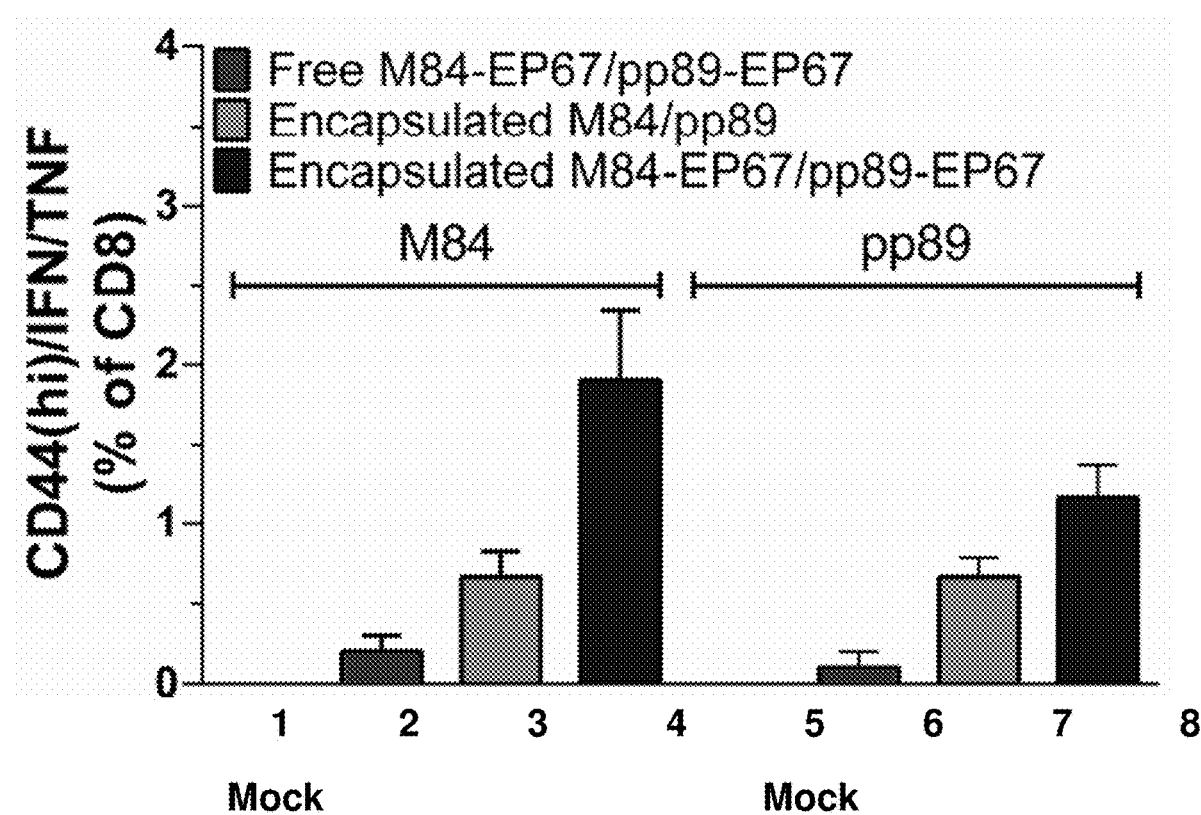
FIG. 3. Effect of encapsulation on the recruitment of systemic memory Cytotoxic T Lymphocytes (CTL) by M84-EP67/pp89-EP67. These data indicate that (a) SQ administration of M84-EP67/pp89-EP67 recruits multifunctional memory CTL (bars 2 and 6) and (b) encapsulation of M84-EP67/pp89-EP67 (bars 4 and 8) increases memory CTL recruitment over free M84-EP67/pp89-EP67 (bars 1 and 5) and encapsulated epitopes (bars 3 and 7). Methods: Two partially protective mouse cytomegalovirus (MCMV) CTL epitopes identified in the BALB/c strain, M84 ($^{297}$AY-AGLFTPL$^{305}$, SEQ ID NO: 19) and pp89 ($^{68}$YPHFMPTNL$^{76}$, SEQ ID NO: 20), were attached to the N-terminal of EP67 via a protease-labile double arginine (M84-EP67 and pp89-EP67). Naïve female BALB/c mice were injected SQ with PBS (Mock), free M84-EP67/pp89-EP67 (red bars, 62.5 µg each peptide in PBS), encapsulated M84/pp89 (green bars; PLGA 50:50 microspheres, about 20 µm in diameter) or encapsulated M84-EP67/pp89-EP67 (blue bars; PLGA 50:50 microspheres about 20 µm in diameter) and boosted on day 21. Splenocytes were isolated on day 28 and incubated with M84 or pp89 (1 µM) and 10 µg/mL brefeldin A for 6 hours at 37° C. Cells were surface-stained for CD8α and CD44, fixed, permeabilized, and stained for IFN-γ and TNF-α. Lymphocytes were gated on SSC/FSC, then on CD8+/CD44(hi) that were positive for both IFN and TNF and expressed as mean % of total CD8 (n=3 mice).
Figure 4:
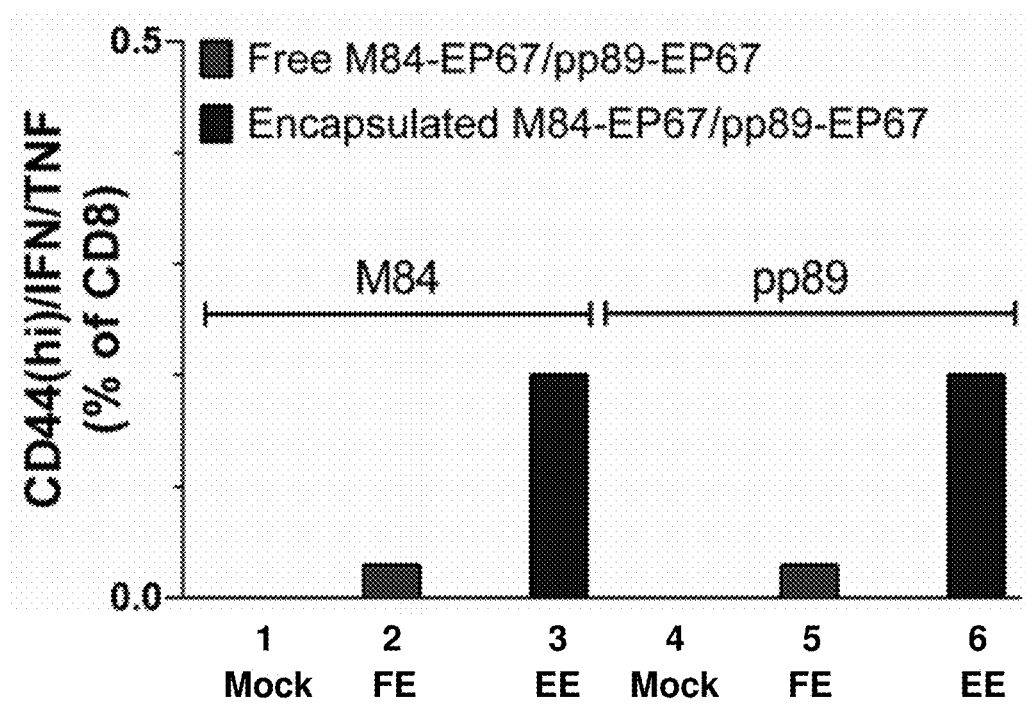
FIG. 4. Recruitment of lung effector memory CTL by CMV-EP67 administered IN. These data indicate that (a) Intranasal instillation (IN) administration of M84-EP67/pp89-EP67 recruits multifunctional effector memory CTL to the lungs (bars 2 and 5) and (b) encapsulation of M84-EP67/pp89-EP67 increases the recruitment of multifunctional memory CTL (bars 3 and 6) over free M84-EP67/pp89-EP67 (bars 2 and 5) and encapsulated epitopes (EE). Mock controls are also shown (bars 1 and 4). Methods: Naïve mice were immunized on days 0, 5, 10, and 15 with PBS, M84/pp89 (FE: 60 µg, 1:1), M84-EP67/pp89-EP67 (Red bars: 60 µg, 1:1), encapsulated M84/pp89 (EE: 30 µg, 1:1; 6 µm diam.) or encapsulated M84-EP67/pp89-EP67 (Blue bars: 30 µg 1:1; 6 µm diam.) under light isoflurane anesthesia. Lung cells were isolated on day 20, stimulated with either pp89 or M84 (1 µM) in presence of 10 µg/mL brefeldin A (in 100 µl media) for 6 hours at 37 C/5% CO2. Cells were surface stained for CD8a, CD44, fixed, permeabilized and stained for IFN-γ and TNF-α. Lymphocytes were gated based on SSC/FSC then on CD8+/CD44(hi) positive for both IFN and TNF and expressed as mean % of total CD8 (n=5 mice).

Effect of Encapsulating an EP67-Based Vaccine on Recruitment of Multifunctional, Systemic and Mucosal Memory CTL Two partially protective murine cytomegalovirus (MCMV) CTL epitopes identified in the BALB/c strain, M84[26] ($^{297}$AYAGLFTPL$^{305}$, SEQ ID NO: 19) and pp89[27] ($^{68}$YPHFMPTNL$^{76}$, SEQ ID NO: 20), were attached to the N-terminus of EP67 via a protease-labile double arginine (M84-EP67 and pp89-EP67). M84-EP67, pp89-EP67, M84, and pp89 were individually encapsulated in microspheres by the co-solvent emulsification/solvent evaporation method and co-administered subcutaneously (SQ, 62.5 μg each peptide days 0, 14) or intranasally (IN, 30 μg each peptide on days 0, 5, 10, and 15). Multifunctional memory CTL (i.e., secrete more than one cytokine) were recruited by SQ injection and IN instillation of free M84-EP67/pp89-EP67 (FIGS. 3 and 4, red bars). In contrast to free M84-EP67/pp89-EP67 (FIGS. 3 and 4, red bars) or M84/pp89 encapsulated in 20 μm microspheres (FIG. 3, green bars) or 6 μm microspheres (FIG. 4, "EE"), M84-EP67/pp89-EP67 encapsulated in 20 μm (FIG. 3, blue bars) or 6 μm (FIG. 4, blue bars) microspheres recruited the highest percentage of multifunctional memory CTL. Thus, given that levels of multifunctional memory CTL correlate with decreased viral load in patients naturally infected with viruses[28], encapsulation is expected to increase the efficacy of this and other C5a-analog-based (e.g., EP67-based) vaccines.

Example 8

Evaluation of Mucin Epitope (MUC1/C5a Agonist) Conjugate for Recruitment and Activation of Antigen Presenting Cells (APCs) and Stimulation of an Immune Response in Mice The C5a receptor is present on numerous antigen-presenting cells, including monocytes, macrophages, dendritic cells, and other cell types. In this Example, a composite peptide comprising a mucin epitope (MUC1) functionally linked to a decapeptide agonist analog of C5a corresponding to the C-terminal effector region of the natural factor was evaluated for its ability to activate the APCs thereby stimulating an immune response in mice. This evaluation is based on the known property of C5a receptors to internalize and recycle in the antigen-presenting cell, thereby acting as ideal candidates for delivering antigens to, and simultaneously activating signals in, the APCs. Because C5a receptors are particularly common on macrophages, monocytes and dendritic cells, the use of a C5a agonist analog to bind C5a receptors is expected to result in preferential activation of these ACPs.

Abbreviations. Except where noted, the single letter designation for the amino acid residues is used: alanine is A; arginine is R; asparagine is N; aspartic acid is D; cysteine is C; glutamine is Q; glutamic acid is E; glycine is G; histidine is H; isoleucine is I; leucine is L; lysine is K; methionine is M; phenylalanine is F; proline is P; serine is S; threonine is T; tryptophan is W; tyrosine is Y; and valine is V. Upper case letters represent the L-amino acid isomer and lower case letters represent the D-isomer.

Peptide Synthesis, Purification and Characterization. The following peptides were synthesized according to standard solid-phase methodologies on an Applied Biosystems (Foster City, Calif.) model 430 A peptide synthesizer and characterized as previously described (7): (1) The antigenic "juxta-membrane" (JM) epitope of the human mucin-1 (MUC1), YKQGGFLGL (SEQ ID NO: 21); (2) The C5a C-terminal decapeptide agonist analog, YSFKPMPLaR (SEQ ID NO: 3); (3) The composite peptide YKQGGFLG-LYSFKPMPLaR (SEQ ID NO: 23), in which the JM epitope is positioned toward the amino terminus and the C5a peptide is positioned toward the carboxyl terminus; and (4) The composite peptide YSFKPMPLaRKQGGFLGL (SEQ ID NO: 24), in which the JM epitope of MUC1 is positioned toward the carboxyl terminus and the C5a analog is positioned toward the amino terminus. Peptide 3 retains C5a biological activity, whereas peptide 4 does not because the biologically important carboxyl terminal end of the C5a analog is blocked by the presence of the mucin epitope. As such, peptide 4 serves as a control to determine the importance of C5a biological activity to the effectiveness of these peptides for immunization purposes.

Syntheses were performed on a 0.25 mmol scale on 0-hydroxymethylphenoxymethyl polystyrene (HMP) resins (0.88 meq/g substitution). N-amino groups were protected with the base-labile 9-fluorenylmethyloxycarbonyl (Fmoc) group. Side-chain functional groups were protected as follows: Arg (Pmc or 2,2,5,7,8-pentamethylchroman-6-sulfonyl); Asp (O-t-butyl ester); Cys, Gln & His (Trt or trityl); Lys (Boc or t-butyloxycarbonyl); Ser & Tyr (t-butyl). Synthesis was initiated by the in situ coupling of the C-terminal residue ($N^{\alpha}$-Fmoc-L-Arg(Pmc)) to the HMP resin in the presence of excess N—N'-dicyclohexylcarbodiimide (DCC) and 1-hydroxybenzotriazole (HOBT) with 4-dimethylaminopyridine (DMAP) as a coupling catalyst. Peptide chain elongation was accomplished by repetitive Fmoc deprotection in 50% piperidine in NMP followed by residue coupling in the presence of 2-(1H-benzotriazol-1-yl)-1,1,3,3-tetramethyluronium hexafluorophosphate (HBTU).

Side-chain deprotection and cleavage from the resin were achieved in a single-step acetolysis reaction by stirring the peptide resin in a solution of 84% trifluoroacetic acid (TFA), 6% phenol, 2% ethanedithiol, 4% thioanisole, and 4% water for 1.5 hours at room temperature. Free peptide was precipitated from this solution by adding cold diethyl ether. The mixture was filtered through a sintered glass Buchner funnel (medium porosity) and the peptide/resin was washed twice with cold ether to remove the thiol scavenger. The peptide was extracted by swirling the peptide/resin in the funnel with 20-30 ml aliquots of 10% acetic acid followed by filtration. The extraction aliquots were combined, frozen, and lyophilized to yield the powdered form of the crude peptide.

Peptides were purified by preparative and analytical reverse-phase HPLC on columns packed with $C_{18}$-bonded silica. The details of this procedure have been described (4). All peptides were characterized by amino acid compositional analysis and fast atom bombardment mass spectrometry (FAB-MS).

Animal Models. The strains of mice used in the studies described in this Example were inbred 6- to 12-week-old C57B16($H-2_b$) and Balb/c ($H-2_4$) females obtained from Jackson Labs (Bar Harbor, Me.). These two strains, which differ in H-2 haplotypes, were used in these studies to demonstrate that the observed antibody responses were not a result of the selection or creation, in one mouse strain or the other, of a unique immunogenic epitope characteristic of the sequence of the proteins of the MHC class I and class II molecules important for antigen processing. The MUC1 peptide selected for these studies contained a motif that may bind to the $H-2K_b$ molecule of the C57B16 mice. Therefore, a strain of mouse that lacked this class I molecule-binding motif (Balb/c) was also studied to determine the relative contribution of the class I-binding motif to the antigen presentation properties of these peptides.

Immunization Protocol. Preimmune sera were obtained from mice, which were subsequently immunized intraperitoneally with 100 µg of the indicated peptide with RIBI adjuvant (MPL+TDM+CWS) (Sigma Immunochemicals). Animals were boosted twice at two-week intervals using the same injection procedure. Sera were obtained following three immunizations (at 6 weeks).

Analysis of Serum Antibody Responses. For radioimmunoassay (RIA), anti-peptide antibodies were determined, before and at different time points after immunization, in 96-well microtiter plates (Dynatech Laboratories, Inc.). Plates were coated with 50 µl of a 100 µg/ml appropriate peptide in phosphate-buffered saline (PBS) pH 7.4 solution overnight at 4° C. The wells were blocked by incubation with 5% dry milk in PBS pH 7.4 for at least two hours. Anti-peptide antibody titers were determined using serial dilutions of sera. The sera were diluted with PBS containing 0.05% Tween-20, pH 7.4 (washing buffer) and 50 µl of each dilution was incubated at 37° C. for 1 hour. The wells were then drained, washed 4 times with PBS-Tween and 50 µl of $^{125}$I-goat anti-mouse antibody ($1-2\times10^4$ cpm/well) was added and incubated for 1 hour at 25° C. After washing, specific radioactivity was recorded in a gamma counter (1272 CliniGamma, LKB).

Anti-peptide antibody isotype titers were determined by enzyme-linked immunosorbent assay (ELISA) carried out in 96-well microtiter plates. The plates were coated with 100 µg/ml of appropriate peptide in PBS, pH 7.4, and incubated overnight. The wells were blocked with 5% dry milk in PBS pH 7.4 for at least two hours. Anti-peptide titers were determined using serial dilutions of sera. After the plates were washed 4 times, 50 µl of a 1:100 dilution of rabbit anti-mouse IgA, IgG1, IgG2a, IgG2b, IgG3 and IgM (Zymed) was added to each well and incubated at 25° C. for 1 hour. The plates were washed 4 times with washing buffer and 50 µl of 1:500 goat anti-rabbit conjugated to peroxidase (Zymed) was incubated at 37° C. for 1 hour. Again, the plates were washed 4 times with washing buffer and bound enzyme was detected by the addition of 50 µl 1 mg/ml p-nitrophenyl phosphate (Sigma) in 10% diethanolamine (Sigma) pH 9.4. The reaction was stopped by the addition of 50 µl of 0.5 M sodium hydroxide and absorbance values ($A_{405}$) were determined using Titertek Multiskan (Flow Laboratories, Irvine, Scotland).

Experimental Groups. Experimental groups were as follows: Group A mice were immunized with peptide (1); Group B mice were immunized with peptide (2); Group C mice were immunized with peptide (1) plus peptide (2); Group D mice were immunized with peptide (3); and Group E mice were immunized with peptide (4).

The results showed that the mice in Groups A, B, C and E produced no appreciable increase in antibody response to inoculation with MUC1 epitope (Group A), C5a agonist peptide (Group B), MUC1 epitope combined with, but not conjugated to, C5a agonist peptide (Group C), or MUC1 epitope conjugated to the C5a agonist peptide at its C-terminus, rather than its N-terminus (thereby blocking C5a biological activity) (Group E). Only mice inoculated with the MUC1 epitope/C5a agonist peptide conjugate (Group D) generated an appreciable antibody response. Furthermore, this stimulation was significant. It is clear from these results that inoculation with the conjugated MUC1 epitope/C5a agonist peptide was far more efficient in stimulating a general immune response (i.e., production of antibodies) than was inoculation with either peptide alone, or both peptides together but not conjugated, or peptides conjugated in the opposite orientation.

The results revealed that both Balb/c and C57B16 mice showed antibody responses to peptide 3, which indicated that the antigen-presenting effect was not restricted by MHC haplotype. The fact that immune responses were not produced to peptide 4, or to mixtures of peptide 1 and 2, but that substantial responses were produced to peptide 3, establish that the effect is mediated by the C5a moiety of the peptide and that the immune response results from the simultaneous delivery of antigen peptide and C5a-mediated activation signals to antigen presenting cells.

The isotypes of the anti-peptide antibodies produced in the immunized mice were determined and were found to consist of IgM, IgG2a, and IgG2b. This indicates that the immunogenic peptide is producing T cell-dependent responses, which generally require antigen processing and presentation. The data showed that the antibody response to peptide 3 included a high percentage of antibodies that were specific for the MUC1 epitope that was the antigen moiety of these studies.

Example 9

Evaluation of Serum Amyloid A/C5a Peptide Conjugates on APCs and Immune Response Serum amyloid A (SAA) is an acute-phase stress response protein generated by the liver. Along with other acute-phase proteins, SAA is secreted in response to systemic inflammatory stress as a protective measure. SAA is appears to be an excellent indicator of general, systemic inflammation, which is a phenomenon that is very difficult to quantitate. Because serum levels of SAA have been observed to parallel the rise and fall of the systemic inflammatory response, quantitation of serum levels of this peptide would provide an effective means of assessing inflammation. One way to assess inflammation is to develop antibodies against SAA that could be used for quantitation, such as in an ELISA assay. SAA has weak immunogenic properties, however. In this Example, an evaluation was made of the ability of SAA conjugated to a C5a C-terminal analog (as described in Example 1) to activate antigen-producing cells and to produce an antibody response in rats.

Production and Preparation of Proteins and Peptides. The C-terminal C5a analog K-Ahx-YSFKPMPLaR (SEQ ID NO: 25) (AhX is aminohexanoic acid, which is a linear aliphatic spacer moiety) was produced as described in Example 8. The aliphatic spacer moiety was included to separate the receptor-binding domain of the C5a analog from the bulky protein to be attached at the amino terminus of the analog.

Serum amyloid A was conjugated to the C5a peptide analogs according to the following method. SAA (100 μg) was reacted with a 50-fold molar excess of a water-soluble carbodiimide, 1-(3-dimethylaminopropyl)-3-ethylcarbodiimide methiodiide (EDC), in 200 μl of phosphate-buffered saline, pH 7.5, at room temperature for 30 minutes. A 50-fold molar excess of the peptide (K-Ahx-YSFKPM-PLaR) (SEQ ID NO: 25) and a 100-fold molar excess of a base diisopropylethyl amine (DIEA) were added to this solution. Water was added to the solution to bring the reaction mixture to a volume of 400 μl. This solution was stirred overnight at room temperature and then lyophilized to a dry powder. The powder was dissolved in the appropriate volume of water to generate the stock mixture used for inoculating the animals.

Experimental Protocols. Rats were injected intraperitoneally with an inoculant comprising the SAA/C5a peptide conjugates in phosphate-buffered saline with or without RIBI adjuvant (monophosphoryl-lipid A/trehalose dicorynomycolate). Booster injections were given two and five weeks after the initial injections. The rats were sacrificed seven weeks after the initial injection and anti-mucin antibody production was assessed from the serum titers.

Significant anti-SAA antibody was produced from both groups of rats, whether or not RIBI adjuvant was included in the inoculation. As visualized by gel electrophoresis and autoradiography of anti-SAA antibody eluted from the plate assays, anti-SAA antibody titers were essentially equivalent, or slightly higher, in rats inoculated with SAA/C5a peptide conjugate in the absence of RIBI adjuvant as compared to the same inoculation without the adjuvant. Thus, antigenic conjugates comprising the C5a peptide analog are useful for generating antibodies against large proteins, as well as against smaller peptide fragments. Moreover, the successful generation of anti-SAA antibodies utilizing this method is particularly promising for purposes of producing antibodies against weakly antigenic or non-antigenic peptides or proteins.

Example 10

Comparison of Immunogenicity of Epitope-C5a Agonist Constructs with Epitope-KLH Conjugates The following experiment was performed in order to compare the potency of a C5a conjugate for use in the controlled-release formulations disclosed herein with a keyhole limpet hemocyanin (KLH) conjugate widely used in methods for enhancing the immune response to peptide epitopes. The objective was a direct comparison of the response to a construct of MUC1 epitope-C5a and the same epitope conjugated to KLH in mice. Each of the conjugates was administered to mice and the immune responses were assessed by measuring antibodies produced using the protocols generally described in Examples 8 and 9 employing techniques known in the art. In brief, sera were screened against MUC1 peptide and mean titer values of responders recorded in Table 1. Parentheses in Table 1 indicate the number of responders. Antibody titer was defined as the sera dilution within the linear range at which specific reactivity is lost. Five C57BL mice were immunized and boosted with YKQGG FLGLYSFKPMPLaR (SEQ ID NO: 23) and five C57BL mice were immunized and boosted with YKQGGFLGL-KLH (SEQ ID NO: 21 conjugated to KLH (keyhole limpet hemocyanin)). Sera were obtained using conventional methods (see generally Examples 8 and 9). Standard error of responder titer values immunized with MUC1 epitope-C5a was less than 32% for all isotypes; standard error of responder tilter values for mice immunized with MUC1 epitope-KLH was less than 25% for IgM and less than 40% for IgG1. Results, summarized in Table 1, showed that the C5a conjugate induced a more diverse and robust immune response than the standard KLH conjugate, supporting use of the C5a conjugates in the controlled-release formulations according to the disclosure.

TABLE 1

MUC1-Specific Antibody Isotype Tilters Produced with Different Immunogens.
Ab Isotypes and Titers

| Peptide | MUC1 Specific Antibody Isotype Titers Produced with Different Immunogens. Antibody Isotypes and Titers | | | | | |
|---|---|---|---|---|---|---|
| | IgA | IgG1 | IgG2a | IgG2b | IgG3 | IgM |
| YKQGGFLGLYSFKPMPLaR (SEQ ID NO: 23) | 0 | 0 | 1260 (5/5) | 1780 (5/5) | 0 | 6310 (5/5) |
| YKQGGFLGL-KLH (SEQ ID NO: 21-KLH) | 0 | 100 (2/5) | 0 | 0 | 0 | 5010 (4/5) |

A similar experiment was performed in rabbits. The immunogens used in rabbits were the κ- and μ-opioid receptor epitopes, FPGWAEPDSNGSAGSEDAQL (SEQ ID NO: 26) and GDLSDPCGNRTNLGGRDSL (SEQ ID No: 27), respectively. The serum antibody titer and antibody subtypes produced in rabbits injected with the two compositions containing the different immunogens were compared.

Peptide Conjugates. In one instance, the epitopes were conjugated to KLH via a lysine residue added synthetically to the N-terminus of the epitope along with an alanine residue which acted as a spacer. In this experiment, glutaraldehyde was used to effect conjugation. In the another case, the epitopes were linked to the N-terminal end of the C5a agonist YSFKPMPLaR (SEQ ID NO: 3) using the solid-phase peptide synthetic methodologies described above in example 8.

Immunization Protocol for Rabbits. Rabbits were immunized s.c. with 500 µg of either the epitope-KLH or the epitope-C5a analog (epitope-SEQ ID NO: 1) constructs in compete Freund's adjuvant (GIBCO, Grand Island, N.Y.). Booster injections were administered on days 30 and 60 in incomplete Freund's adjuvant. Serum was collected starting at day 60 post-immunization.

Antibody Determination. The presence of rabbit IgG specific for the peptide epitopes was determined by ELISA as previously described (8).

Rabbits immunized with the epitope-C5a analog generated high-titer IgG antibodies specific for the opioid receptor peptide epitopes. The rabbits immunized with the opioid receptor epitopes conjugated to the carrier protein KLH also produced high-titer antibodies specific for the epitopes with which they were injected. These results demonstrate that the decapeptide C5a-analog was as effective as the large molecular weight protein, KLH, conjugated to the epitope at inducing specific anti-peptide antibodies in non-rodent species.

REFERENCES

Sato, A. K., Viswanathan, M., Kent, R. B. & Wood, C. R. Therapeutic peptides: technological advances driving peptides into development. *Current opinion in biotechnology* 17, 638-642 (2006).

Stevenson, C. L. Advances in peptide pharmaceuticals. *Curr Pharm Biotechnol* 10, 122-137 (2009).

Nestor, J. J., Jr. The medicinal chemistry of peptides. *Curr Med Chem* 16, 4399-4418 (2009).

Vlieghe, P., Lisowski, V., Martinez, J. & Khrestchatisky, M. Synthetic therapeutic peptides: science and market. *Drug discovery today* 15, 40-56 (2010).

Kontermann, R. E. Strategies for extended serum half-life of protein therapeutics. *Curr Opin Biotechnol* 22, 868-876 (2011).

Brown, L. R. Commercial challenges of protein drug delivery. *Expert Opin Drug Deliv* 2, 29-42 (2005).

Antosova, Z., Mackova, M., Kral, V. & Macek, T. Therapeutic application of peptides and proteins: parenteral forever? *Trends Biotechnol* 27, 628-635 (2009).

Degim, I. T. & Celebi, N. Controlled delivery of peptides and proteins. *Curr Pharmaceut Design* 13, 99-117 (2007).

Langer, R. & Moses, M. Biocompatible controlled release polymers for delivery of polypeptides and growth factors. *Journal of cellular biochemistry* 45, 340-345 (1991).

Ye, M., Kim, S. & Park, K. Issues in long-term protein delivery using biodegradable microparticles. *J Control Release* 146, 241-260 (2010).

Singh, M., Singh, O. & Talwar, G. P. Biodegradable delivery system for a birth control vaccine: immunogenicity studies in rats and monkeys. *Pharm Res* 12, 1796-1800 (1995).

Ertl, H. C. et al. Poly (DL-lactide-co-glycolide) microspheres as carriers for peptide vaccines. *Vaccine* 14, 879-885 (1996).

Nixon, D. F. et al. Synthetic peptides entrapped in microparticles can elicit cytotoxic T cell activity. *Vaccine* 14, 1523-1530 (1996).

Partidos, C. D., Vohra, P., Jones, D., Farrar, G. & Steward, M. W. CTL responses induced by a single immunization with peptide encapsulated in biodegradable microparticles. *Journal of immunological methods* 206, 143-151 (1997).

Newman, K. D., Sosnowski, D. L., Kwon, G. S. & Samuel, J. Delivery of MUC1 mucin peptide by Poly(d,l-lactic-co-glycolic acid) microspheres induces type 1 T helper immune responses. *J Pharm Sci* 87, 1421-1427 (1998).

Moynihan, J. S., Jones, D. H., Farrar, G. H. & Howard, C. R. A novel microencapsulated peptide vaccine against hepatitis B. *Vaccine* 19, 3292-3300 (2001).

Rosas, J. E. et al. Biodegradable PLGA microspheres as a delivery system for malaria synthetic peptide SPf66. *Vaccine* 19, 4445 (2001).

Jiang, W., Gupta, R. K., Deshpande, M. C. & Schwendeman, S. P. Biodegradable poly(lactic-co-glycolic acid) microparticles for injectable delivery of vaccine antigens. *Adv Drug Deliv Rev* 57, 391-410 (2005).

Wei, H. J. et al. Gelatin microspheres encapsulated with a nonpeptide angiogenic agent, ginsenoside Rg1, for intramyocardial injection in a rat model with infarcted myocardium. *J Control Release* 120, 27-34 (2007).

Nishikawa, T. et al. Development of a novel antimicrobial peptide, AG-30, with angiogenic properties. *Journal of cellular and molecular medicine* 13, 535-546 (2009).

Benny, O. et al. Continuous delivery of endogenous inhibitors from poly(lactic-co-glycolic acid) polymeric microspheres inhibits glioma tumor growth. *Clin Cancer Res* 11, 768-776 (2005).

Benny, O. et al. In vivo fate and therapeutic efficacy of PF-4/CTF microspheres in an orthotopic human glioblastoma model. *Faseb J* 22, 488-499 (2008).

Wang, Y., Wan, C., Szoke, G., Ryaby, J. T. & Li, G. Local injection of thrombin-related peptide (TP508) in PPF/PLGA microparticles-enhanced bone formation during distraction osteogenesis. *Journal of orthopaedic research: official publication of the Orthopaedic Research Society* 26, 539-546 (2008).

Torchilin, V. P. Drug targeting. *Eur J Pharm Sci* 11 Suppl 2, S81-91 (2000).

Luan, X., Skupin, M., Siepmann, J. & Bodmeier, R. Key parameters affecting the initial release (burst) and encapsulation efficiency of peptide-containing poly(lactide-co-glycolide) microparticles. *Int J Pharm* 324, 168-175 (2006).

Holtappels, R., Thomas, D. & Reddehase, M. J. Identification of a K(d)-restricted antigenic peptide encoded by murine cytomegalovirus early gene M84. *J Gen Virol* 81, 3037-3042 (2000).

Reddehase, M. J., Rothbard, J. B. & Koszinowski, U. H. A pentapeptide as minimal antigenic determinant for MHC class I-restricted T lymphocytes. *Nature* 337, 651-653 (1989).

Seder, R. A., Darrah, P. A. & Roederer, M. T-cell quality in memory and protection: implications for vaccine design. *Nat Rev Immunol* 8, 247-258 (2008).

The disclosed subject matter has been described with reference to various specific and preferred embodiments and techniques. It should be understood, however, that many variations and modifications may be made while remaining within the spirit and scope of the disclosed subject matter.

The invention claimed is:

1. A controlled-release formulation comprising:
an encapsulating material having an external surface,
a therapeutic or prophylactic compound encapsulated in said encapsulating material, and
a C5a analog attached to the external surface of the encapsulating material, said C5a analog being a C5a receptor agonist having response-selective C5a receptor binding activity, said binding activity comprising activation of antigen presenting cells,
wherein the C5a analog is selected from the group consisting of:

(a) Tyr-Ser-Phe-Lys-Asp-Met-Pro-MeL-(D-Ala)-Arg; (SEQ ID NO: 4)

(b) Tyr-Ser-Phe-Lys-Pro-Met-Pro-Leu-(D-Ala)-Arg; (SEQ ID NO: 3)

(c) Tyr-Ser-Phe-Lys-Asp-Ala-Pro-Leu-(D-Ala)-Arg; (SEQ ID NO: 7)

(d) Tyr-Ser-Phe-Lys-Asp-Met-Pro-Leu-(D-Ala)-Arg; (SEQ ID NO: 8)

(e) Tyr-Ser-Phe-Lys-Asp-Met-Pro-Leu-Gly-Arg; (SEQ ID NO: 9)

(f) Tyr-Ser-Phe-Lys-Asp-Ala-Pro-Leu-Gly-Arg; (SEQ ID NO: 10)

(g) Tyr-Ser-Phe-Lys-Asp-Cys-Pro-Leu-Gly-Arg; (SEQ ID NO: 11)

(h) Tyr-Ser-Phe-Lys-Asp-Met-Pro-Leu-(D-Pro)-Arg; (SEQ ID NO: 12)

(i) Tyr-Ser-Phe-Lys-Asp-Met-Gln-Leu-(D-Ala)-Arg; (SEQ ID NO: 13)

(j) Tyr-Ser-Phe-Lys-Asp-Met-Gln-Leu-Gly-Arg; (SEQ ID NO: 14)

(k) Tyr-Ser-Phe-Lys-Asp-Met-Gln-Pro-Gly-Arg; (SEQ ID NO: 15)

(l) Tyr-Ser-Phe-Lys-Asp-Met-Pro-Leu-Aib-Arg; (SEQ ID NO: 16)

(m) Tyr-Ser-Phe-Lys-Gly-Met-Pro-Leu-Gly-Arg; (SEQ ID NO: 17)
and (n) Tyr-Ser-Phe-Lys-Gly-Leu-Leu-Leu-Gly-Arg. (SEQ ID NO: 18)

2. The controlled-release formulation of claim 1, wherein the encapsulating material is a form selected from the group consisting of a nanoparticle, a nanogel, a microparticle, a microgel, a microcapsule, a nanocapsule, a polyelectrolyte capsule, a biodegradable lattice, a polysaccharide capsule, a block co-polymer micelle, a polyelectrolyte complex, an injectable implant, a diffusion-controlled hydrogel and a micro-emulsion.

3. The controlled-release formulation of claim 2, wherein said encapsulating material is nanoparticles or microparticles, said C5a analog being disposed on the external surface of each particle.

4. The controlled-release formulation of claim 3, wherein said C5a analog is covalently conjugated to said particle surface.

5. The controlled-release formulation of claim 3, wherein said C5a analog is non-covalently associated with said particle surface.

6. The controlled-release formulation of claim 3, wherein said particle is polymer-based nanoparticles or microparticles.

7. The controlled-release formulation of claim 6, wherein said polymer is poly (lactic-co-glycolic acid) (PLGA), ethyl cellulose, polymethyl methacrylate, polyethylene glycol, poly-3-hydroxy butyrate, alginate, collagen, gelatin, a chitin, a chitosan, styrene copolymer, maleic anhydride and poly (N-isopropylacrylamide) copolymer, hyaluronic acid, polyester, polylactide, polyorthoester, polycarbonate, polycaprolactone, or polyethylene oxide.

8. The controlled-release formulation of claim 1, wherein said therapeutic or prophylactic compound is an immunogen.

9. The controlled-release formulation of claim 8, wherein said immunogen is a peptide immunogen characteristic of a biological entity selected from the group consisting of a diseased cell, an infectious bacterium, an infectious parasite, an infectious fungus, an infectious protozoan, an infectious prion, an infectious virus and a biofilm.

10. The controlled-release formulation of claim 8, wherein said immunogen is selected from the group consisting of peptides and proteins, glycopeptides and glycoproteins, phosphopeptides and phosphoproteins, lipopeptides and lipoproteins, carbohydrates, nucleic acids, small molecules and lipids.

11. The controlled-release formulation of claim 1, wherein the C5a analog is EP67 bearing the sequence Tyr-Ser-Phe-Lys-Asp-Met-Pro-MeL-(D-Ala)-Arg (SEQ ID NO: 4) or EP54 bearing the sequence Tyr-Ser-Phe-Lys-Pro-Met-Pro-Leu-(D-Ala)-Arg (SEQ ID NO: 3).

12. A method of selectively activating an immune cell at a site of infection or disease comprising administering an effective amount of a controlled-release formulation according to claim 1 to a patient in need thereof.

13. The method of claim 12, wherein the infection is caused by a bacterium, a parasite, a virus, a fungus, a prion, or a microbial biofilm.

14. The method of claim 12, wherein the disease is cancer.

15. The method of claim 12, wherein said formulation is prophylactically administered to said patient.

16. The method of claim 12, wherein the immune cell is an antigen presenting cell.

17. The method of claim 16, wherein activation of said antigen presenting cells induces an innate and/or acquired immune response in said patient.

* * * * *